US010548973B2

(12) United States Patent
Zhang et al.

(10) Patent No.: US 10,548,973 B2
(45) Date of Patent: Feb. 4, 2020

(54) POLYPEPTIDE CARRIER FOR PRESENTING TARGET POLYPEPTIDE AND USES THEREOF

(71) Applicants: XIAMEN UNIVERSITY, Xiamen (CN); YANG SHENG TANG COMPANY, LTD., Haikou (CN)

(72) Inventors: Tianying Zhang, Xiamen (CN); Quan Yuan, Xiamen (CN); Xueran Guo, Xiamen (CN); Ying Zhang, Xiamen (CN); Qinjian Zhao, Xiamen (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Haikou (CN)

( * ) Notice: Subject to any disclaimer, the term of this patent is extended or adjusted under 35 U.S.C. 154(b) by 63 days.

(21) Appl. No.: 15/754,766

(22) PCT Filed: Aug. 24, 2016

(86) PCT No.: PCT/CN2016/096481

§ 371 (c)(1),
(2) Date: Feb. 23, 2018

(87) PCT Pub. No.: WO2017/032303

PCT Pub. Date: Mar. 2, 2017

(65) Prior Publication Data

US 2019/0247494 A1 Aug. 15, 2019

(30) Foreign Application Priority Data

Aug. 25, 2015 (CN) .......................... 2015 1 0523187

(51) Int. Cl.

| | |
|---|---|
| ***C07H 21/04*** | (2006.01) |
| ***C07K 14/005*** | (2006.01) |
| ***C12Q 1/70*** | (2006.01) |
| ***G01N 33/569*** | (2006.01) |
| ***A61K 31/7088*** | (2006.01) |
| ***A61K 39/29*** | (2006.01) |
| ***A61K 39/385*** | (2006.01) |
| ***C12N 15/62*** | (2006.01) |
| ***C07K 19/00*** | (2006.01) |
| ***C12N 7/04*** | (2006.01) |
| ***A61P 31/20*** | (2006.01) |
| ***A61P 35/00*** | (2006.01) |
| ***A61K 39/39*** | (2006.01) |
| ***C12N 7/00*** | (2006.01) |

(52) U.S. Cl.

CPC ............ *A61K 39/292* (2013.01); *A61K 39/29* (2013.01); *A61K 39/385* (2013.01); *A61K 39/39* (2013.01); *A61P 31/20* (2018.01); *A61P 35/00* (2018.01); *C07K 19/00* (2013.01); *C12N 7/00* (2013.01); *C12N 7/04* (2013.01); *C12N 15/62* (2013.01); *C12N 2730/10122* (2013.01); *C12N 2730/10123* (2013.01)

(58) Field of Classification Search

CPC ....... A61K 39/12; A61K 49/085; A61P 31/14; C07K 14/005; C12N 2770/24021

See application file for complete search history.

(56) References Cited

U.S. PATENT DOCUMENTS

2005/0025782 A1 2/2005 Milich et al.

FOREIGN PATENT DOCUMENTS

| | | | |
|---|---|---|---|
| CN | 102127554 | A | 7/2011 |
| CN | 104211784 | A | 12/2014 |
| WO | WO 2004/073659 | A2 | 9/2004 |

OTHER PUBLICATIONS

Korean Office Action dated Aug. 30, 2019 in Korean Patent Application No. 10-2018-7008233 (with English translation), 7 pages.

Whitacre, PhD., D.C., et al., "Use of hepadnavirus core proteins as vaccine platforms", Expert Rev. Vaccines, Nov. 2009, vol. 8 No. 11. pp. 1565-1573.

Combined Office Action and Search Report dated Apr. 19, 2019 in Chinese Patent Application No. 201610709155.1, 7 pages (with English translation of categories of cited documents).

"Core protein [Roundleaf bat hepatitis B virus]" National Center for Biotechnology Information, NCBI Reference Sequence: YP_009045994.1, https://www.ncbi.nlm.nih.gov/protein/YP_009045994.1/, 2014, 1 page.

(Continued)

*Primary Examiner* — Barry A Chestnut

(74) *Attorney, Agent, or Firm* — Oblon, McClelland, Maier & Neustadt, L.L.P.

(57) ABSTRACT

The invention relates to a polypeptide carrier for presenting a target polypeptide, and use thereof. In particular, the invention relates to a nucleic acid molecule, comprising a nucleotide sequence encoding a polypeptide carrier, and being used for insertion of a nucleotide sequence encoding a target polypeptide. In addition, the invention further relates to a recombinant protein comprising the polypeptide carrier and a target polypeptide. Furthermore, the invention further relates to use of the nucleic acid molecule and the recombinant protein. In addition, the invention further relates to a vaccine or a pharmaceutical composition useful for preventing, alleviating or treating HBV infection or a disease associated with HBV infection (e.g., hepatitis B), comprising a recombinant protein comprising the polypeptide carrier of the invention and an epitope from HBV.

15 Claims, 9 Drawing Sheets

Specification includes a Sequence Listing.

(56) References Cited

OTHER PUBLICATIONS

Lingjiang, Y. "Foreign Medical Sciences, Section of Biological Products for Prophylaxis, Diagnosis and Therapy", China Academic Journal Electronic Publishing House, 2002, pp. 201-206 (with English Abstract).
Extended European Search Report dated Jan. 30, 2019 in European Patent Application No. 16838561.5, 10 pages.
"Hepatitis B virus isolate HBV-N10, complete genome", XP002787438, Sep. 26, 2004, Retrieved from EBI accession No. EMBL: AY707087, 4 pages.
Roose, K., et al., "Hepatitis B Core-based virus-like particles to present heterologous epitopes", 2013, Expert Review, pp. 183-198.
Hai-Jie, Y., et al., "Construction of Peptide Display Vector Based on HBV Core Protein", Journal of Xiamen University (Natural Science), vol. 43 No. 4, Jul. 2004, pp. 436-438 (with English abstract).
Jian-Nan, Z., et al., "Secretion Expression of Hepatitis B Core Antigen Particles Harboring HEV Receptor-associated Epitope in *Pichia pastoris*", Journal of Xiamen University (Natural Science), Jan. 2009, vol. 48 No. 1, pp. 107-111 (with English abstract).
Drexler, J F. et al., "Bats Carry pathogenic hepadnaviruses antigenically related to hepatitis B virus and capable of infecting human hepatocytes", PNAS, Oct. 1, 2013, vol. 110 No. 40, pp. 16151-16156.
International Search Report dated Nov. 25, 2016 in PCT/CN2016/096481 filed Aug. 24, 2016.
Jun Long et al., "Cloning, Expression, Separation and Purification of Particle-Like Protein Loading CETP Polypeptide Epitopes", Pharmaceutical Biotechnology, 2006, vol. 13, No. 4, pp. 237-243 (with English abstract).
F. Schödel et al., "Hybrid hepatitis B virus core antigen as a vaccine carrier moiety: I. Presentation of foreign epitopes", Journal of Biotechnology, 1996, vol. 44, pp. 91-96.

POLYPEPTIDE CARRIER FOR PRESENTING TARGET POLYPEPTIDE AND USES THEREOF

TECHNICAL FIELD

The invention relates to the fields of genetically engineering vaccines, molecular virology and immunology. In addition, the invention specifically relates to the field of treatment of Hepatitis B virus (HBV) infection. In particular, the invention relates to a nucleic acid molecule, comprising a nucleotide sequence encoding a polypeptide carrier (peptide carrier), and being used for insertion of a nucleotide sequence encoding a target polypeptide. In particular, after the nucleic acid molecule of the invention has a nucleotide sequence encoding a target polypeptide inserted therein and is expressed as a recombinant protein, the polypeptide carrier can present the target polypeptide (e.g., a target antigen or a target epitope in an antigen), and/or the recombinant protein can form a virus-like particle and present the target polypeptide. In addition, the invention further relates to a recombinant protein comprising the polypeptide carrier and a target polypeptide. Furthermore, the invention further relates to use of the nucleic acid molecule and the recombinant protein. In addition, the invention specifically relates to a vaccine or a pharmaceutical composition useful for preventing, alleviating or treating HBV infection or a disease associated with HBV infection (e.g., hepatitis B), comprising a recombinant protein comprising the polypeptide carrier of the invention and an epitope from HBV.

BACKGROUND ART

Vaccines are effective means for combating infectious diseases. Depending on applicable people, vaccines can be divided into prophylactic vaccines and therapeutic vaccines. Prophylactic vaccines are mainly used to prevent virus infections, including attenuated vaccines, inactivated vaccines, and genetically engineering vaccines, which protect organisms from virus infections mainly by inducing neutralizing antibodies in the organisms. Therapeutic vaccines are mainly used to treat persistent virus infection and diseases such as tumor. In these diseases, patients are generally immune-tolerant to a target antigen, and therefore, researchers have tried several forms of vaccines to induce generation of an effective immune response to a target antigen in organisms. Therapeutic vaccines mainly include nucleic acid vaccines, viral vector vaccines, genetically engineering vaccines, etc. Among them, genetically engineering vaccines have significant advantages.

The genetically engineering vaccines that have been commercially available, include hepatitis B virus (HBV) vaccines, Human Papillomavirus (HPV) vaccines, and Hepatitis E virus (HEV) vaccines, all of which are in the form of virus-like particles (VLPs). Virus-like particles refer to hollow particles formed by one or more structural proteins of a certain virus, which do not comprise viral nucleic acid, cannot be self-replicated, but are the same as or similar to true virions in terms of morphology and structure. Virus-like particles have the following advantages: strong immunogenicity, high safety, being not easily inactivated, and being able to present an exogenous peptide fragment and induce specific immune response to the exogenous peptide fragment in organisms; and therefore, have an important application value in the field of vaccines.

Now, about 2 billion people have been infected by HBV worldwide, about 350 million of which have chronic HBV infection, and the risk of these infected people finally dying of liver diseases associated with HBV infection could reach 15%-25%. More than 1 million people died of end-stage liver diseases caused by hepatitis B worldwide every year. China is an area severely afflicted by HBV infection, and there are about 93 million people carrying hepatitis B now. In recent years, with the continuous improvement of the case reporting system, the incidence and mortality of hepatitis B-related diseases increase instead of decreasing.

At present, drugs for treating chronic HBV infection can mainly be divided into two classes, i.e., Interferon and nucleoside/nucleotide analogues (NAs). The final goal of treating chronic HBV infection is to prevent the occurrence of end-stage liver diseases such as serious hepatitis (hepatic failure), hepatic cirrhosis and liver cancer; the best clinical endpoint is to enable patients to achieve serological negative conversion or serological conversion of hepatitis B surface antigen, i.e., completely clean HBV. However, there are a very limited number of existing drugs that can achieve the goal. Therefore, it is urgent and necessary to develop novel, creative therapeutic drugs and methods that can clean virus more effectively, in particular, can clean HBsAg effectively or greatly decrease HBsAg level, for patients with chronic HBV infection, and it is a potential strategy to develop therapeutic vaccines.

CONTENTS OF INVENTION

The inventors of the present application, based on three bat-derived hepatitis B virus core antigens (i.e., roundleaf bat HBV (RBHBV) core antigen (RBHBcAg); tent-making bat HBV (TBHBV) core antigen (TBHBcAg); and horseshoe bat HBV (HBHBV) core antigen (HBHBcAg)), have developed a class of new polypeptide carriers (peptide carriers) for presenting target polypeptides. Therefore, the invention provides a nucleic acid molecule, comprising a nucleotide sequence encoding a polypeptide carrier. Such a nucleic acid molecule can have a nucleotide sequence encoding a target polypeptide inserted therein, and be expressed as a recombinant protein comprising the polypeptide carrier and the target polypeptide (e.g., a target antigen, or a target epitope in an antigen). Furthermore, the recombinant protein produced can form VLP effectively, and can present the target polypeptide inserted therein on the surface of VLP, so that the target polypeptide can be effectively recognized by immune system in an organism, thereby inducing generation of a specific immune response to the target polypeptide in the organism. Therefore, the polypeptide carrier of the invention, can be used as a carrier for vaccine, to present a target polypeptide, for example, a peptide fragment (e.g., an epitope) from a target antigen; and a recombinant protein comprising the polypeptide carrier of the invention and a target polypeptide can be used as a vaccine, to induce a specific immune response to the target polypeptide in an organism.

In addition, the inventors of the present application also found surprisingly that the C-terminus of RBHBcAg protein, TBHBcAg protein and HBHBcAg protein is a lysine-rich region, and is not necessary for the assembly of VLP. Therefore, the polypeptide carrier of the invention may not comprise the C-terminus of RBHBcAg protein, TBHBcAg protein and HBHBcAg protein. For example, the RBHBcAg carrier of the invention may have the amino acids from positions 145-189 of RBHBcAg protein deleted partially or completely (e.g., have the amino acids from positions 150-189 of RBHBcAg protein deleted); the TBHBcAg carrier of the invention may have the amino acids from positions 149-188 of TBHBcAg protein deleted partially or completely (e.g., have the amino acids from positions 154-188 of TBHBcAg protein deleted); the HBHBcAg carrier of the invention may have the amino acids from positions 145-189 of HBHBcAg protein deleted partially or completely (e.g., have the amino acids from positions 150-189 of HBHBcAg protein deleted).

In addition, the inventors of the present application also found surprisingly that the polypeptide carrier of the invention is particularly suitable for presenting antigen epitope from human hepatitis B virus (e.g., an epitope of HBsAg from human HBV), and is able to induce a very strong and specific immune response for cleaning HBsAg in a subject, with an efficacy significantly better than that of the existing hepatitis B vaccines (e.g., vaccines comprising the same epitope and constructed by using HBcAg of human HBV as a polypeptide carrier). Thus, the invention further provides a polypeptide carrier particularly suitable for presenting antigen epitopes from human hepatitis B virus.

Therefore, in an aspect, the invention provides a nucleic acid molecule, comprising a nucleotide sequence encoding a polypeptide carrier, or a variant thereof, wherein the variant has an identity of at least 90% (e.g., at least 91%, 92%, 93%, 94%, 95%, 96%, 97%, 98%, or 99%) to the nucleotide sequence, or is capable of hybridizing to the nucleotide sequence under a stringent condition or a high stringent condition, wherein, the polypeptide carrier is selected from:

(1) RBHBcAg carrier, which differs from roundleaf bat HBV core antigen protein (RBHBcAg; e.g., its amino acid sequence is set forth in SEQ ID NO: 1) in that: (a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of RBHBcAg protein are deleted or substituted with a linker (e.g., a flexible linker; e.g., a linker set forth in SEQ ID NO: 43); and (b) optionally, 1-40 amino acid residues (e.g., 1-5, 5-10, 10-15, 15-20, 20-25, 25-30, 30-35, or 35-40 amino acid residues) are deleted at C-terminus of RBHBcAg protein;

(2) TBHBcAg carrier, which differs from tent-making bat HBV core antigen protein (TBHBcAg; e.g., its amino acid sequence is set forth in SEQ ID NO: 2) in that: (a) one or more amino acid residues (e.g., 1, 2, 3, 4 or 5 amino acid residues; e.g., amino acid residues from positions 80-84, amino acid residues from positions 80-83, or amino acid residues from positions 80-82) of the amino acid residues from positions 80-84 at N-terminus of TBHBcAg protein are deleted or substituted with a linker (e.g., a flexible linker; e.g., a linker set forth in SEQ ID NO: 43); and (b) optionally, 1-35 amino acid residues (e.g., 1-5, 5-10, 10-15, 15-20, 20-25, 25-30, or 30-35 amino acid residues) are deleted at C-terminus of TBHBcAg; or (3) HBHBcAg carrier, which differs from horseshoe bat HBV core antigen protein (HBHBcAg; e.g., its amino acid sequence is set forth in SEQ ID NO: 3) in that: (a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of HBHBcAg protein are deleted or substituted with a linker (e.g., a flexible linker; e.g., a linker set forth in SEQ ID NO: 43); and (b) optionally, 1-40 amino acid residues (e.g., 1-5, 5-10, 10-15, 15-20, 20-25, 25-30, 30-35, or 35-40 amino acid residues) are deleted at C-terminus of HBHBcAg protein.

In a preferred embodiment, the variant has an identity of at least 90%, e.g., an identify of at least 91%, at least 92%, at least 93%, at least 94%, at least 95%, at least 96%, at least 97%, at least 98%, or at least 99%, to the nucleotide sequence encoding the polypeptide carrier.

In a preferred embodiment, the variant is capable of hybridizing to the nucleotide sequence encoding the polypeptide carrier under a stringent condition. In a preferred embodiment, the variant is capable of hybridizing to the nucleotide sequence encoding the polypeptide carrier under a high stringent condition.

In a preferred embodiment, RBHBcAg protein is a wild type RBHBcAg. In a preferred embodiment, the amino acid sequence of RBHBcAg protein is set forth in SEQ ID NO: 1.

In a preferred embodiment, RBHBcAg carrier differs from RBHBcAg protein in that one or more contiguous amino acid residues (e.g., 1, 2, 3, 4, 5 or 6 contiguous amino acid residues) of the amino acid residues from positions 78-83 at N-terminus of RBHBcAg protein are deleted or substituted with a linker. For example, the amino acid residues from positions 78-83, amino acid residues from positions 78-82, amino acid residues from positions 78-81, amino acid residues from positions 78-80, amino acid residues from positions 78-79, amino acid residues from positions 79-83, amino acid residues from positions 79-82, amino acid residues from positions 79-81, amino acid residues from positions 79-80, amino acid residues from positions 80-83, amino acid residues from positions 80-82, amino acid residues from positions 80-81, amino acid residues from positions 81-83, amino acid residues from positions 81-82, amino acid residues from positions 82-83, amino acid residue at position 78, amino acid residue at position 79, amino acid residue at position 80, amino acid residue at position 81, amino acid residue at position 82, or amino acid residue at position 83, at N-terminus of RBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

In a preferred embodiment, RBHBcAg carrier differs from RBHBcAg protein in that: (1) one or more contiguous amino acid residues (e.g., 1, 2, 3, 4, 5 or 6 contiguous amino acid residues) of the amino acid residues from positions 78-83 at N-terminus of RBHBcAg protein are deleted or substituted with a linker, as defined above; and (2) 1-40 amino acid residues at C-terminus of RBHBcAg protein are deleted. In a preferred embodiment, 1-5, 5-10, 10-15, 15-20, 20-25, 25-30, 30-35, or 35-40 amino acid residues are deleted at C-terminus of RBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues, are deleted.

In a preferred embodiment, TBHBcAg protein is a wild type TBHBcAg. In a preferred embodiment, the amino acid sequence of TBHBcAg protein is set forth in SEQ ID NO: 2.

In a preferred embodiment, TBHBcAg carrier differs from TBHBcAg protein in that one or more contiguous amino acid residues (e.g., 1, 2, 3, 4, or 5 contiguous amino acid residues) of the amino acid residues from positions 80-84 at N-terminus of TBHBcAg protein are deleted or substituted with a linker. For example, the amino acid residues from positions 80-84, amino acid residues from positions 80-83, amino acid residues from positions 80-82, amino acid residues from positions 80-81, amino acid residues from positions 81-84, amino acid residues from positions 81-83, amino acid residues from positions 81-82, amino acid residues from positions 82-84, amino acid residues from positions 82-83, amino acid residues from positions 83-84, amino acid residue at position 80, amino acid residue at position 81, amino acid residue at position 82, amino acid residue at position 83, or amino acid residue at position 84, at N-terminus of TBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

In a preferred embodiment, TBHBcAg carrier differs from TBHBcAg protein in that: (1) one or more contiguous amino acid residues (e.g., 1, 2, 3, 4, or 5 contiguous amino acid residues) of the amino acid residues from positions 80-84 at N-terminus of TBHBcAg protein are deleted or substituted with a linker, as defined above; and (2) 1-35 amino acid residues at C-terminus of TBHBcAg protein are deleted. In a preferred embodiment, 1-5, 5-10, 10-15, 15-20, 20-25, 25-30, or 30-35 amino acid residues are deleted at C-terminus of TBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues are deleted.

In a preferred embodiment, HBHBcAg protein is a wild type HBHBcAg. In a preferred embodiment, the amino acid sequence of HBHBcAg is set forth in SEQ ID NO: 3.

In a preferred embodiment, HBHBcAg carrier differs from HBHBcAg protein in that one or more contiguous amino acid residues (e.g., 1, 2, 3, 4, 5 or 6 contiguous amino acid residues) of the amino acid residues from positions 78-83 at N-terminus of HBHBcAg protein are deleted or substituted with a linker. For example, the amino acid residues from positions 78-83, amino acid residues from positions 78-82, amino acid residues from positions 78-81, amino acid residues from positions 78-80, amino acid residues from positions 78-79, amino acid residues from positions 79-83, amino acid residues from positions 79-82, amino acid residues from positions 79-81, amino acid residues from positions 79-80, amino acid residues from positions 80-83, amino acid residues from positions 80-82, amino acid residues from positions 80-81, amino acid residues from positions 81-83, amino acid residues from positions 81-82, amino acid residues from positions 82-83, amino acid residue at position 78, amino acid residue at position 79, amino acid residue at position 80, amino acid residue at position 81, amino acid residue at position 82, or amino acid residue at position 83, at N-terminus of HBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

In a preferred embodiment, HBHBcAg carrier differs from HBHBcAg protein in that: (1) one or more contiguous amino acid residues (e.g., 1, 2, 3, 4, 5 or 6 contiguous amino acid residues) of the amino acid residues from positions 78-83 at N-terminus of HBHBcAg protein are deleted or substituted with a linker, as defined above; and (2) 1-40 amino acid residues at C-terminus of HBHBcAg protein are deleted. In a preferred embodiment, 1-5, 5-10, 10-15, 15-20, 20-25, 25-30, 30-35, or 35-40 amino acid residues are deleted at C-terminus of HBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues are deleted.

As known by a person skilled in the art, introduction of a restriction enzyme cleavage site is particularly advantageous. Therefore, in a preferred embodiment, in the nucleic acid molecule of the invention, a restriction enzyme cleavage site is introduced at a position of nucleotides encoding the one or more amino acid residues that are deleted. In a preferred embodiment, in the nucleic acid molecule of the invention, a restriction enzyme cleavage site is introduced in the nucleotide sequence encoding the linker and/or at either or both of the termini thereof. In a preferred embodiment, one or more restriction enzyme cleavage sites are introduced in the nucleic acid molecule of the invention and/or at either or both of the termini thereof. A variety of restriction enzyme cleavage sites are known by a person skilled in the art, including, but not limited to, enzyme cleavage sites recognized by restriction enzymes such as EcoR I, BamH I, Hind II, Hind III, Hpa I, Hpa II, Mbo I, and Mbo II.

In a preferred embodiment, the polypeptide carrier has an amino acid sequence selected from SEQ ID NO: 4-9.

In a preferred embodiment, the nucleic acid molecule comprises a nucleotide sequence selected from SEQ ID NO: 12-17.

In a preferred embodiment, the nucleic acid molecule is used for insertion of a nucleotide sequence encoding a target polypeptide. For example, the nucleotide sequence encoding a target polypeptide is inserted at a position of nucleotides encoding the one or more amino acid residues that are deleted, or is inserted in the nucleotide sequence encoding the linker or at either or both of the termini thereof. In a preferred embodiment, in an in-frame manner, the nucleotide sequence encoding a target polypeptide is inserted into the nucleotide sequence encoding the polypeptide carrier. In a preferred embodiment, by virtue of a restriction enzyme cleavage site, the nucleotide sequence encoding a target polypeptide is inserted into the nucleotide sequence encoding the polypeptide carrier.

In a preferred embodiment, the nucleic acid molecule further comprises a nucleotide sequence encoding a target polypeptide, wherein the target polypeptide is heterologous relative to the polypeptide carrier, and the nucleotide sequence encoding the target polypeptide is inserted at a position of nucleotides encoding the one or more amino acid residues that are deleted, or is inserted in the nucleotide sequence encoding the linker or at either or both of the termini thereof. In a preferred embodiment, in an in-frame manner, the nucleotide sequence encoding the target polypeptide is inserted in the nucleotide sequence encoding the polypeptide carrier. In a preferred embodiment, by virtue of a restriction enzyme cleavage site, the nucleotide sequence encoding the target polypeptide is inserted in the nucleotide sequence encoding the polypeptide carrier.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV).

In a preferred embodiment, the target polypeptide comprises or is HBsAg of human HBV or an epitope peptide comprising an epitope (e.g., a linear epitope) of HBsAg. In a preferred embodiment, the polypeptide carrier is RBHBcAg carrier, and the epitope peptide comprises or is an antigenic epitope from HIV, PDL1 or HBV (particularly human HBV) (e.g., an epitope (e.g., a linear epitope) of HBsAg from human HBV). In a preferred embodiment, the polypeptide carrier is TBHBcAg carrier, and the epitope peptide comprises or is an antigenic epitope from HIV, PDL1 or HBV (particularly human HBV) (e.g., an epitope (e.g., a linear epitope) of HBsAg from human HBV). In a preferred embodiment, the polypeptide carrier is HBHBcAg carrier, and the epitope peptide comprises or is an antigenic epitope from HIV, PDL1 or HBV (particularly human HBV) (e.g., an epitope (e.g., a linear epitope) of HBsAg from human HBV).

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of said GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the nucleic acid molecule comprises or consists of a nucleotide sequence encoding an amino acid sequence selected from SEQ ID NO: 23-40 and 69-74.

In another aspect, the invention relates to a vector comprising the nucleic acid molecule of the invention as defined above.

Vectors for insertion of a target polynucleotide (e.g., the nucleic acid molecule of the invention) are well known in the art, including, but not limited to, cloning vectors and expression vectors. In a preferred embodiment, the vector of the invention may be a eukaryotic expression vector or a prokaryotic expression vector. In a preferred embodiment, the vector of the invention is, for example, plasmid, cosmid, or phage, etc.

In another aspect, the invention further relates to a host cell comprising the nucleic acid molecule or vector. Such host cells include, but are not limited to, prokaryotic cells such as *E. coli* cells, and eukaryotic cells such as yeast cells, insect cells, plant cells and animal cells (such as mammalian cells, e.g., mouse cells, human cells, etc.). The host cell of the invention may also be a cell line, such as 293T cell.

In another aspect, the invention relates to a method for presenting a target polypeptide, comprising:

(1) inserting a nucleotide sequence encoding the target polypeptide into the nucleic acid molecule of the invention (particularly, into the nucleotide sequence encoding the polypeptide carrier), so as to obtain a nucleic acid molecule encoding a recombinant protein; and (2) expressing the nucleic acid molecule encoding the recombinant protein in the step (1) to produce a recombinant protein.

In a preferred embodiment, the target polypeptide is heterologous relative to the polypeptide carrier. In a preferred embodiment, the nucleotide sequence encoding the target polypeptide is inserted at a position of nucleotides encoding the one or more amino acid residues that are deleted, or is inserted in the nucleotide sequence encoding the linker or at either or both of the termini thereof. In a preferred embodiment, in an in-frame manner, the nucleotide sequence encoding the target polypeptide is inserted in the nucleotide sequence encoding the polypeptide carrier. In a preferred embodiment, by virtue of a restriction enzyme cleavage site, the nucleotide sequence encoding the target polypeptide is inserted in the nucleotide sequence encoding the polypeptide carrier.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV).

In a preferred embodiment, the target polypeptide comprises or is HBsAg of human HBV or an epitope peptide comprising an epitope (e.g., a linear epitope) of HBsAg. In a preferred embodiment, the polypeptide carrier is RBHBcAg carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is TBHBcAg carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is HBHBcAg carrier, and the epitope peptide comprises or is an antigenic epitope from HIV, PDL1 or HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of said GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the nucleic acid molecule encoding the recombinant protein comprises or consists of a nucleotide sequence encoding an amino acid sequence selected from SEQ ID NO: 23-40 and 69-74.

In another aspect, the invention relates to a recombinant protein, comprising a polypeptide carrier and a target polypeptide, wherein, the polypeptide carrier has the same meanings as defined above, and, the target polypeptide is inserted in the polypeptide carrier.

In a preferred embodiment, the target polypeptide is inserted at a position of the one or more amino acid residues that are deleted, or inserted in the linker or at either or both of the termini thereof.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is TBHBcAg carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is HBHBcAg carrier, and the epitope peptide comprises or is an antigenic epitope from HIV, PDL1 or HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the polypeptide carrier has an amino acid sequence selected from SEQ ID NO: 4-9. In a preferred embodiment, the recombinant protein comprises or consists of an amino acid sequence selected from SEQ ID NO: 23-40 and 69-74.

In another aspect, the invention relates to a virus-like particle, comprising or consisting of the recombinant protein of the invention.

In another aspect, the invention relates to a pharmaceutical composition (e.g., a vaccine), comprising the recombinant protein of the invention or the virus-like particle of the invention, and optionally, one or more pharmaceutically acceptable vehicles or excipients (e.g., adjuvants). In a preferred embodiment, the recombinant protein of the invention or the virus-like particle of the invention is present in an effective amount in the pharmaceutical composition. For example, the pharmaceutical composition of the invention may comprise the recombinant protein or the virus-like particle in an amount effective for the prevention or treatment of HBV infection or a disease associated with HBV infection (e.g., hepatitis B).

In another aspect, the invention relates to a method for preventing or treating HBV infection or a disease associated with HBV infection (e.g., hepatitis B), comprising administering to a subject in need thereof the recombinant protein or virus-like particle or pharmaceutical composition of the invention, wherein the target polypeptide comprises an antigenic epitope from HBV (particularly human HBV). In a preferred embodiment, the target polypeptide is an epitope peptide comprising an antigenic epitope from HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40 and 69-74.

In a preferred embodiment, the recombinant protein or virus-like particle or pharmaceutical composition of the invention is administered in an amount effective for preventing or treating HBV infection or a disease associated with HBV infection (e.g., hepatitis B).

In another aspect, the invention relates to use of the recombinant protein or virus-like particle in the manufacture of a medicament for preventing or treating HBV infection or a disease associated with HBV infection (e.g., hepatitis B), wherein the target polypeptide comprises an antigenic epitope from HBV (particularly human HBV). In a preferred embodiment, the target polypeptide is an epitope peptide comprising an antigenic epitope from HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40 and 69-74.

In another aspect, the invention relates to the recombinant protein or virus-like particle or pharmaceutical composition of the invention, for use in the prevention or treatment of HBV infection or a disease associated with HBV infection (e.g., hepatitis B), wherein the target polypeptide comprises an antigenic epitope from HBV (particularly human HBV). In a preferred embodiment, the target polypeptide is an epitope peptide comprising an antigenic epitope from HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40 and 69-74.

In another aspect, the invention relates to a method for preventing or treating HIV infection or a disease associated with HIV infection (e.g., AIDS), comprising administering to a subject in need thereof the recombinant protein or virus-like particle or pharmaceutical composition of the invention, wherein the target polypeptide comprises an antigenic epitope of HIV. In a preferred embodiment, the target polypeptide is an epitope peptide comprising an antigenic epitope from HIV. In a preferred embodiment, the target polypeptide comprises or is HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In a preferred embodiment, the recombinant protein or virus-like particle or pharmaceutical composition of the invention is administered in an amount effective for preventing or treating HIV infection or a disease associated with HIV infection (e.g., AIDS).

In another aspect, the invention relates to use of the recombinant protein or virus-like particle of the invention in the manufacture of a medicament for preventing or treating HIV infection or a disease associated with HIV infection (e.g., AIDS), wherein the target polypeptide comprises an antigenic epitope from HIV. In a preferred embodiment, the target polypeptide is an epitope peptide comprising an antigenic epitope from HIV. In a preferred embodiment, the target polypeptide comprises or is selected from HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In another aspect, the invention relates to the recombinant protein or virus-like particle or pharmaceutical composition of the invention, for use in the prevention or treatment of HIV infection or a disease associated with HIV infection (e.g., AIDS), wherein the target polypeptide comprises an antigenic epitope from HIV. In a preferred embodiment, the target polypeptide is an epitope peptide comprising an antigenic epitope from HIV. In a preferred embodiment, the target polypeptide comprises or is HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In another aspect, the invention relates to a method for preventing or treating cancer (e.g., non-small cell lung cancer), comprising administering to a subject in need thereof the recombinant protein or virus-like particle or pharmaceutical composition of the invention, wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In a preferred embodiment, the recombinant protein or virus-like particle or pharmaceutical composition of the invention is administered in an amount effective for preventing or treating cancer (e.g., non-small cell lung cancer).

In another aspect, the invention relates to use of the recombinant protein or virus-like particle in the manufacture of a medicament for preventing or treating cancer (e.g., non-small cell lung cancer), wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In another aspect, the invention relates to the recombinant protein or virus-like particle or pharmaceutical composition, for use in the prevention or treatment of cancer (e.g., non-small cell lung cancer), wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In another aspect, the invention relates to a polynucleotide encoding the recombinant protein and a vector comprising the polynucleotide.

Vectors for insertion of a target polynucleotide (e.g., the nucleic acid molecule of the invention) are well known in the art, including, but not limited to cloning vectors and expression vectors. In a preferred embodiment, the vector of the invention may be a eukaryotic expression vector or a prokaryotic expression vector. In a preferred embodiment, the vector of the invention is, for example, plasmid, cosmid, or phage, etc.

In another aspect, the invention further relates to a host cell comprising the polynucleotide or vector. Such host cells include, but are not limited to, prokaryotic cells such as *E. coli* cells, and eukaryotic cells such as yeast cells, insect cells, plant cells and animal cells (such as mammalian cells, e.g., mouse cells, human cells, etc.). The host cell of the invention may also be a cell line, such as 293T cell.

In another aspect, the invention further relates to a method for preparing the recombinant protein, comprising culturing the host cell of the invention under the condition suitable for expressing the recombinant protein, and, recovering the recombinant protein.

DEFINITIONS AND EXPLANATIONS OF THE RELEVANT TERMS IN THE INVENTION

In the invention, unless otherwise specified, the scientific and technical terms used herein have the meanings as generally understood by a person skilled in the art. Moreover, the laboratory operating steps of cell culture, molecular genetics, nucleic acid chemistry and immunology used herein are the routine steps widely used in the corresponding fields. In addition, in order to better understand the invention, the definitions and explanations of the relevant terms are provided as follows.

As used herein, the terms “roundleaf bat HBV core antigen protein (RBHBcAg)” and “RBHBcAg protein” refer to a core antigen protein from roundleaf bat HBV (RBHBV), which is well known by a person skilled in the art (see, for example, NCBI GENBANK Accession Number: KC790373.1).

As used herein, when the amino acid sequence of RBHBcAg protein is mentioned, it is described by reference to the sequence set forth in SEQ ID NO: 1. For example, the expression “amino acid residues from positions 78-83 at N-terminus of RBHBcAg protein” refers to amino acid residues from positions 78-83 of the polypeptide set forth in SEQ ID NO: 1. However, a person skilled in the art understands that mutations or variations (including, but not limited to, substitution, deletion and/or addition, e.g., RBHBcAg protein of a different genotype or gene subtype) may occur naturally in or be introduced artificially into the amino acid sequence of RBHBcAg protein without affecting the biological properties thereof. Therefore, in the invention, the term “RBHBcAg protein” intends to include all such sequences, including the sequence set forth in SEQ ID NO: 1 and its natural or artificial variants. In addition, when sequence fragments of RBHBcAg protein are described, they include not only the sequence fragments of SEQ ID NO: 1, but also the corresponding sequence fragments of its natural or artificial variants. For example, the expression “amino acid residues from positions 78-83 at N-terminus of RBHBcAg protein” includes amino acid residues from positions 78-83 of SEQ ID NO: 1, and the corresponding fragments of its variants (natural or artificial variants). According to the invention, the expression “corresponding sequence fragments” or “corresponding fragments” refers to the fragments that are located at equal positions of sequences when the sequences are subjected to optimized alignment, namely, the sequences are aligned to obtain a highest percentage of identity.

As used herein, the term “wild type RBHBcAg” refers to a naturally occurring core antigen protein in roundleaf bat HBV.

As used herein, the term “RBHBcAg carrier” refers to a polypeptide carrier derived from RBHBcAg protein. As described in detail above, RBHBcAg carrier differs from RBHBcAg protein in that: (a) one or more amino acid residues of the amino acid residues from positions 78-83 at N-terminus of RBHBcAg protein are deleted or substituted with a linker; and (b) optionally, 1-40 amino acid residues are deleted at C-terminus of RBHBcAg protein.

As used herein, the terms “tent-making bat HBV core antigen (TBHBcAg)” and “TBHBcAg protein” refer to a core antigen protein from tent-making bat HBV (TBHBV), which is well known by a person skilled in the art (see, for example, NCBI GENBANK Accession Number: KC790378.1).

As used herein, when the amino acid sequence of TBHBcAg protein is mentioned, it is described by reference to the sequence set forth in SEQ ID NO: 2. For example, the expression “amino acid residues from positions 80-84 at N-terminus of TBHBcAg protein” refers to amino acid residues from positions 80-84 of the polypeptide set forth in SEQ ID NO: 2. However, a person skilled in the art understands that mutations or variations (including, but not limited to, substitution, deletion and/or addition, e.g., TBHBcAg protein of a different genotype or gene subtype) may occur naturally in or be introduced artificially into the amino acid sequence of TBHBcAg protein without affecting the biological properties thereof. Therefore, in the invention, the term "TBHBcAg protein" intends to include all such sequences, including the sequence set forth in SEQ ID NO: 2 and its natural or artificial variants. In addition, when sequence fragments of TBHBcAg protein are described, they include not only the sequence fragments of SEQ ID NO: 2, but also the corresponding sequence fragments of its natural or artificial variants. For example, the expression "amino acid residues from positions 80-84 at N-terminus of TBHBcAg protein" includes amino acid residues from positions 80-84 of SEQ ID NO: 2, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the term "wile type TBHBcAg" refers to a naturally occurring core antigen protein in tent-making bat HBV.

As used herein, the term "TBHBcAg carrier" refers to a polypeptide carrier derived from TBHBcAg protein. As described in detail above, TBHBcAg carrier differs from TBHBcAg protein in that: (a) one or more amino acid residues of the amino acid residues from positions 80-84 at N-terminus of TBHBcAg protein are deleted or substituted with a linker; and (b) optionally, 1-35 amino acid residues are deleted at C-terminus of TBHBcAg protein.

As used herein, the terms "horseshoe bat HBV core antigen (HBHBcAg)" and "HBHBcAg protein" refer to a core antigen protein from horseshoe bat HBV (HBHBV), which is well known by a person skilled in the art (see, for example, NCBI GENBANK Accession Number: KC790377.1).

As used herein, when the amino acid sequence of HBHBcAg protein is mentioned, it is described by reference to the sequence set forth in SEQ ID NO: 3. For example, the expression "amino acid residues from positions 78-83 at N-terminus of HBHBcAg protein" refers to amino acid residues from positions 78-83 of the polypeptide set forth in SEQ ID NO: 3. However, a person skilled in the art understands that mutations or variations (including, but not limited to, substitution, deletion and/or addition, e.g., HBHBcAg protein of a different genotype or gene subtype) may occur naturally in or be introduced artificially into the amino acid sequence of HBHBcAg protein without affecting the biological properties thereof. Therefore, in the invention, the term "HBHBcAg protein" intends to include all such sequences, including the sequence set forth in SEQ ID NO: 3 and its natural or artificial variants. In addition, when sequence fragments of HBHBcAg protein are described, they include not only the sequence fragments of SEQ ID NO: 3, but also the corresponding sequence fragments of its natural or artificial variants. For example, the expression "amino acid residues from positions 78-83 at N-terminus of HBHBcAg protein" includes amino acid residues from positions 78-83 of SEQ ID NO: 3, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the term "wile type HBHBcAg" refers to a naturally occurring core antigen protein in horseshoe bat HBV.

As used herein, the term "HBHBcAg carrier" refers to a polypeptide carrier derived from HBHBcAg protein. As described in detail above, HBHBcAg carrier differs from HBHBcAg protein in that: (a) one or more amino acid residues of the amino acid residues from positions 78-83 at N-terminus of HBHBcAg protein are deleted or substituted with a linker; and (b) optionally, 1-40 amino acid residues are deleted at C-terminus of HBHBcAg protein.

As used herein, the terms "human HBV HBcAg" and "Hu-HBcAg" refer to the core antigen protein of human hepatitis B virus, which is well known by a person skilled in the art (see, for example, NCBI GENBANK Accession Number: AAO63517.1). As used herein, when the amino acid sequence of human HBV HBcAg is mentioned, it is described by the sequence set forth in NCBI GENBANK Accession Number: AAO63517.1.

As used herein, the terms "human HBV HBsAg" and "Hu-HBsAg" refer to the surface antigen protein of human hepatitis B virus, which is well known by a person skilled in the art (see, for example, NCBI GENBANK Accession Number: AAF24729.1).

As used herein, when the amino acid sequence of human HBV HBsAg is mentioned, it is described by reference to the sequence set forth in SEQ ID NO: 44 (i.e., NCBI GENBANK Accession Number: AAF24729.1). For example, the expression "amino acid residues from positions 113-135 of HBsAg protein" refers to amino acid residues from positions 113-135 of the polypeptide set forth in SEQ ID NO: 44. However, a person skilled in the art understands that mutations or variations (including, but not limited to, substitution, deletion and/or addition, e.g., HBsAg protein of a different genotype or gene subtype) may occur naturally in or be introduced artificially into the amino acid sequence of HBsAg protein without affecting the biological properties thereof. Therefore, in the invention, the term "HBsAg protein" intends to include all such sequences, including the sequence set forth in SEQ ID NO: 44 and its natural or artificial variants. In addition, when sequence fragments of HBsAg protein are described, they include not only the sequence fragments of SEQ ID NO: 44, but also the corresponding sequence fragments of its natural or artificial variants. For example, the expression "amino acid residues from positions 113-135 of HBsAg protein" includes amino acid residues from positions 113-135 of SEQ ID NO: 44, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the expression "Y amino acid residues deleted at C-terminus of X protein" means that the last Y amino acid residues at C-terminus of X protein are completely deleted. For example, the expression "1-40 amino acid residues deleted at C-terminus of RBHBcAg protein" means that the last 1-40 amino acid residues at C-terminus of RBHBcAg protein are completely deleted.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at www (dot) gcg (dot) com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the biological activity of a protein or polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the term "hybridization" refers to the process of forming a double stranded nucleic acid by annealing two single-stranded nucleic acid molecules having complementary sequences based on the principle of complementary base pairing under certain conditions (e.g. suitable temperature, ionic strength, etc.). Nucleic acid hybridization may occur between DNA-DNA, as well as between DNA-RNA or RNA-RNA, as long as they have complementary sequences for base pairing. With respect to the further detailed description of nucleic acid hybridization, please refer to, for example, Henegariu O et al., (1999). "Custom fluorescent-nucleotide synthesis as an alternative method for nucleic acid labeling", Nature Biotechnology 18:345-348; Ezaki T et al., 1989. Fluorometric Deoxyribonucleic Acid-Deoxyribonucleic Acid Hybridization in Microdilution Wells as an Alternative to Membrane Filter Hybridization in which Radioisotopes Are Used to Determine Genetic Relatedness among Bacterial Strains. Int. J. of Systemic Bacteriology 29 (3): 224-229; and Herrington C et al., 1998. PCR 3: PCR in situ hybridization: a practical approach, Volume 3. Oxford: Oxford University Press.

In order to ensure the specificity of nucleic acid hybridization, a stringent condition or a high stringent condition is generally used. Stringent conditions and high stringent conditions are well known in the field of molecular biology. For example, a stringent condition may refer to hybridization in 6× sodium chloride/sodium citrate (SSC), at about 45° C., followed by washing in 0.2×SSC/0.1% SDS, at about 50-65° C. for one or more times. A high stringent condition may refer to hybridization in 6×SSC at about 45° C., followed by washing in 0.1×SSC/0.2% SDS, at about 68° C. for one or more times. With respect to the other stringent conditions or high stringent conditions known by a person skilled in the art, please refer to, example, Ausubel, F. M. et al. (ed.), 1989, Current Protocols in Molecular Biology, Vol. 1, Green Publishing Associates, Inc., and John Wiley & Sons, Inc., New York, pages 6.3.1-6.3.6 and 2.10.3.

As used herein, the term "linker" refers to a short peptide for linking two molecules (e.g., proteins). Such linkers are well known by a person skilled in the art, including, but not limited to a flexible linker, such as $(Gly)_4$, $(Gly)_4$-Ser, and $((Gly)_4\text{-Ser})_3$.

In the invention, the terms "polypeptide" and "protein" have the same meanings, which can be used interchangeably. Moreover, in the invention, amino acids are generally expressed as one-letter codes and three-letter codes. For example, alanine may be expressed as A or Ala.

As used herein, the term "restriction enzyme cleavage site" refers to an enzyme cleavage site recognized by a restriction enzyme. Such restriction enzyme cleavage sites are well known by a person skilled in the art, including, but not limited to the enzyme cleavage sites recognized by restriction enzymes such as EcoR I, BamH I, Hind II, Hind III, Hpa I, Hpa II, Mbo I, and Mbo II.

As used herein, the term "antigenic epitope", "antigen epitope" and "epitope" refer to a part on an antigen that is specifically bound by an immunoglobulin or antibody. "Epitope" is also called "antigenic determinant" in the art. An epitope or antigenic determinant generally consists of chemically active surface groups of a molecule, such as amino acids, carbohydrates or saccharide sidechains, and generally has a specific 3D structural characteristic and a specific charge characteristic. For example, an epitope generally comprises at least 3, 4, 5, 6, 7, 8, 9, 10, 11, 12, 13, 14 or 15 contiguous or non-contiguous amino acids in its unique conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are linearly present along the primary amino acid sequence of the protein. In a conformational epitope, the interaction sites are spaced from each other by amino acid residues of the protein.

As used herein, the term "HBsAg epitope" refers to a part on HBsAg that can be specifically bound by an immunoglobulin or antibody. The structure and function of HBsAg of human HBV have been well studied. Moreover, many papers have reported the epitopes on HBsAg of human HBV. See, for example, WO 97/39029 A2; WO 85/04103 A1; Xiaoxing Qiu et al., The Journal of Immunology, 1996, Vol. 156, pages 3350-3356; WO 2013/185558 A1, etc.

As used herein, the term "epitope peptide" refers to a peptide fragment on an antigen that can form an epitope or act as an epitope. Under some conditions, an epitope peptide alone can be specifically recognized/bound by an antibody against the epitope. Under some other conditions, an epitope peptide has to be fused to a polypeptide carrier to facilitate the epitope peptide to be specifically recognized by an antibody. The epitope comprised in an epitope peptide may be a linear epitope, or a conformational epitope. When an epitope peptide comprises a linear epitope, it may comprise or is a contiguous amino acid segment (i.e., a peptide fragment) forming the epitope in an antigen. When an epitope peptide comprises a conformational epitope, it may comprise or is a contiguous amino acid segment (i.e., a peptide fragment) covering all the amino acid residues involved in the conformational epitope. In some embodiments of the invention, an epitope peptide preferably has a length of no more than 500 amino acid residues, for example, a length of no more than 400 amino acid residues, a length of no more than 300 amino acid residues, a length of no more than 200 amino acid residues, a length of no more than 100 amino acid residues, a length of no more than 90 amino acid residues, a length of no more than 80 amino acid residues, a length of no more than 70 amino acid residues, a length of no more than 60 amino acid residues, a length of no more than 50 amino acid residues, a length of no more than 40 amino acid residues, a length of no more than 30 amino acid residues, or a length of no more than 25 amino acid residues.

As used herein, the term "polypeptide carrier" refers to such a carrier protein that may act as a carrier of an epitope peptide, i.e., may have the epitope peptide inserted at a specific position (for example, within the protein, or at N-terminus or C-terminus of the protein) therein, so that the epitope peptide can be presented and thus can be recognized by an antibody or immune system. Such carrier proteins have been reported in the previous papers, including, for example, HPV L1 protein (into which the epitope peptide may be inserted between the amino acids from positions 130 to 131 or between the amino acids from positions 426 to 427 of the protein; see Slupetzky, K. et al., Chimeric papillomavirus-like particles expressing a foreign epitope on capsid surface loops[J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16[J]. J Virol, 2003, 77: 8386-8393), CRM197 protein (the epitope peptide may be linked to the N-terminus or C-terminus of the protein or a fragment thereof), and so on. As discussed above, the invention provides a new class of polypeptide carriers for presenting target polypeptides, which are particularly suitable for presenting an epitope peptide comprising an antigenic epitope from human hepatitis B virus (e.g., an epitope of HBsAg from human HBV). In an embodiment of the invention, a linker (e.g., a flexible or rigid linker) may be used between an epitope peptide and a polypeptide carrier, to promote their folding, respectively.

As used herein, the term "recombinant protein" only means that the protein described is not a naturally occurring protein, and is not intended to restrict the means of producing or obtaining the protein. The recombinant protein of the invention may be produced by any known methods, including, but not limited to, genetic engineering methods and artificial synthesis methods.

As used herein, the term "virus-like particle" refers to a hollow particle formed by one or more structural proteins of a certain virus, which does not comprise viral nucleic acid, cannot be self-replicated, but is the same as or similar to a true virion in terms of morphology and structure.

As used herein, the term "a pharmaceutically acceptable carrier and/or excipient" refers to a carrier and/or excipient that is pharmacologically and/or physiologically compatible to a subject and active ingredients, which is well known in the art (see, e.g., Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, non-ionic surfactants (e.g., Tween-80); and ionic strength enhancers include, but are not limited to, NaCl.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), cornea bacterium parvum, lipopolysaccharide, cytokines, and the like. Freund's adjuvant is the most commonly used adjuvant in animal experiments currently. Aluminum hydroxide adjuvant is used in clinical trials more commonly.

As used herein, the term "*E. coli* expression system" refers to an expression system consisting of *E. coli* (strains) and a vector, wherein the *E. coli* (strains) include, but are not limited to: GI698, ER2566, BL21 (DE3), B834 (DE3), and BLR (DE3), which are available on the market.

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as a vector, include, but are not limited to, retrovirus (including lentivirus), adenovirus, adeno-associated virus, herpes virus (such as herpes simplex virus), pox virus, baculovirus, papillomavirus, and papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, a prokaryotic cell such as *E. coli* or *Bacillus subtilis*, a fungal cell such as yeast cell or *Aspergillus*, an insect cell such as S2 *Drosophila* cell or Sf9, and an animal cell such as fibroblast, CHO cell, COS cell, NSO cell, HeLa cell, BHK cell, HEK 293 cell or human cell.

As used herein, the term "subject" refers to a mammal, for example, a primate mammal, such as human.

As used herein, the term "an effective amount" refers to an amount that is sufficient to achieve or at least partially achieve a desired effect. For example, an effective amount for preventing a disease (e.g., HBV infection, or a disease associated with HBV infection) refers to an amount that is sufficient to prevent, suppress or delay the development of the disease (e.g., HBV infection, or a disease associated with HBV infection); a therapeutically effective amount refers to an amount that is sufficient to cure or at least partially suppress a disease and its complications in a patient with the disease. Determination of such an effective amount is completely within the ability of a person skilled in the art. For example, an amount effective for a therapeutic use depends on the severity degree of a disease to be treated, general state of the immune system in a patient, general conditions of a patient, such as age, body weight and gender, administration routes of drugs, additional therapies used simultaneously, and the like.

BENEFICIAL EFFECTS OF THE INVENTION

The technical solutions of the invention have the following beneficial effects over the prior art:

(1) The invention provides a new polypeptide carrier, which has a broad applicability, can be used to efficiently present various target polypeptides (e.g., antigen epitopes/antigen peptide fragments), and induce generation of a specific immune response to a target polypeptide in a host. Such a target polypeptide (e.g., an antigenic epitope/antigen peptide fragment) includes, but is not limited to, an antigenic epitope/antigen peptide fragment from HIV (e.g., an antigenic epitope/antigen peptide fragment from HIV GP120 protein; for example, a polypeptide comprising the amino acids from positions 361-375 of GP120 protein), an antigenic epitope/antigen peptide fragment from human PD-L1 protein (e.g., a polypeptide comprising amino acids from positions 147-160 of human PD-L1 protein), and an antigenic epitope/antigen peptide fragment from human HBV (e.g., an antigenic epitope/antigen peptide fragment of HBsAg protein from human HBV; e.g., a polypeptide comprising the amino acids from positions 113-135 of HBsAg protein).

(2) The polypeptide carriers of the invention are particularly suitable for presenting antigen epitopes from human hepatitis B virus (e.g., epitopes in HBsAg from human HBV), are able to induce a very strong and specific immune response for cleaning HBsAg in a subject, with an efficacy significantly better than that of the existing hepatitis B vaccines (e.g., vaccines comprising the same epitope and constructed by using HBcAg of human HBV as a polypeptide carrier).

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantageous aspects of the invention are obvious for a person skilled in the art.

DESCRIPTION OF THE DRAWINGS

FIG. 3A: the target polypeptide used was SEQ ID NO: 20, and the titer of anti-GP120 antibodies was determined; FIG. 3B: the target polypeptide used was SEQ ID NO: 21, and the titer of anti-PD-L1 antibodies was determined; FIG. 3C: the target polypeptide used was SEQ ID NO: 22, and the titer of anti-HBsAg antibodies was determined.

SEQUENCE INFORMATION

Figure 1:
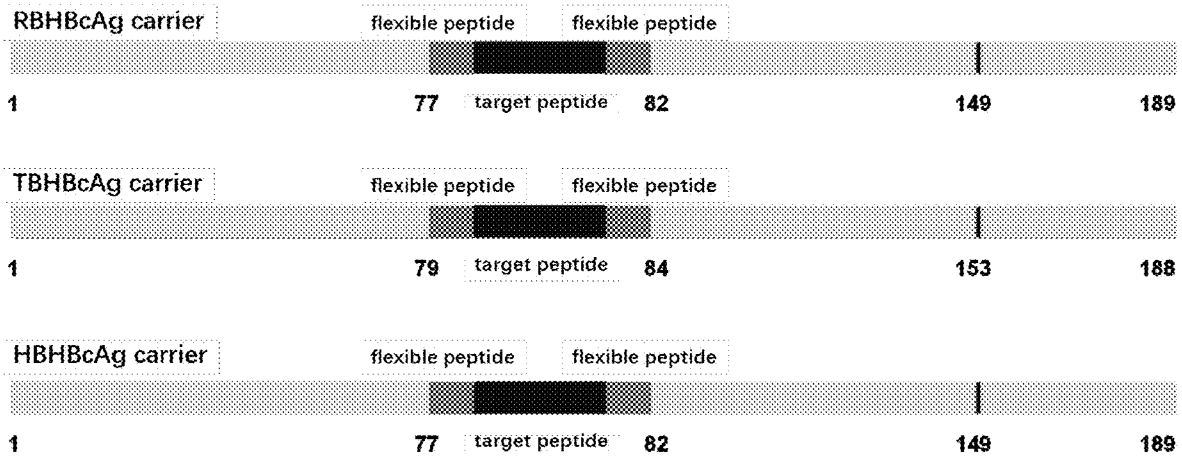
FIG. 1 shows a scheme of cloning solutions in which recombinant proteins are constructed by inserting a target polypeptide (a target antigen peptide fragment) into RBHBcAg carrier, TBHBcAg carrier and HBHBcAg carrier of the invention.

Information on a part of sequences (SEQ ID NO: 1-44) involved in the invention is provided in the following Table 1.

TABLE 1

Sequence information of SEQ ID NO: 1-44

| SEQ ID NO | Name | Sequence information |
|---|---|---|
| 1 | RBHBcAg | MDIDPYKEFGASSQLISFLPEDFFPNLAELVETTTALYEEELVGKEHCSPHHTALR<br>SLLNCWGETVRLITWVRNSVEGPLIQDAIVQQVQASVGLRMRQLMWFHLSCLTFGQ<br>PTVIEFLVSFGTWIRTPQAYRPPNAPILSTLPEHTIVRRRGGSRATRSPRRRTPSP<br>RRRRSQSPRRRRSQSPASSNC |
| 2 | TBHBcAg | MENLERLDIYKEFGVSDVLVSFLPDDFFPTLQQLLESVNALYEDELTGPNHCSPHH<br>TALRHLIMCGVELRDFIDWMHEQGLSPDADALLAGYLRSKYLKHITKAIWYHLSCL<br>TFGKQTVHEYLVSFGTWIRTPAAYRPVNAPILTTLPETSVIRRRPASRRSTPSPRR<br>RRSQSPRRRRSPSPRPASNC |
| 3 | HBHBcAg | MDIDPYKEFGASSQLVSFLPADFFPALNDLVETSVALYEEDLVGKEHCSPHHAALR<br>ALLNCWEETVRLITWVRATVEGQPVQDAIIGYVQTTVGLRMRQQIWFHLSCLTFGQ<br>QTVIEFLVSFGTWMRTPAAYRPPNAPILSTLPEHTVIRRRGNPRAPRSPRRRTPSP<br>RRRRSQSPRRRRSQSPAPSNC |
| 4 | RBHBcAg189 | MDIDPYKEFGASSQLISFLPEDFFPNLAELVETTTALYEEELVGKEHCSPHHTALR<br>SLLNCWGETVRLITWVRNSVEGGGGGSGGGGTGSEFGGGGSGGGGSQDAIVQQVQA<br>SVGLRMRQLMWFHLSCLTFGQPTVIEFLVSFGTWIRTPQAYRPPNAPILSTLPEHT<br>IVRRRGGSRATRSPRRRTPSPRRRRSQSPRRRRSQSPASSNC |
| 5 | RBHBcAg149 | MDIDPYKEFGASSQLISFLPEDFFPNLAELVETTTALYEEELVGKEHCSPHHTALR<br>SLLNCWGETVRLITWVRNSVEGGGGGSGGGGTGSEFGGGGSGGGGSQDAIVQQVQA<br>SVGLRMRQLMWFHLSCLTFGQPTVIEFLVSFGTWIRTPQAYRPPNAPILSTLPEHT<br>IV |
| 6 | TBHBcAg188 | MENLERLDIYKEFGVSDVLVSFLPDDFFPTLQQLLESVNALYEDELTGPNHCSPHH<br>TALRHLIMCGVELRDFIDWMHEQGGGGGSGGGGTGSEFGGGGSGGGGSDADALLAG<br>YLRSKYLKHITKAIWYHLSCLTFGKQTVHEYLVSFGTWIRTPAAYRPVNAPILTTL<br>PETSVIRRRPASRRSTPSPRRRRSQSPRRRRSPSPRPASNC |
| 7 | TBHBcAg153 | MENLERLDIYKEFGVSDVLVSFLPDDFFPTLQQLLESVNALYEDELTGPNHCSPHH<br>TALRHLIMCGVELRDFIDWMHEQGGGGGSGGGGTGSEFGGGGSGGGGSDADALLAG<br>YLRSKYLKHITKAIWYHLSCLTFGKQTVHEYLVSFGTWIRTPAAYRPVNAPILTTL<br>PETSVI |
| 8 | HBHBcAg189 | MDIDPYKEFGASSQLVSFLPADFFPALNDLVETSVALYEEDLVGKEHCSPHHAALR<br>ALLNCWEETVRLITWVRATVEGGGGGSGGGGTGSEFGGGGSGGGGSQDAIIGYVQT<br>TVGLRMRQQIWFHLSCLTFGQQTVIEFLVSFGTWMRTPAAYRPPNAPILSTLPEHT<br>VIRRRGNPRAPRSPRRRTPSPRRRRSQSPRRRRSQSPAPSNC |
| 9 | HBHBcAg149 | MDIDPYKEFGASSQLVSFLPADFFPALNDLVETSVALYEEDLVGKEHCSPHHAALR<br>ALLNCWEETVRLITWVRATVEGGGGGSGGGGTGSEFGGGGSGGGGSQDAIIGYVQT<br>TVGLRMRQQIWFHLSCLTFGQQTVIEFLVSFGTWMRTPAAYRPPNAPILSTLPEHT<br>VI |
| 10 | HBcAg183 | MDIDPYKEFGASVELLSFLPSDFFPSIRDLLDTASALYREALESPEHCSPHHTALR<br>QAILCWGELMNLATWVGSNLEDGGGGSGGGGTGSEFGGGGSGGGGSRELVVSYVNV<br>NMGLKIRQLLWFHISCLTFGRETVLEYLVSFGVWIRTPPAYRPQNAPILSTLPETT<br>VVRRRGRSPRRRTPSPRRRRSQSPRRRRSQSRESQC |
| 11 | HBcAg149 | MDIDPYKEFGASVELLSFLPSDFFPSIRDLLDTASALYREALESPEHCSPHHTALR<br>QAILCWGELMNLATWVGSNLEDGGGGSGGGGTGSEFGGGGSGGGGSRELVVSYVNV<br>NMGLKIRQLLWFHISCLTFGRETVLEYLVSFGVWIRTPPAYRPQNAPILSTLPETT<br>VV |
| 12 | RBHBcAg189 | ATGGACATTGATCCTTATAAAGAATTTGGAGCTTCATCTCAACTGATCTCTTTCTT<br>GCCTGAGGACTTTTTCCCAAACCTTGCAGAATTGGTCGAGACCACCACAGCTCTCT<br>ATGAAGAAGAATTAGTAGGTAAGGAGCATTGCTCCCCTCACCATACTGCTTTACGA<br>TCCTTGCTAAATTGCTGGGGAGAGACTGTTAGATTAATAACTTGGGTCAGGAACTC<br>TGTGGAGGGAGGTGGAGGTGGTTCTGGAGGTGGTGGTACTGGATCCGAATTCGGTG<br>GTGGAGGTTCAGGAGGAGGTGGTTCCCAAGATGCCATTGTCCAGCAAGTTCAGGCC<br>TCGGTGGGCCTGCGCATGAGACAGTTAATGTGGTTCCATCTCTCATGCCTAACATT<br>TGGACAGCCCACTGTCATAGAATTTCTGGTCTCTTTTGGAACATGGATCAGAACCC |

TABLE 1-continued

Sequence information of SEQ ID NO: 1-44

| SEQ ID NO | Name | Sequence information |
|---|---|---|
| | | CGCAAGCTTACAGACCCCCTAATGCACCCATTCTCTCGACTCTTCCGGAGCATACA<br>ATCGTTAGGAGAAGAGGAGGTTCACGCGCTACTAGGTCCCCCCGAAGGCGCACTCC<br>CTCTCCTCGCCGACGCAGATCTCAATCGCCGCGTCGCCGCAGATCTCAGTCTCCAG<br>CTTCCTCCAACTGCTAA |
| 13 | RBHBcAg149 | ATGGACATTGATCCTTATAAAGAATTTGGAGCTTCATCTCAACTGATCTCTTTCTT<br>GCCTGAGGACTTTTTCCCAAACCTTGCAGAATTGGTCGAGACCACCACAGCTCTCT<br>ATGAAGAAGAATTAGTAGGTAAGGAGCATTGCTCCCCTCACCATACTGCTTTACGA<br>TCCTTGCTAAATTGCTGGGGAGAGACTGTTAGATTAATAACTTGGGTCAGGAACTC<br>TGTGGAGGGAGGTGGAGGTGGTTCTGGAGGTGGTGGTACTGGATCCGAATTCGGTG<br>GTGGAGGTTCAGGAGGAGGTGGTTCCCAAGATGCCATTGTCCAGCAAGTTCAGGCC<br>TCGGTGGGCCTGCGCATGAGACAGTTAATGTGGTTCCATCTCTCATGCCTAACATT<br>TGGACAGCCCACTGTCATAGAATTTCTGGTCTCTTTTGGAACATGGATCAGAACCC<br>CGCAAGCTTACAGACCCCCTAATGCACCCATTCTCTCGACTCTTCCGGAGCATACA<br>ATCGTT |
| 14 | TBHBcAg188 | ATGGAAAACCTTGAAAGACTTGACATCTATAAAGAATTTGGAGTCTCTGATGTCTT<br>GGTGTCTTTCTTACCTGATGATTTCTTTCCAACTTTACAGCAACTTTTGGAATCAG<br>TGAATGCCCTATATGAGGATGAACTCACTGGGCCTAATCACTGTTCTCCCCATCAT<br>ACTGCCTTAAGGCACTTGATTATGTGTGGGGTAGAATTAAGAGATTTTATTGATTG<br>GATGCATGAACAGGGGGGTGGAGGTGGTTCTGGAGGTGGTGGTACTGGATCCGAAT<br>TCGGTGGTGGAGGTTCAGGAGGAGGTGGTTCCGATGCAGACGCTCTTTTGGCTGGT<br>TACCTTCGATCCAAATATCTTAAACATATTACCAAGGCTATTTGGTATCATTTAAG<br>CTGTTTGACCTTTGGTAAGCAAACAGTGCATGAATACCTGGTATCCTTTGGCACCT<br>GGATCAGAACCCCAGCTGCATATAGACCAGTGAATGCACCCATTCTCACCACTCTT<br>CCGGAAACTTCAGTTATCAGAAGAAGGCCTGCCTCCAGAAGATCTACTCCCTCTCC<br>TCGCAGACGCCGATCTCAATCACCGCGCCGCCGCCGCTCTCCATCTCCAAGACCAG<br>CAAGCAATTGCTGA |
| 15 | TBHBcAg153 | ATGGAAAACCTTGAAAGACTTGACATCTATAAAGAATTTGGAGTCTCTGATGTCTT<br>GGTGTCTTTCTTACCTGATGATTTCTTTCCAACTTTACAGCAACTTTTGGAATCAG<br>TGAATGCCCTATATGAGGATGAACTCACTGGGCCTAATCACTGTTCTCCCCATCAT<br>ACTGCCTTAAGGCACTTGATTATGTGTGGGGTAGAATTAAGAGATTTTATTGATTG<br>GATGCATGAACAGGGGGGTGGAGGTGGTTCTGGAGGTGGTGGTACTGGATCCGAAT<br>TCGGTGGTGGAGGTTCAGGAGGAGGTGGTTCCGATGCAGACGCTCTTTTGGCTGGT<br>TACCTTCGATCCAAATATCTTAAACATATTACCAAGGCTATTTGGTATCATTTAAG<br>CTGTTTGACCTTTGGTAAGCAAACAGTGCATGAATACCTGGTATCCTTTGGCACCT<br>GGATCAGAACCCCAGCTGCATATAGACCAGTGAATGCACCCATTCTCACCACTCTT<br>CCGGAAACTTCAGTTATC |
| 16 | HBHBcAg189 | ATGGACATTGATCCTTATAAAGAGTTCGGTGCTTCATCTCAACTTGTCTCCTTTTT<br>GCCTGCTGACTTCTTTCCCGCCTTGAACGACCTGGTGGAAACTTCGGTGGCCTTAT<br>ATGAGGAAGACCTTGTAGGTAAGGAGCATTGCTCCCCTCATCATGCAGCCTTAAGG<br>GCCCTACTTAATTGCTGGGAGGAAACAGTCAGACTGATTACCTGGGTCCGTGCCAC<br>AGTAGAGGGAGGTGGAGGTGGTTCTGGAGGTGGTGGTACTGGATCCGAATTCGGTG<br>GTGGAGGTTCAGGAGGAGGTGGTTCCCAGGATGCCATCATCGGTTATGTCCAGACT<br>ACGGTGGGCCTACGCATGAGACAACAGATCTGGTTCCATCTCTCATGCCTTACTTT<br>TGGGCAGCAGACTGTGATAGAGTTCCTGGTCTCATTTGGGACATGGATGAGAACTC<br>CAGCCGCCTATAGACCCCCCAATGCACCCATTTTATCAACTCTTCCAGAGCACACA<br>GTCATTAGGAGAAGAGGAAATCCGCGTGCTCCTAGGTCCCCCAGAAGGCGCACTCC<br>CTCTCCTCGCCGACGCAGATCTCAATCTCCGCGTCGCCGGAGATCTCAATCTCCAG<br>CTCCCTCCAACTGCTAA |
| 17 | HBHBcAg149 | ATGGACATTGATCCTTATAAAGAGTTCGGTGCTTCATCTCAACTTGTCTCCTTTTT<br>GCCTGCTGACTTCTTTCCCGCCTTGAACGACCTGGTGGAAACTTCGGTGGCCTTAT<br>ATGAGGAAGACCTTGTAGGTAAGGAGCATTGCTCCCCTCATCATGCAGCCTTAAGG<br>GCCCTACTTAATTGCTGGGAGGAAACAGTCAGACTGATTACCTGGGTCCGTGCCAC<br>AGTAGAGGGAGGTGGAGGTGGTTCTGGAGGTGGTGGTACTGGATCCGAATTCGGTG<br>GTGGAGGTTCAGGAGGAGGTGGTTCCCAGGATGCCATCATCGGTTATGTCCAGACT<br>ACGGTGGGCCTACGCATGAGACAACAGATCTGGTTCCATCTCTCATGCCTTACTTT<br>TGGGCAGCAGACTGTGATAGAGTTCCTGGTCTCATTTGGGACATGGATGAGAACTC<br>CAGCCGCCTATAGACCCCCCAATGCACCCATTTTATCAACTCTTCCAGAGCACACA<br>GTCATT |
| 18 | HBcAg183 | ATGGACATTGATCCATATAAAGAATTTGGAGCTTCTGTGGAGTTACTCTCTTTTTT<br>GCCTTCCGACTTCTTTCCTTCTATCCGAGATCTCCTCGACACCGCCTCTGCTCTGT<br>ATCGGGAGGCCTTAGAGTCTCCGGAACATTGTTCACCTCACCATACGGCACTCAGG<br>CAAGCTATTCTGTGTTGGGGTGAGTTGATGAATCTAGCCACCTGGGTGGGAAGTAA<br>TTTGGAAGATGGTGGAGGTGGTTCTGGAGGTGGTGGTACTGGATCCGAATTCGGTG<br>GTGGAGGTTCAGGAGGAGGTGGTTCCAGGGAACTAGTAGTCAGCTATGTCAACGTT<br>AATATGGGCCTAAAAATCAGACAACTATTGTGGTTTCACATTTCCTGTCTTACTTT<br>TGGGAGAGAAACTGTTCTTGAATATTTGGTGTCTTTTGGAGTGTGGATTCGCACTC<br>CTCCTGCATATAGACCACAAAATGCCCCTATCTTATCAACACTTCCGGAAACTACT<br>GTTGTTCGTCGCCGAGGCCGTAGCCCGCGACGACGTACCCCGAGCCCGCGTCGACG<br>TCGCAGCCAGAGCCCGCGCCGTCGTCGCAGCCAGAGCCGTGAAAGCCAGTGCTAA |

TABLE 1-continued

Sequence information of SEQ ID NO: 1-44

| SEQ ID NO | Name | Sequence information |
| --- | --- | --- |
| 19 | HBcAg149 | ATGGACATTGATCCATATAAAGAATTTGGAGCTTCTGTGGAGTTACTCTCTTTTTT GCCTTCCGACTTCTTTCCTTCTATCCGAGATCTCCTCGACACCGCCTCTGCTCTGT ATCGGGAGGCCTTAGAGTCTCCGGAACATTGTTCACCTCACCATACGGCACTCAGG CAAGCTATTCTGTGTTGGGGTGAGTTGATGAATCTAGCCACCTGGGTGGGAAGTAA TTTGGAAGATGGTGGAGGTGGTTCTGGAGGTGGTGGTACTGGATCCGAATTCGGTG GTGGAGGTTCAGGAGGAGGTGGTTCCAGGGAACTAGTAGTCAGCTATGTCAACGTT AATATGGGCCTAAAAATCAGACAACTATTGTGGTTTCACATTTCCTGTCTTACTTT TGGGAGAGAAACTGTTCTTGAATATTTGGTGTCTTTTGGAGTGTGGATTCGCACTC CTCCTGCATATAGACCACAAAATGCCCCTATCTTATCAACACTTCCGGAAACTACT GTTGTT |
| 20 | HIV-GP120-aa 361-375 | FKQSSGGDPEIVTHS |
| 21 | hPDL1-aa147-160 | TSEHELTCQAEGYP |
| 22 | HBsAg-aa113-135 | SSTTSTGPCKTCTTPAQGTSMFP |
| 23 | RBHBcAg189-SEQ20 | MDIDPYKEFGASSQLISFLPEDFFPNLAELVETTTALYEEELVGKEHCSPHHTALR SLLNCWGETVRLITWVRNSVEGGGGGSGGGGTGSFKQSSGGDPEIVTHSEFGGGGS GGGGSQDAIVQQVQASVGLRMRQLMWFHLSCLTFGQPTVIEFLVSFGTWIRTPQAY RPPNAPILSTLPEHTIVRRRGGSRATRSPRRRTPSPRRRRSQSPRRRRSQSPASSN C |
| 24 | RBHBcAg149-SEQ20 | MDIDPYKEFGASSQLISFLPEDFFPNLAELVETTTALYEEELVGKEHCSPHHTALR SLLNCWGETVRLITWVRNSVEGGGGGSGGGGTGSFKQSSGGDPEIVTHSEFGGGGS GGGGSQDAIVQQVQASVGLRMRQLMWFHLSCLTFGQPTVIEFLVSFGTWIRTPQAY RPPNAPILSTLPEHTIV |
| 25 | TBHBcAg188-SEQ20 | MENLERLDIYKEFGVSDVLVSFLPDDFFPTLQQLLESVNALYEDELTGPNHCSPHH TALRHLIMCGVELRDFIDWMHEQGGGGGSGGGGTGSFKQSSGGDPEIVTHSEFGGG GSGGGGSDADALLAGYLRSKYLKHITKAIWYHLSCLTFGKQTVHEYLVSFGTWIRT PAAYRPVNAPILTTLPETSVIRRRPASRRSTPSPRRRRSQSPRRRRSPSPRPASNC |
| 26 | TBHBcAg153-SEQ20 | MENLERLDIYKEFGVSDVLVSFLPDDFFPTLQQLLESVNALYEDELTGPNHCSPHH TALRHLIMCGVELRDFIDWMHEQGGGGGSGGGGTGSFKQSSGGDPEIVTHSEFGGG GSGGGGSDADALLAGYLRSKYLKHITKAIWYHLSCLTFGKQTVHEYLVSFGTWIRT PAAYRPVNAPILTTLPETSVI |
| 27 | HBHBcAg189-SEQ20 | MDIDPYKEFGASSQLVSFLPADFFPALNDLVETSVALYEEDLVGKEHCSPHHAALR ALLNCWEETVRLITWVRATVEGGGGGSGGGGTGSFKQSSGGDPEIVTHSEFGGGGS GGGGSQDAIIGYVQTTVGLRMRQQIWFHLSCLTFGQQTVIEFLVSFGTWMRTPAAY RPPNAPILSTLPEHTVIRRRGNPRAPRSPRRRTPSPRRRRSQSPRRRRSQSPAPSN C |
| 28 | HBHBcAg149-SEQ20 | MDIDPYKEFGASSQLVSFLPADFFPALNDLVETSVALYEEDLVGKEHCSPHHAALR ALLNCWEETVRLITWVRATVEGGGGGSGGGGTGSFKQSSGGDPEIVTHSEFGGGGS GGGGSQDAIIGYVQTTVGLRMRQQIWFHLSCLTFGQQTVIEFLVSFGTWMRTPAAY RPPNAPILSTLPEHTVI |
| 29 | RBHBcAg189-SEQ21 | MDIDPYKEFGASSQLISFLPEDFFPNLAELVETTTALYEEELVGKEHCSPHHTALR SLLNCWGETVRLITWVRNSVEGGGGGSGGGGTGSTSEHELTCQAEGYPEFGGGGSG GGGSQDAIVQQVQASVGLRMRQLMWFHLSCLTFGQPTVIEFLVSFGTWIRTPQAYR PPNAPILSTLPEHTIVRRRGGSRATRSPRRRTPSPRRRRSQSPRRRRSQSPASSNC |
| 30 | RBHBcAg149-SEQ21 | MDIDPYKEFGASSQLISFLPEDFFPNLAELVETTTALYEEELVGKEHCSPHHTALR SLLNCWGETVRLITWVRNSVEGGGGGSGGGGTGSTSEHELTCQAEGYPEFGGGGSG GGGSQDAIVQQVQASVGLRMRQLMWFHLSCLTFGQPTVIEFLVSFGTWIRTPQAYR PPNAPILSTLPEHTIV |
| 31 | TBHBcAg188-SEQ21 | MENLERLDIYKEFGVSDVLVSFLPDDFFPTLQQLLESVNALYEDELTGPNHCSPHH TALRHLIMCGVELRDFIDWMHEQGGGGGSGGGGTGSTSEHELTCQAEGYPEFGGGG SGGGGSDADALLAGYLRSKYLKHITKAIWYHLSCLTFGKQTVHEYLVSFGTWIRTP AAYRPVNAPILTTLPETSVIRRRPASRRSTPSPRRRRSQSPRRRRSPSPRPASNC |
| 32 | TBHBcAg153-SEQ21 | MENLERLDIYKEFGVSDVLVSFLPDDFFPTLQQLLESVNALYEDELTGPNHCSPHH TALRHLIMCGVELRDFIDWMHEQGGGGGSGGGGTGSTSEHELTCQAEGYPEFGGGG SGGGGSDADALLAGYLRSKYLKHITKAIWYHLSCLTFGKQTVHEYLVSFGTWIRTP AAYRPVNAPILTTLPETSVI |
| 33 | HBHBcAg189-SEQ21 | MDIDPYKEFGASSQLVSFLPADFFPALNDLVETSVALYEEDLVGKEHCSPHHAALR ALLNCWEETVRLITWVRATVEGGGGGSGGGGTGSTSEHELTCQAEGYPEFGGGGSG GGGSQDAIIGYVQTTVGLRMRQQIWFHLSCLTFGQQTVIEFLVSFGTWMRTPAAYR PPNAPILSTLPEHTVIRRRGNPRAPRSPRRRTPSPRRRRSQSPRRRRSQSPAPSNC |

TABLE 1-continued

Sequence information of SEQ ID NO: 1-44

| SEQ ID NO | Name | Sequence information |
|---|---|---|
| 34 | HBHBcAg149-SEQ21 | MDIDPYKEFGASSQLVSFLPADFFPALNDLVETSVALYEEDLVGKEHCSPHHAALRALLNCWEETVRLITWVRATVEGGGGGSGGGGTGSTSEHELTCQAEGYPEFGGGGSGGGGSQDAIIGYVQTTVGLRMRQQIWFHLSCLTFGQQTVIEFLVSFGTWMRTPAAYRPPNAPILSTLPEHTVI |
| 35 | RBHBcAg189-SEQ22 | MDIDPYKEFGASSQLISFLPEDFFPNLAELVETTTALYEEELVGKEHCSPHHTALRSLLNCWGETVRLITWVRNSVEGGGGGSGGGGTGSSSTTSTGPCKTCTTPAQGTSMFPEFGGGGSGGGGSQDAIVQQVQASVGLRMRQLMWFHLSCLTFGQPTVIEFLVSFGTWIRTPQAYRPPNAPILSTLPEHTIVRRRGGSRATRSPRRRTPSPRRRRSQSPRRRRSQSPASSNC |
| 36 | RBHBcAg149-SEQ22 | MDIDPYKEFGASSQLISFLPEDFFPNLAELVETTTALYEEELVGKEHCSPHHTALRSLLNCWGETVRLITWVRNSVEGGGGGSGGGGTGSSSTTSTGPCKTCTTPAQGTSMFPEFGGGGSGGGGSQDAIVQQVQASVGLRMRQLMWFHLSCLTFGQPTVIEFLVSFGTWIRTPQAYRPPNAPILSTLPEHTIV |
| 37 | TBHBcAg188-SEQ22 | MENLERLDIYKEFGVSDVLVSFLPDDFFPTLQQLLESVNALYEDELTGPNHCSPHHTALRHLIMCGVELRDFIDWMHEQGGGGGSGGGGTGSSSTTSTGPCKTCTTPAQGTSMFPEFGGGGSGGGGSDADALLAGYLRSKYLKHITKAIWYHLSCLTFGKQTVHEYLVSFGTWIRTPAAYRPVNAPILTTLPETSVIRRRPASRRSTPSPRRRRSQSPRRRRSPSPRPASNC |
| 38 | TBHBcAg153-SEQ22 | MENLERLDIYKEFGVSDVLVSFLPDDFFPTLQQLLESVNALYEDELTGPNHCSPHHTALRHLIMCGVELRDFIDWMHEQGGGGGSGGGGTGSSSTTSTGPCKTCTTPAQGTSMFPEFGGGGSGGGGSDADALLAGYLRSKYLKHITKAIWYHLSCLTFGKQTVHEYLVSFGTWIRTPAAYRPVNAPILTTLPETSVI |
| 39 | HBHBcAg189-SEQ22 | MDIDPYKEFGASSQLVSFLPADFFPALNDLVETSVALYEEDLVGKEHCSPHHAALRALLNCWEETVRLITWVRATVEGGGGGSGGGGTGSSSTTSTGPCKTCTTPAQGTSMFPEFGGGGSGGGGSQDAIIGYVQTTVGLRMRQQIWFHLSCLTFGQQTVIEFLVSFGTWMRTPAAYRPPNAPILSTLPEHTVIRRRGNPRAPRSPRRRTPSPRRRRSQSPRRRRSQSPAPSNC |
| 40 | HBHBcAg149-SEQ22 | MDIDPYKEFGASSQLVSFLPADFFPALNDLVETSVALYEEDLVGKEHCSPHHAALRALLNCWEETVRLITWVRATVEGGGGGSGGGGTGSSSTTSTGPCKTCTTPAQGTSMFPEFGGGGSGGGGSQDAIIGYVQTTVGLRMRQQIWFHLSCLTFGQQTVIEFLVSFGTWMRTPAAYRPPNAPILSTLPEHTVI |
| 41 | HBcAg183-SEQ22 | MDIDPYKEFGASVELLSFLPSDFFPSIRDLLDTASALYREALESPEHCSPHHTALRQAILCWGELMNLATWVGSNLEDGGGGSGGGGTGSSSTTSTGPCKTCTTPAQGTSMFPEFGGGGSGGGGSRELVVSYVNVNMGLKIRQLLWFHISCLTFGRETVLEYLVSFGVWIRTPPAYRPQNAPILSTLPETTVVRRRGRSPRRRTPSPRRRRSQSPRRRRSQSRESQC |
| 42 | HBcAg149-SEQ22 | MDIDPYKEFGASVELLSFLPSDFFPSIRDLLDTASALYREALESPEHCSPHHTALRQAILCWGELMNLATWVGSNLEDGGGGSGGGGTGSSSTTSTGPCKTCTTPAQGTSMFPEFGGGGSGGGGSRELVVSYVNVNMGLKIRQLLWFHISCLTFGRETVLEYLVSFGVWIRTPPAYRPQNAPILSTLPETTVV |
| 43 | Linker | GGGGGSGGGGTGSEFGGGGSGGGGS |
| 44 | HBsAg | MENIASGLLGPLLVLQAGFFLLTKILTIPQSLDSWWTSLNFLGGTPVCLGQNSQSQISSHSPTCCPPICPGYRWMCLRRFIIFLCILLLCLIFLLVLLDYQGMLPVCPLIPGSSTTSTGPCKTCTTPAQGTSMFPSCCCTKPTDGNCTCIPIPSSWAFAKYLWEWASVRFSWLSLLVPFVQWFVGLSPTVWLSVIWMMWFWGPSLYNILSPFMPLLPIFFCLWVYI |

Specific Modes for Carrying Out the Invention

The invention is illustrated by reference to the following examples (which are intended to describe the invention rather than limiting the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. Those skilled in the art understand that the examples are used for illustrating the present invention, but not intended to limit the protection scope of the present invention.

EXAMPLE 1

Construction of Plasmids Encoding Polypeptide Carriers

In the Example, plasmids encoding polypeptide carriers were constructed.

1.1 Preparation of Nucleotide Sequences Encoding Polypeptide Carriers

Based on three bat-derived HBV core antigens (i.e., RBHBcAg protein, TBHBcAg protein, and HBHBcAg protein), the following polypeptide carriers were designed:

RBHBcAg189 carrier, which differs from RBHBcAg protein (SEQ ID NO: 1) in that the amino acid residues from positions 78-81 of RBHBcAg protein are substituted with a linker set forth in SEQ ID NO: 43; the amino acid sequence of RBHBcAg189 carrier is set forth in SEQ ID NO: 4, and the nucleotide sequence of RBHBcAg189 carrier is set forth in SEQ ID NO: 12;

TBHBcAg188 carrier, which differs from TBHBcAg protein (SEQ ID NO: 2) in that the amino acid residues from positions 80-83 of RBHBcAg protein are substituted with a linker set forth in SEQ ID NO: 43; the amino acid sequence of TBHBcAg188 carrier is set forth in SEQ ID NO: 6, the nucleotide sequence of TBHBcAg188 carrier is set forth in SEQ ID NO: 14;

HBHBcAg189 carrier, which differs from HBHBcAg protein (SEQ ID NO: 3) in that the amino acid residues from positions 78-81 of RBHBcAg protein are substituted with a linker set forth in SEQ ID NO: 43; the amino acid sequence of HBHBcAg189 carrier is set forth in SEQ ID NO: 8, and the nucleotide sequence of HBHBcAg189 carrier is set forth in SEQ ID NO: 16.

In addition, based on HBcAg protein of human HBV, HBcAg183 carrier was also designed, as a control. HBcAg183 carrier differs from HBcAg protein of human HBV in that the amino acid residues from positions 79-81 of HBcAg protein of human HBV are substituted with a linker set forth in SEQ ID NO: 43; the amino acid sequence of HBcAg183 carrier is set forth in SEQ ID NO: 10, and the nucleotide sequence of HBcAg183 carrier is set forth in SEQ ID NO: 18.

With respect to the nucleotide sequences of said four carriers, their whole gene synthesis was performed by Sangon Biotech (Shanghai) Co., Ltd.

1.2 Preparation of Plasmids Encoding Polypeptide Carriers

By using the synthesized nucleotide sequences as templates, and using the primers in Table 2, the full-length genes and truncates (i.e., gene fragments truncated at C-terminus) of said 4 carriers were amplified by PCR, respectively. 8 PCR products were obtained, i.e., the gene encoding RBHBcAg189 carrier (SEQ ID NO: 12; the amino acid sequence encoded thereby is SEQ ID NO: 4), the gene encoding RBHBcAg149 carrier (SEQ ID NO: 13; the amino acid sequence encoded thereby is SEQ ID NO: 5), the gene encoding TBHBcAg188 carrier (SEQ ID NO: 14; the amino acid sequence encoded thereby is SEQ ID NO: 6), the gene encoding TBHBcAg153 (SEQ ID NO: 15; the amino acid sequence encoded thereby is SEQ ID NO: 7), the gene encoding HBHBcAg189 carrier (SEQ ID NO: 16; the amino acid sequence encoded thereby is SEQ ID NO: 8), the gene encoding HBHBcAg149 carrier (SEQ ID NO: 17; the amino acid sequence encoded thereby is SEQ ID NO: 9), the gene encoding HBcAg183 carrier (SEQ ID NO: 18; the amino acid sequence encoded thereby is SEQ ID NO: 10), and the gene encoding HBcAg149 carrier (SEQ ID NO: 19; the amino acid sequence encoded thereby is SEQ ID NO: 11).

pTO-T7 vector (Luo Wenxin, Zhang Jun, Yang Haijie, et al., Construction and Application of an *Escherichia coli* High Effective Expression Vector with an Enhancer [J], Chinese Journal of Biotechnology, 2000, 16(5): 578-581) was subjected to double enzyme digestion by NdeI and HindIII, to obtain a linear vector. By Gibson assembly cloning method (New England Biolabs (UK) Ltd), 8 PCR products obtained were ligated to the linear vector, and transformed into DH5a competent bacteria. The transformed bacteria were spread on a plate and cultured, monoclonal colonies were then selected, and the plasmids were extracted and sequenced. It was confirmed by sequencing that 8 plasmids comprising the nucleotide sequences encoding the polypeptide carriers were obtained.

The primers involved in the PCR are shown in Table 2.

TABLE 2

Primer sequences

| SEQ ID NO: | Primer name | Sequence |
|---|---|---|
| 45 | RBHBcAg149/189F | ACTTTAAGAAGGAGATATACATATGATGGACATTGATCCTTATAAAG |
| 46 | RBHBcAg149R | GTGGTGCTCGAGGCGGCCGCAAGCTTTTAAACGATTGTATGCTCCGGAAGAGTCGA |
| 47 | RBHBcAg189R | GTGGTGCTCGAGGCGGCCGCAAGCTTTTAGCAGTTGGAGGAAGCTGGAGACTGAGATCTGCGGCGAC |
| 48 | TBHBcAg153/188F | ACTTTAAGAAGGAGATATACATATGATGGAAAACCTTGAAAGACTTG |

TABLE 2-continued

| Primer sequences | | |
|---|---|---|
| SEQ ID NO: | Primer name | Sequence |
| 49 | TBHBcAg153R | GTGGTGCTCGAGGCGGCCGCAAGCTTTTAGATAACTGAAGTTTCCGGAAG AGTG |
| 50 | TBHBcAg188R | GTGGTGCTCGAGGCGGCCGCAAGCTTTTAGCAATTGCTTGCTGGTCTTG |
| 51 | HBHBcAg149/189F | ACTTTAAGAAGGAGATATACATATGATGGACATTGATCCTTATAAAG |
| 52 | HBHBcAg149R | GTGGTGCTCGAGGCGGCCGCAAGCTTTTAAATGACTGTGTGCTCTGGAAG AGTTGA |
| 53 | HBHBcAg189R | GTGGTGCTCGAGGCGGCCGCAAGCTTTTAGCAGTTGGAGGGAGCTGGAGA TTGAGATCTCCGGCGAC |

EXAMPLE 2

Preparation of Recombinant Proteins

In the Example, a nucleotide sequence encoding a target polypeptide was inserted into the plasmid constructed in Example 1, and a recombinant protein comprising the target polypeptide and the polypeptide carrier was obtained. The scheme of cloning solutions, in which recombinant proteins are constructed by inserting a target polypeptide (a target antigen peptide fragment) into RBHBcAg carrier, TBHBcAg carrier and HBHBcAg carrier of the invention, is shown in FIG. 1.

2.1 Construction of Expression Plasmids of Recombinant Proteins Comprising a Target Polypeptide and a Polypeptide Carrier In the Example, 3 target polypeptides were used to verify the versatility of the polypeptide carrier of the invention for presenting peptide fragments. Said 3 target polypeptides were: polypeptide HIV-GP120-aa361-375 (i.e., the amino acids from positions 361-375 of HIV GP120 protein, its amino acid sequence is set forth in SEQ ID NO: 20); polypeptide hPDL1-aa147-160 (i.e., the amino acids from positions 147-160 of human PD-L1 protein, its amino acid sequence is set forth in SEQ ID NO: 21); and polypeptide HBsAg-aa113-135 (i.e., the amino acids from positions 113-135 of hepatitis B surface antigen (HBsAg) from human HBV, its amino acid sequence is set forth in SEQ ID NO: 22).

The sense and antisense sequences coding said 3 target polypeptides (as shown in Table 3) were synthesized directly, and annealed, so as to obtain the gene fragments having cohesive end and encoding the target polypeptides.

The 6 plasmids (RBHBcAg189, RBHBcAg149, TBHBcAg188, TBHBcAg153, HBHBcAg189 and HBHBcAg149) obtained in Example 1 were subjected to double enzyme digestion by BamHI and EcoRI, to obtain 6 linear vectors. Then, the 3 gene fragments having cohesive end and encoding the target polypeptides, as prepared above, were ligated to the linear vectors, to obtain the expression plasmids encoding recombinant proteins (18 in total: RBHBcAg189-SEQ20, RBHBcAg149-SEQ20, TBHBcAg188-SEQ20, TBHBcAg153-SEQ20, HBHBcAg189-SEQ20, HBHBcAg149-SEQ20, RBHBcAg189-SEQ21, RBHBcAg149-SEQ21, TBHBcAg188-SEQ21, TBHBcAg153-SEQ21, HBHBcAg189-SEQ21, HBHBcAg149-SEQ21, RBHBcAg189-SEQ22, RBHBcAg149-SEQ22, TBHBcAg188-SEQ22, TBHBcAg153-SEQ22, HBHBcAg189-SEQ22, and HBHBcAg149-SEQ22).

2.2 Expression, purification and assembly of recombinant proteins The 18 expression plasmids constructed in the previous step, were used to express and purify the recombinant proteins encoded by the expression plasmids via the same method. RBHBcAg149-SEQX (SEQX represents SEQ20, SEQ21 or SEQ22) was used as an example to describe the expression and purification of the recombinant proteins.

(2.2.1) Preparation of bacterial strains for expressing recombinant proteins: the expression plasmid RBHBcAg149-SEQX obtained in 2.1 was transformed into *E. coli* strain ER2566, so as to obtain the expression bacterial strain.

(2.2.2) Expression of the recombinant protein RBHBcAg149-SEQX: the expression bacterial strain was seeded

TABLE 3

| Sense and antisense sequences coding 3 target polypeptides | | |
|---|---|---|
| SEQ ID NO: | Primer name | Sequence |
| 54 | hPDL1-aa147-160F | GATCCACCTCTGAACATGAACTGACATGTCAGGCTGAGGGCTACCCCG |
| 55 | hPDL1-aa147-160R | AATTCGGGGTAGCCCTCAGCCTGACATGTCAGTTCATGTTCAGAGGTG |
| 56 | HIV-GP120-aa361-375F | GATCCTTCAAACAGTCTTCTGGTGGTGACCCGGAAATCGTTACCCACTCTG |
| 57 | HIV-GP120-aa361-375R | AATTCAGAGTGGGTAACGATTTCCGGGTCACCACCAGAAGACTGTTTGAAG |
| 58 | HBsAg-aa113-135F | GATCCTCATCAACAACCAGCACCGGACCATGCAAAACCTGCACAACTCCTG CTCAAGGAACCTCTATGTTTCCCG |
| 59 | HBsAg-aa113-135R | AATTCGGGAAACATAGAGGTTCCTTGAGCAGGAGTTGTGCAGGTTTTGCAT GGTCCGGTGCTGGTTGTTGATGAG |

in a 500 mL triangular flask, and was cultured at 37° C. on a shaking table until OD was about 1.0; later, isopropyl-beta-D-thiogalactoside (IPTG) was added at a final concentration of 0.5 mM, and the expression was further performed at 25° C. for 6 h.

(2.2.3) Purification of the recombinant protein RBH-BcAg149-SEQX:

(2.2.3.1) Ultrasonic disruption of bacteria: the bacteria in 2.2.2 were harvested by centrifugation, and were subjected to ultrasonic disruption. Sonication buffer: 20 mM phosphate buffer (PH6.0)+300 mM NaCl.

(2.2.3.2) Primary purification of the recombinant protein: the mixture obtained after ultrasonic disruption was incubated in a 65° C. water bath for 30 min, and the supernatant was then collected by centrifugation; saturated ammonium sulfate was added to the supernatant at a volume ratio of 1:1, and the precipitate was collected by centrifugation; a suitable volume of buffer (20 mM phosphate buffer (pH=7.4)+150 mM NaCl) was added to resuspend the precipitate, so as to obtain the primarily purified recombinant protein RBH-BcAg149-SEQX.

(2.2.3.3) Purification of the recombinant protein by chromatography: in accordance with the instructions of manufacturer, the protein obtained in 2.2.3.2 was further purified by Sepharose 4FF(GE) molecular sieve column chromatography, so as to obtain the purified recombinant protein. The purified target protein was detected by SDS-PAGE, and the VLP formed by the recombinant protein was observed by Transmission Electron Microscope (TEM).

Figure 2:
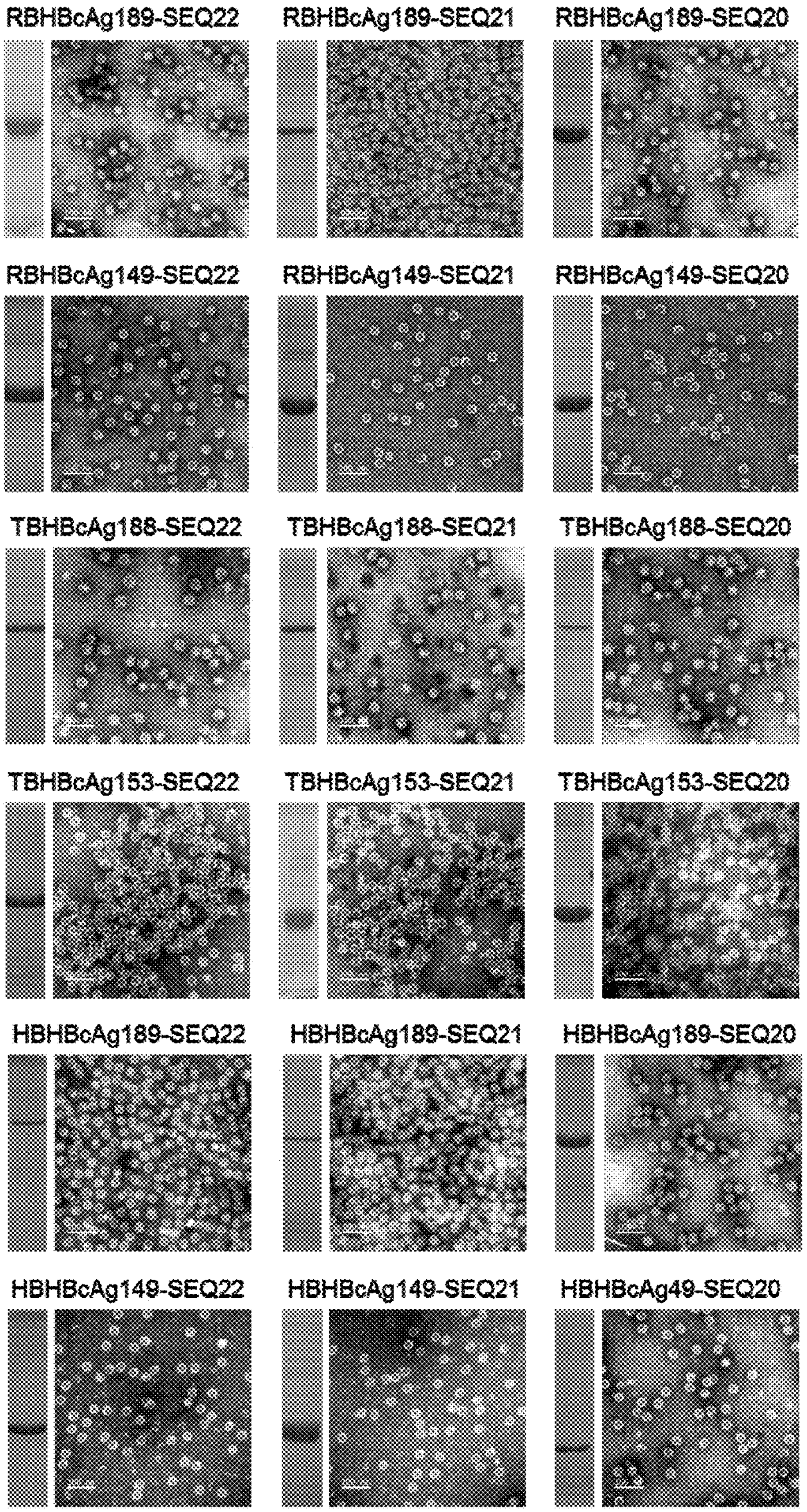
FIG. 2 shows the SDS-PAGE results of 18 recombinant proteins constructed in Example 2, and the Transmission Electron Microscope (TEM) results of the virus-like particles formed by the recombinant proteins.

FIG. 2 shows the SDS-PAGE results of the 18 recombinant proteins as constructed, and the TEM results of the virus-like particles formed by the recombinant proteins. The results show that all the 18 recombinant proteins as obtained had a purity of above 85%, and could be assembled into virus-like particles with a diameter of about 30 nm. These results show that the polypeptide carriers constructed in the invention have a broad versatility, can be used to present various target polypeptides, and can form VLPs.

EXAMPLE 3

Evaluation on Immunogenicity of Virus-Like Particles

In the Example, the inventors verified the immunogenicity of the virus-like particles formed by the recombinant proteins of the invention. All such virus-like particles can induce generation of antibodies that specifically bind to target antigens in organisms.

3.1 Immunization of Mice

BALB/C mice were immunized with the 18 virus-like particles prepared in Example 2, respectively. The immunization process was as followed: the immunoadjuvant used was aluminum hydroxide adjuvant; the immunizing dose was 3 ug/dose; the immunization was performed by intramuscular injection at lateral thigh of hindlimb; the immune procedure was primary immunization+booster immunization 2 weeks later (i.e. two times in total).

3.2 Detection of Titer of Antibodies that Specifically Bind to Target Antigens in Sera 3.2.1 Preparation of Reaction Plates The antigens for coating reaction plates were the target antigens corresponding to said three target polypeptides, i.e., HIV-1 gp120 protein (purchased from Sino Biological Inc., Catalog No. 11233-V08H), human PD-L1 protein (purchased from Sino Biological Inc.), and human hepatitis B virus surface antigen recombinantly expressed in CHO cells (HBsAg, purchased from Beijing Wantai Biological Pharmacy).

3 recombinant proteins were diluted with pH9.6 50 mM CB buffer ($NaHCO_3/Na_2CO_3$ buffer, at a final concentration of 50 mM, pH=9.6), respectively, at a final concentration of 2 μg/mL, to obtain the coating solutions. To each well of a 96-well ELISA plate, 100 μL coating solution was added, and the wells were coated at 2-8° C. for 16-24 h, and then further coated at 37° C. for 2 h. After that, PBST washing solution (20 mM PB7.4, 150 mM NaCl, 0.1% Tween20) was used to wash wells once; and 200 μL blocking solution (20 mM $Na_2HPO_4/NaH_2PO_4$ buffer solution containing 20% bovine calf serum and 1% casein, pH=7.4) was then added to each well, and the wells were blocked at 37° C. for 2 h. The blocking solution was discarded. After that, the ELISA plate was dried, and packaged into an aluminum foil bag, which was stored at 2-8° C. for further use.

3.2.2 ELISA Detection of Anti-HBsAg Antibody Titer in Serum

Collection of serum samples: blood was collected from the eye orbit of mice at Week 0, 2, and 4, the serum was separated and cryopreserved at −20° C., until detection.

Sample dilution: a mouse serum was diluted with PBS solution containing 20% newborn bovine serum at 7 dilution gradients, i.e. 1:100, 1:500, 1:2500, 1:12500, 1:62500, 1:312500, and 1:1562500.

ELISA detection: to each well of the coated ELISA plate, 100 μL diluted serum sample was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 100 μL GAM-HRP reaction solution was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 50 μL TMB color developing agent (provided by Beijing Wantai Biological Pharmacy) was added, and incubated at 37° C. for 15 min. After the incubation, to each well of the ELISA plate, 50 μL stop solution (provided by Beijing Wantai Biological Pharmacy) was added, and the OD450/630 value for each well was read by an ELISA instrument.

Calculation of antibody titer: samples, the read values of which were within 0.2-2.0, were analyzed; a regression curve was plotted with the dilution fold and the read value, and the dilution fold of the sample, at which the read value was 2-fold of the background value, was calculated; and the dilution fold of the sample was used as the titer of the specific antibody in serum.

Figure 3:
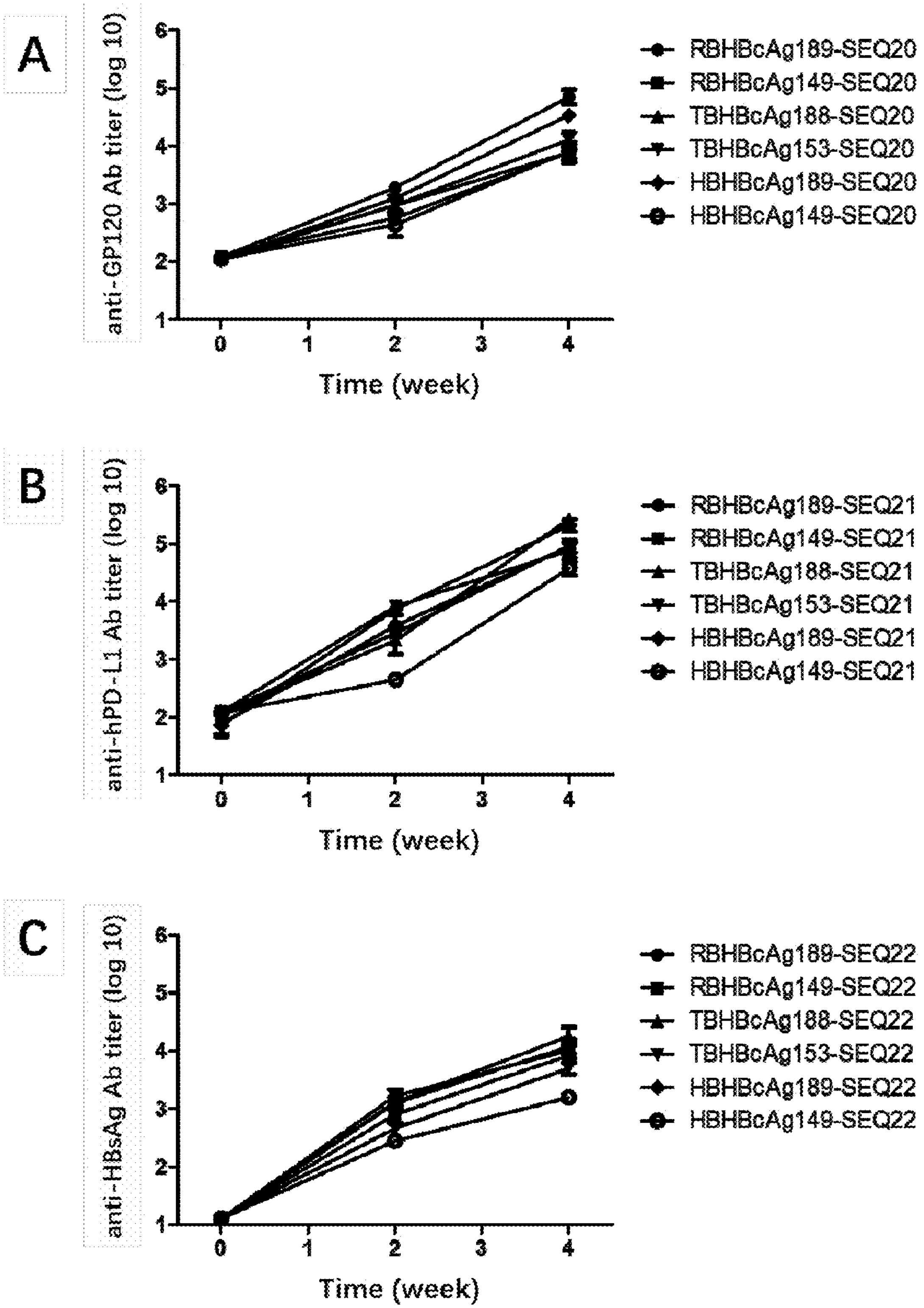
FIG. 3 shows changes in titer of antibodies against the target polypeptides in the recombinant proteins in mouse sera over time, after the immunization of BALB/C mice with the virus-like particles formed by 18 recombinant proteins constructed in Example 2. Longitudinal axis: antibody titer (log 10); horizontal axis: time (week).

FIG. 3 shows changes in titer of antibodies against the target antigen in mouse sera over time, after the immunization of BALB/C mice with the virus-like particles formed by 18 recombinant proteins, respectively. FIG. 3A: the target polypeptide used was SEQ ID NO: 20, and the titer of anti-GP120 antibodies was determined; FIG. 3B: the target polypeptide used was SEQ ID NO: 21, and the titer of anti-PD-L1 antibodies was determined; FIG. 3C: the target polypeptide used was SEQ ID NO: 22, and the titer of anti-HBsAg antibodies was determined. The results show that all the virus-like particles formed by 18 recombinant proteins have good immunogenicity, and can induce the generation of high-titer antibodies that specifically bind to target antigens in mice.

EXAMPLE 4

Evaluation on Anti-HBV Therapeutic Effects of Virus-Like Particles Presenting HBsAg Epitope (SEQ ID NO: 22)

In the Example, the inventors evaluated the anti-HBV therapeutic effects of the virus-like particles presenting the same epitope peptide (SEQ ID NO: 22), as constructed based on different polypeptide carriers.

4.1 Immunization of Mice

According to the methods described in Example 1-2, 2 recombinant proteins (i.e., HBcAg183-SEQ22, its amino acid sequence is set forth in SEQ ID NO: 41; and HBcAg149-SEQ22, its amino acid sequence is set forth in SEQ ID NO: 42), presenting HBsAg epitope (SEQ ID NO: 22) and constructed based on HBcAg of human HBV, were prepared, and the virus-like particles formed by the 2 recombinant proteins were prepared.

Later, 5 virus-like particles presenting HBsAg epitope (SEQ ID NO: 22) prepared in Example 2, and 2 virus-like particles prepared in the Example were evaluated for the anti-HBV therapeutic effects in a HBV transgenic mouse model.

The immunization method was as followed: the immunoadjuvant used was aluminum hydroxide adjuvant; and the immunizing dose was 12 μg/dose; the immunization was performed by intramuscular injection at lateral thigh of hindlimb; the immune procedure was immunization at Week 0, 2, 3, 4, 5, and 6, (i.e. six times in total).

4.2 Detection of Antibody Titer and Virological Index in Serum

According to the method as described in Example 3.2, the Anti-HBsAg antibody titer in serum was determined, and the virological index (i.e., the level of HBV DNA and HBsAg) in mouse serum was determined.

4.3 Analysis of Therapeutic Effects of Recombinant Proteins

Figure 4:
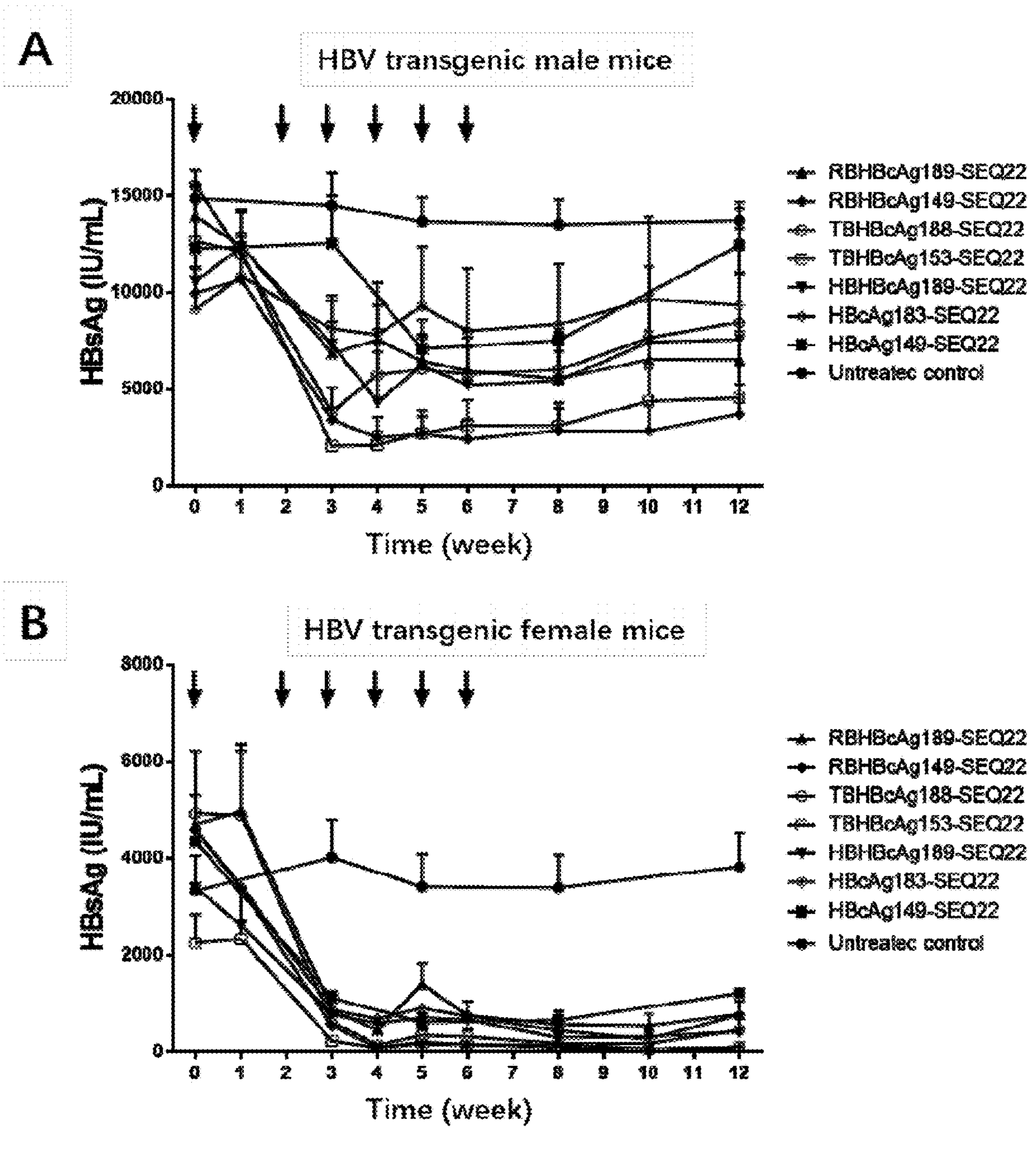
FIG. 4 shows changes in HBsAg level in mouse sera over time, after the treatment of HBV transgenic male (FIG. 4A) and female (FIG. 4B) mice with different virus-like particles presenting the same epitope peptide (SEQ ID NO: 22). Longitudinal axis: HBsAg level (IU/ml); horizontal axis: time (week). The arrows indicate the time points of administering virus-like particles to mice.
Figure 5:
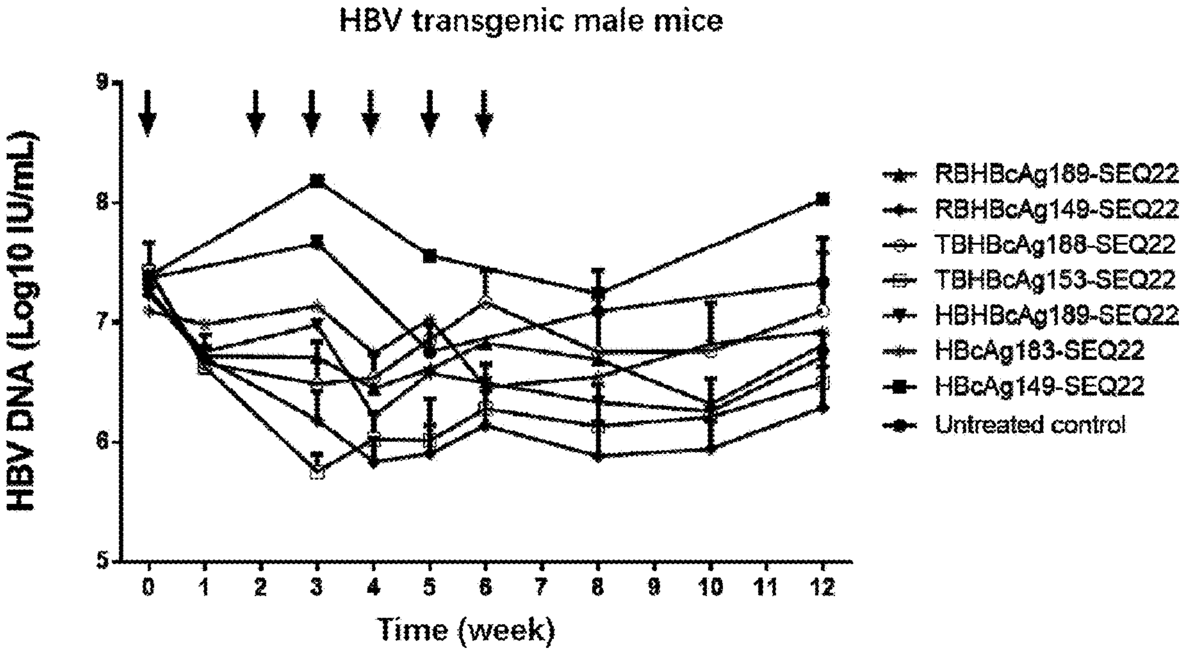
FIG. 5 shows changes in HBV DNA level in mouse sera over time, after the treatment of HBV transgenic male mice with different virus-like particles presenting the same epitope peptide (SEQ ID NO: 22). Longitudinal axis: HBV DNA level (Log 10 IU/ml); horizontal axis: time (week). The arrows indicate the time points of administering virus-like particles to mice.
Figure 6:
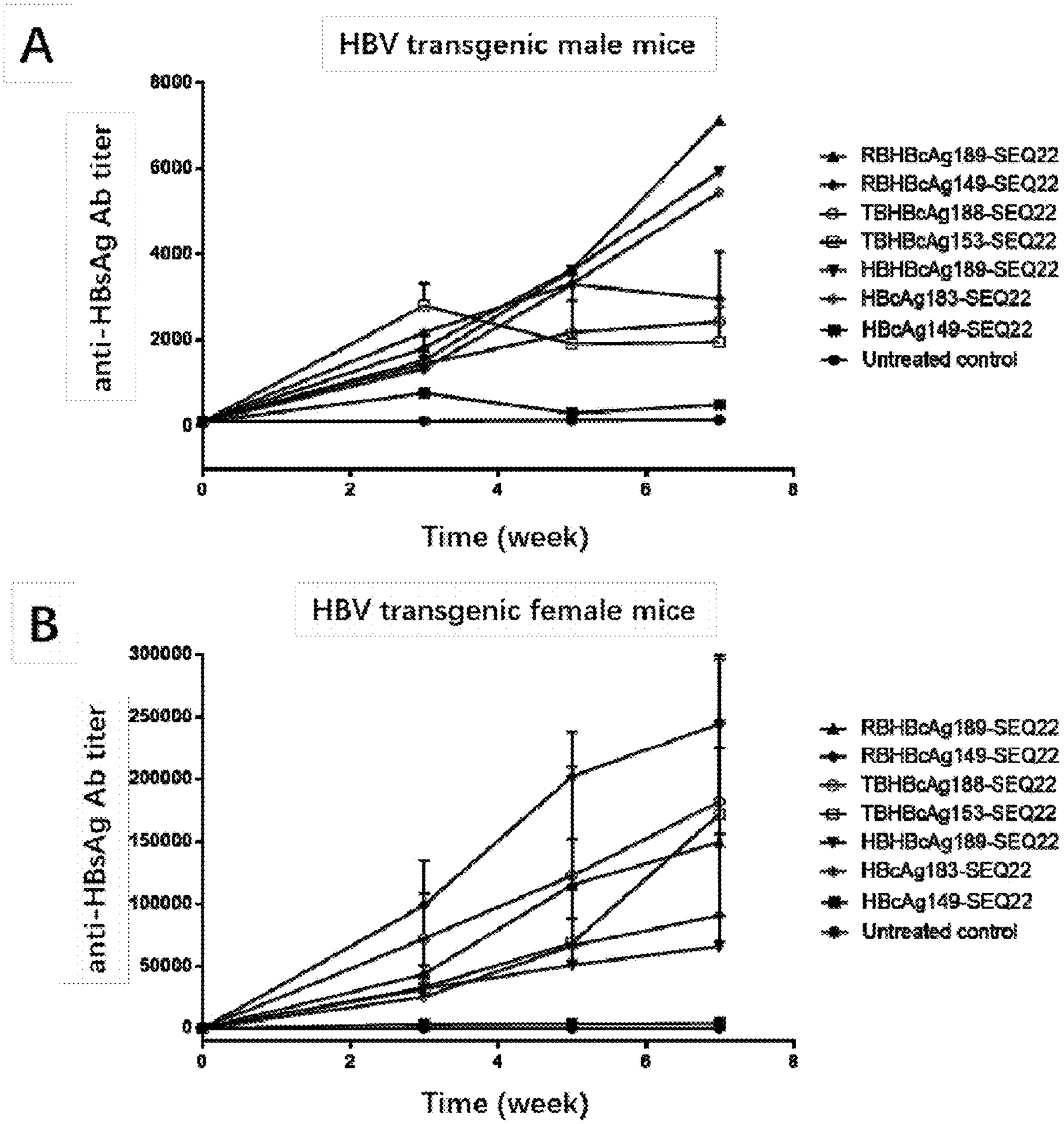
FIG. 6 shows changes in titer of anti-HBsAg antibodies in mouse sera over time, after the treatment of HBV transgenic male (FIG. 6A) and female (FIG. 6B) mice with different virus-like particles presenting the same epitope peptide (SEQ ID NO: 22). Longitudinal axis: the titer of anti-HBsAg antibodies; horizontal axis: time (week).

The detection results are shown in FIG. 4-6. FIG. 4 shows changes in HBsAg level in mouse sera over time, after the treatment of HBV transgenic male (FIG. 4A) and female (FIG. 4B) mice with different virus-like particles presenting the same epitope peptide (SEQ ID NO: 22). FIG. 5 shows changes in HBV DNA level in mouse sera over time, after the treatment of HBV transgenic male mice with different virus-like particles presenting the same epitope peptide (SEQ ID NO: 22). FIG. 6 shows changes in titer of anti-HBsAg antibodies in mouse sera over time, after the treatment of HBV transgenic male (FIG. 6A) and female (FIG. 6B) mice with different virus-like particles presenting the same epitope peptide (SEQ ID NO: 22).

The results show that in the groups receiving immunotherapy with VLP, Anti-HBsAg antibodies were detected in mouse sera after immunization, and the level of HBV DNA and HBsAg decreased to different extents in mouse sera. By comparison, no Anti-HBsAg antibodies were generated in the sera of control mice (which were not immunized with VLP), and no decrease in the level of HBV DNA and HBsAg in sera was observed.

These results show that all the 6 polypeptide carriers, constructed based on bat hepatitis B virus core protein, can be used to effectively present the epitope peptide (e.g., HBsAg-aa113-135) of HBsAg from human HBV, can form VLPs, and induce generation of high-titer anti-HBsAg antibodies in organisms, thereby inhibiting the level of HBV DNA and HBsAg (i.e., HBV DNA and HBsAg decreased significantly) in mice. In addition, the experimental data in FIG. 4-6 also shows that the virus-like particles, based on the polypeptide carriers (e.g. RBHBcAg149 and TBHBcAg153) of the invention, have particularly significant anti-HBV therapeutic effects, better than the virus-like particle constructed based on HBcAg of human HBV.

Therefore, the experimental results in the Example show: (1) the polypeptide carriers of the invention can form VLPs, are suitable for presenting various target polypeptides, and can induce generation of high-titer antibodies against target polypeptides in organisms; (2) the polypeptide carriers of the invention are particularly suitable for presenting epitopes of human HBV (e.g., an epitope of HBsAg of human HBV), can induce generation of high-titer antibodies against HBsAg in organisms, and can clean or inhibit the level of HBV DNA and HBsAg in vivo, with an efficacy better than that of the polypeptide carrier constructed based on HBcAg of human HBV. Thus, the recombinant proteins presenting human HBV epitopes according to the invention are potential in treating HBV infection, and are particularly suitable for inducing effective, specific and therapeutic anti-HBV immunization.

EXAMPLE 5

Preparation and Evaluation of Virus-Like Particles Presenting an Epitope of HBsAg from Different HBV Genotypes The HBsAg epitope (SEQ ID NO: 22) used in Example 2-4 was from HBV genotype B. In order to confirm the broad versatility of the polypeptide carrier of the invention for various HBV genotypes, the inventors also used RBHBcAg149 and TBHBcAg153 as exemplary polypeptide carriers, to construct the recombinant proteins presenting an epitope of HBsAg from different HBV genotypes (genotype A, C and D), and evaluated the ability of the constructed recombinant proteins to be assembled into virus-like particles, the immunogenicity of the virus-like particle produced, and the therapeutic effect thereof against HBV infection.

5.1 Construction of Expression Plasmids Encoding Recombinant Proteins Comprising a Target Polypeptide and a Polypeptide Carrier In the Example, in addition to the HBsAg epitope (from HBV genotype B, SEQ ID NO: 22) used in Example 2-4, the target polypeptide further includes the HBsAg epitope (amino acids from positions 113-135) from HBV genotype A, C and D, designated as: HBsAg-aa113-135-A, HBsAg-aa113-135-C and HBsAg-aa113-135-D, and their sequences (SEQ ID NO: 60-62) are shown in Table 4.

TABLE 4

Sequences of amino acids from positions 113-135 of HBsAg protein from HBV genotype A, C and D

| SEQ ID NO | Name | Sequence information |
|---|---|---|
| 60 | HBsAg-aa113-135-A | STTTSTGPCKTCTTPAQGNSMFP |
| 61 | HBsAg-aa113-135-C | TSTTSTGPCKTCTIPAQGTSMFP |
| 62 | HBsAg-aa113-135-D | SSTTSTGPCRTCTTPAQGTSMYP |

The sense and antisense sequences (as shown in Table 5) coding said 3 target polypeptides were synthesized directly, and annealed, to obtain the gene fragments having cohesive end and encoding the target polypeptides.

TABLE 5

| Sense and antisense sequences coding 3 target polypeptides | | |
|---|---|---|
| SEQ ID NO: | Primer name | Sequence information |
| 63 | HBsAg-aa113-135-AF | GATCCTCTACCACCACCTCTACCGGTCCGTGCAAAACCTGCA CCACCCCGGCTCAGGGTAACTCTATGTTCCCGG |
| 64 | HBsAg-aa113-135-AR | AATTCCGGGAACATAGAGTTACCCTGAGCCGGGGTGGTGCAG GTTTTGCACGGACCGGTAGAGGTGGTGGTAGAG |
| 65 | HBsAg-aa113-135-CF | GATCCACCTCTACCACCTCTACCGGTCCGTGCAAAACCTGCA CCATCCCGGCTCAGGGTACCTCTATGTTCCCGG |
| 66 | HBsAg-aa113-135-CR | AATTCCGGGAACATAGAGGTACCCTGAGCCGGGATGGTGCAG GTTTTGCACGGACCGGTAGAGGTGGTAGAGGTG |
| 67 | HBsAg-aa113-135-DF | GATCCTCTTCTACCACCTCTACCGGTCCGTGCCGTACCTGCA CCACCCCGGCTCAGGGTACCTCTATGTACCCGG |
| 68 | HBsAg-aa113-135-DR | AATTCCGGGTACATAGAGGTACCCTGAGCCGGGGTGGTGCAG GTACGGCACGGACCGGTAGAGGTGGTAGAAGAG |

As described in Example 2, the 3 gene fragments having cohesive end and encoding the target polypeptides as prepared above were ligated to linear vectors RBHBcAg149 and TBHBcAg153, respectively, so as to obtain the expression plasmids encoding the recombinant proteins (6 in total: RBHBcAg149-SEQ60, RBHBcAg149-SEQ61, RBHBcAg149-SEQ62, TBHBcAg153-SEQ60, TBHBcAg153-SEQ61, and TBHBcAg153-SEQ62). The amino acid sequences of the recombinant proteins encoded by the expression plasmids are shown in Table 6.

TABLE 6

| Amino acid sequences of 6 recombinant proteins | | |
|---|---|---|
| SEQ ID NO: | Recombinant protein | Sequence information |
| 69 | RBHBcAg149-SEQ60 | MDIDPYKEFGASSQLISFLPEDFFPNLAELVETTTALYEEELVGKEHCSPHHTALR SLLNCWGETVRLITWVRNSVEGGGGGSGGGGTGSSTTTSTGPCKTCTTPAQGNSMF PEFGGGGSGGGGSQDAIVQQVQASVGLRMRQLMWFHLSCLTFGQPTVIEFLVSFGT WIRTPQAYRPPNAPILSTLPEHTIV |
| 70 | RBHBcAg149-SEQ61 | MDIDPYKEFGASSQLISFLPEDFFPNLAELVETTTALYEEELVGKEHCSPHHTALR SLLNCWGETVRLITWVRNSVEGGGGGSGGGGTGSTSTTSTGPCKTCTIPAQGTSMF PEFGGGGSGGGGSQDAIVQQVQASVGLRMRQLMWFHLSCLTFGQPTVIEFLVSFGT WIRTPQAYRPPNAPILSTLPEHTIV |
| 71 | RBHBcAg149-SEQ62 | MDIDPYKEFGASSQLISFLPEDFFPNLAELVETTTALYEEELVGKEHCSPHHTALR SLLNCWGETVRLITWVRNSVEGGGGGSGGGGTGSSSTTSTGPCRTCTTPAQGTSMY PEFGGGGSGGGGSQDAIVQQVQASVGLRMRQLMWFHLSCLTFGQPTVIEFLVSFGT WIRTPQAYRPPNAPILSTLPEHTIV |
| 72 | TBHBcAg153-SEQ60 | MENLERLDIYKEFGVSDVLVSFLPDDFFPTLQQLLESVNALYEDELTGPNHCSPHH TALRHLIMCGVELRDFIDWMHEQGGGGGSGGGGTGSSTTTSTGPCKTCTTPAQGNS MFPEFGGGGSGGGGSDADALLAGYLRSKYLKHITKAIWYHLSCLTFGKQTVHEYLV SFGTWIRTPAAYRPVNAPILTTLPETSVI |
| 73 | TBHBcAg153-SEQ61 | MENLERLDIYKEFGVSDVLVSFLPDDFFPTLQQLLESVNALYEDELTGPNHCSPHH TALRHLIMCGVELRDFIDWMHEQGGGGGSGGGGTGSTSTTSTGPCKTCTIPAQGTS MFPEFGGGGSGGGGSDADALLAGYLRSKYLKHITKAIWYHLSCLTFGKQTVHEYLV SFGTWIRTPAAYRPVNAPILTTLPETSVI |
| 74 | TBHBcAg153-SEQ62 | MENLERLDIYKEFGVSDVLVSFLPDDFFPTLQQLLESVNALYEDELTGPNHCSPHH TALRHLIMCGVELRDFIDWMHEQGGGGGSGGGGTGSSSTTSTGPCRTCTTPAQGTS MYPEFGGGGSGGGGSDADALLAGYLRSKYLKHITKAIWYHLSCLTFGKQTVHEYLV SFGTWIRTPAAYRPVNAPILTTLPETSVI |

5.2 Expression, Purification and Assembly of Recombinant Proteins

As described in Example 2, by using the 6 expression plasmids constructed in the previous step, the recombinant proteins encoded by the expression plasmids were expressed and purified. Later, the VLPs formed by the recombinant proteins were observed by Transmission Electron Microscope (TEM).

Figure 7:
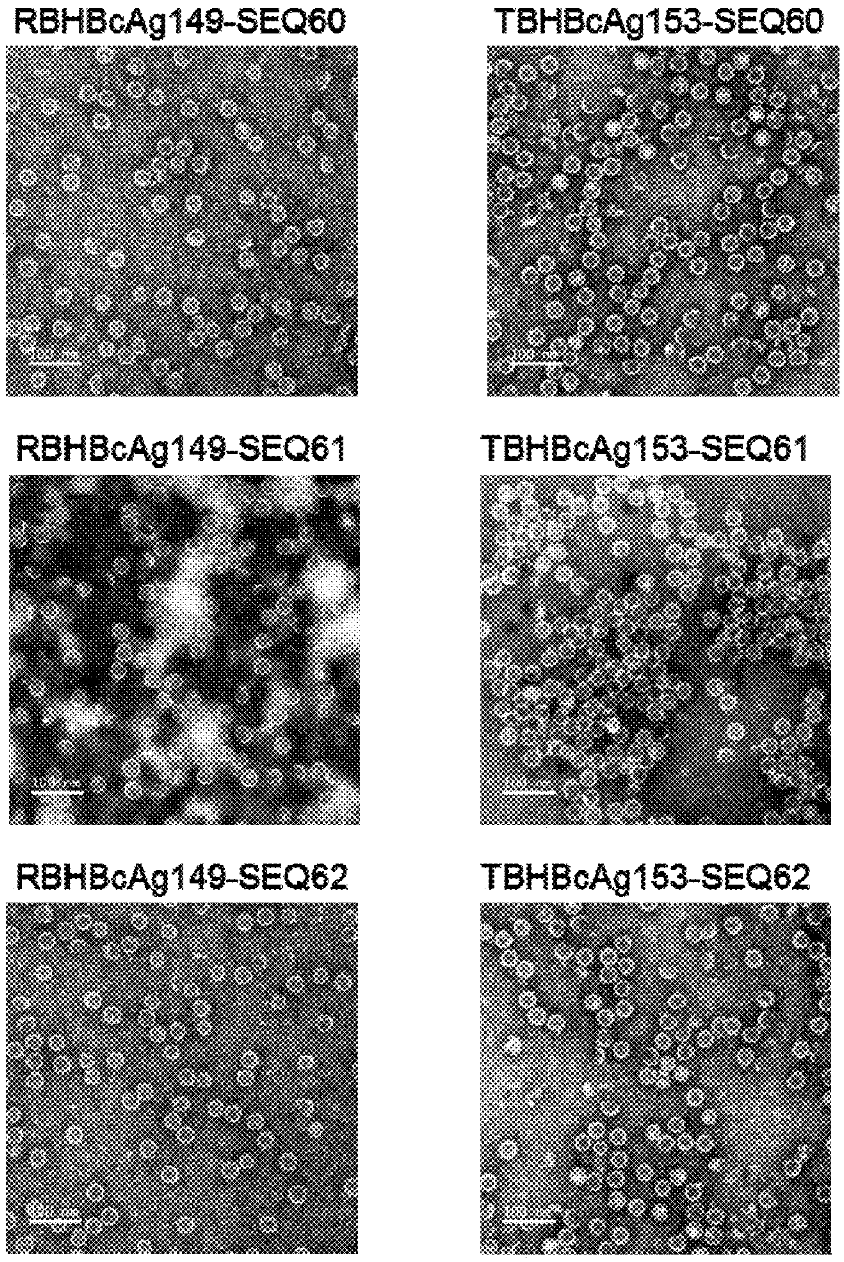
FIG. 7 shows the TEM results of the virus-like particles formed by 6 recombinant proteins constructed in Example 5.

FIG. 7 shows the TEM results of the virus-like particles formed by the 6 recombinant proteins constructed. The results show that all the 6 recombinant proteins obtained can be assembled into virus-like particles with a diameter of about 30 nm. These results show that the polypeptide carriers constructed in the invention have a broad versatility, can be used to present epitope peptides (e.g., aa113-135 of HBsAg protein) from various HBV genotypes, and can form VLPs well.

5.3 Evaluation of Immunogenicity of Virus-Like Particles

By using the method described in Example 3, the virus-like particles, formed by the 6 recombinant proteins as constructed above and the recombinant proteins RBHBcAg149-SEQ22 and TBHBcAg153-SEQ22 in Example 2, were evaluated for their immunogenicity. The experimental results are shown in FIG. 8.

Figure 8:
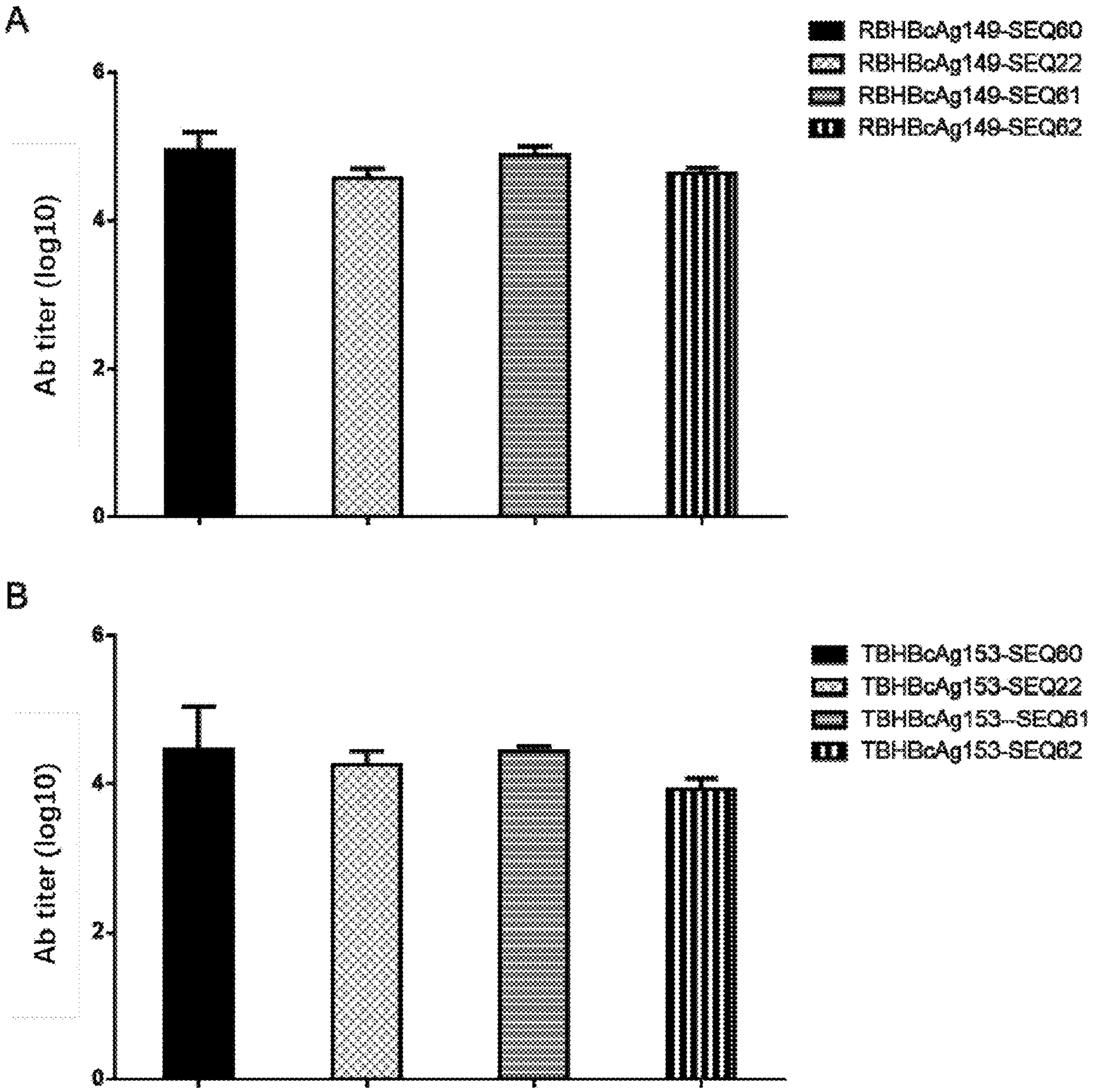
FIG. 8 shows the titers of antibodies against the corresponding target polypeptides (SEQ ID NO: 60, 22, 61, and 62) in mouse sera, three weeks after the immunization of BALB/C mice with the virus-like particles formed by 8 recombinant proteins; wherein the epitope peptide (SEQ ID NO: 60) of HBsAg protein from HBV genotype A was used to determine the antibody titers in sera of mice immunized with RBHBcAg149-SEQ60 and TBHBcAg153-SEQ60; the epitope peptide (SEQ ID NO: 22) of HBsAg protein from HBV genotype B was used to determine the antibody titers in sera of mice immunized with RBHBcAg149-SEQ22 and TBHBcAg153-SEQ22; the epitope peptide (SEQ ID NO: 61) of HBsAg protein from HBV genotype C was used to determine the antibody titers in sera of mice immunized with RBHBcAg149-SEQ61 and TBHBcAg153-SEQ61; and the epitope peptide (SEQ ID NO: 62) of HBsAg protein from HBV genotype D was used to determine the antibody titers in sera of mice immunized with RBHBcAg149-SEQ62 and TBHBcAg153-SEQ62. The results show that all the virus-like particles formed by the 8 recombinant proteins have good immunogenicity, and can induce generation of high-titer antibodies that specifically bind to target antigens in mice.

FIG. 8 shows the titers of antibodies against the corresponding target polypeptides (SEQ ID NO: 60, 22, 61, and 62) in mouse sera, three weeks after the immunization of BALB/C mice with the virus-like particles formed by the 8 recombinant proteins; wherein the epitope peptide (SEQ ID NO: 60) of HBsAg protein from HBV genotype A was used to determine the antibody titers in sera of mice immunized with RBHBcAg149-SEQ60 and TBHBcAg153-SEQ60; the epitope peptide (SEQ ID NO: 22) of HBsAg protein from HBV genotype B was used to determine the antibody titers in sera of mice immunized with RBHBcAg149-SEQ22 and TBHBcAg153-SEQ22; the epitope peptide (SEQ ID NO: 61) of HBsAg protein from HBV genotype C was used to determine the antibody titers in sera of mice immunized with RBHBcAg149-SEQ61 and TBHBcAg153-SEQ61; and the epitope peptide (SEQ ID NO: 62) of HBsAg protein from HBV genotype D was used to determine the antibody titers in sera of mice immunized with RBHBcAg149-SEQ62 and TBHBcAg153-SEQ62. The results show that the virus-like particles formed by the 8 recombinant proteins have good immunogenicity, and can induce generation of high-titer antibodies that specifically bind to target epitopes in mice.

5.4 Evaluation on Anti-HBV Therapeutic Effects of Virus-Like Particles

By using the method as described in Example 4, the virus-like particles formed by 4 recombinant proteins (SEQ ID NO: 36, 69, 70, and 71) were evaluated for the anti-HBV therapeutic effects. The experimental results are shown in FIG. 9.

Figure 9:
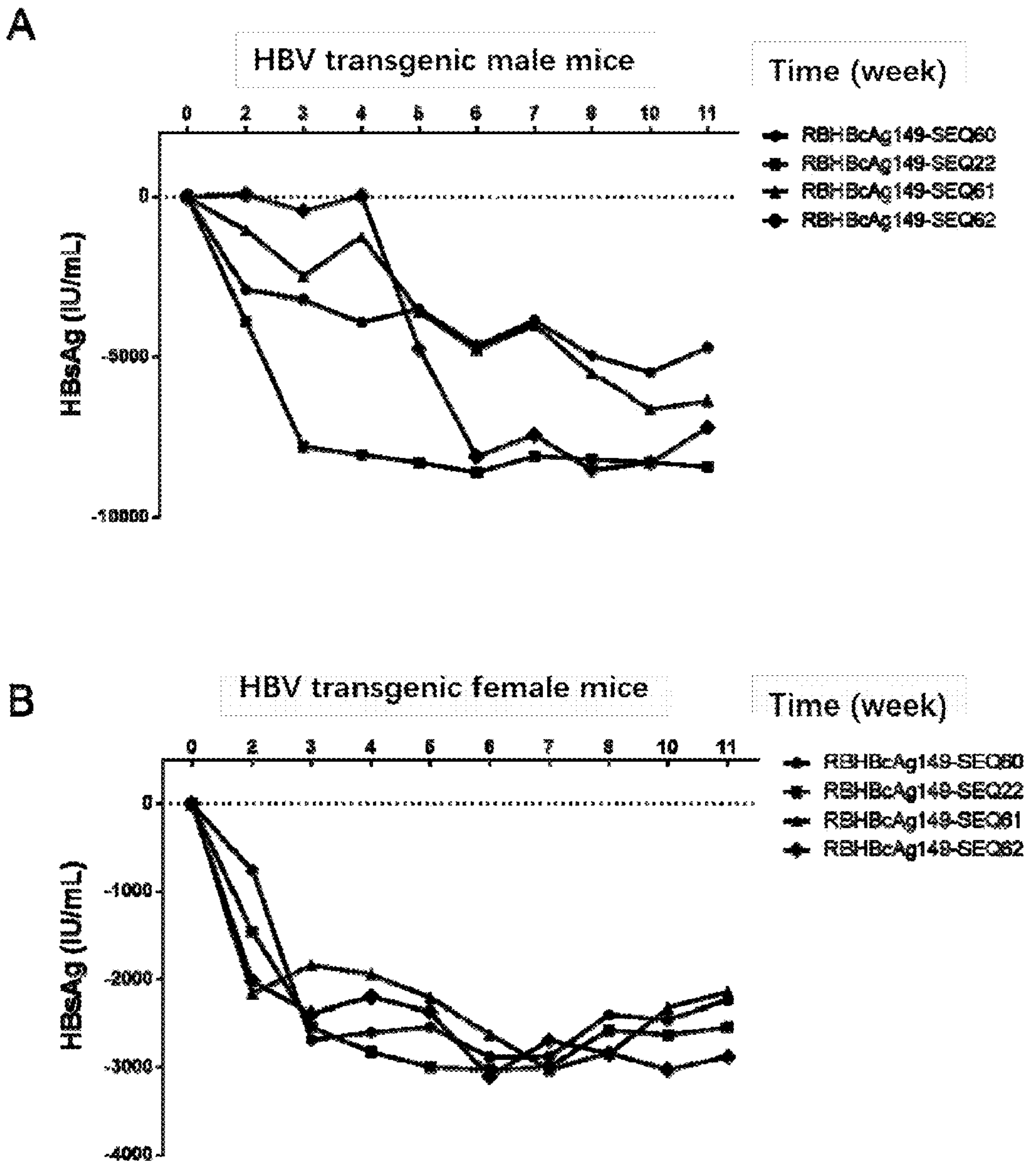
FIG. 9 shows changes in HBsAg level in mouse sera, after the treatment of HBV transgenic male (FIG. 9A) and female (FIG. 9B) mice with the virus-like particles formed by 4 recombinant proteins (SEQ ID NO: 36, 69, 70, and 71), wherein, longitudinal axis: HBsAg level (IU/ml); horizontal axis: time (week).

FIG. 9 shows changes in HBsAg level in mouse sera over time, after the treatment of HBV transgenic male (FIG. 9A) and female (FIG. 9B) mice with the virus-like particles formed by the 4 recombinant proteins constructed above (RBHBcAg149-SEQ22, RBHBcAg149-SEQ60, RBHBcAg149-SEQ61, and RBHBcAg149-SEQ62; the sequences thereof are SEQ ID NO: 36, 69, 70, and 71, respectively), wherein, longitudinal axis: HBsAg level (IU/ml); horizontal axis: time (week). The results show that in the mice receiving immunotherapy with VLP, the HBsAg level in mouse sera decreased significantly after immunization.

These experimental results show that the polypeptide carriers of the invention (e.g., RBHBcAg149 and TBHBcAg153) can be used to effectively present epitope peptides (e.g., HBsAg-aa113-135) of HBsAg from human HBV of different genotypes (e.g., genotype A, B, C and D). The recombinant proteins, constructed based on the polypeptide carriers of the invention and epitope peptides of HBsAg, can form VLPs, and can induce the generation of high-titer anti-HBsAg antibodies in organisms, thereby inhibiting the HBsAg level (i.e., the HBsAg level decreased significantly) in mice. This indicates that the recombinant proteins comprising the polypeptide carriers of the invention and epitope peptides of HBsAg can be used to prevent and treat the infection by various HBV genotypes, and therefore can be used in the development of new anti-HBV vaccines and medicaments.

Although the embodiments of the invention have been described in detail, a person skilled in the art would understand that according to all the disclosed teachings, details can be amended and modified, and these alterations all fall into the protection scope of the invention. The scope of the invention is defined by the attached claims and any equivalent thereof.

The invention claimed is:

1. A nucleic acid molecule, comprising:

a nucleotide sequence encoding a polypeptide carrier, or a variant thereof, wherein the variant has at least 90% identity to the nucleotide sequence, or is capable of hybridizing to the nucleotide sequence under a stringent condition or a high stringent condition, and wherein the polypeptide carrier is selected from the group consisting of:

(1) RBHBcAg carrier, which differs from a core antigen protein from roundleaf bat HBV (RBHBcAg protein) in that (a) 1 to 6 amino acid residues corresponding to the amino acid residues at positions 78-83 of SEQ ID NO: 1 are deleted or substituted with a linker, and (b) optionally, 1-40 amino acid residues at C-terminus of the RBHBcAg protein are deleted;

(2) TBHBcAg carrier, which differs from a core antigen protein from tent-making bat HBV (TBHBcAg protein) in that (a) 1 to 5 amino acid residues corresponding to the amino acid residues at positions 80-84 of SEQ ID NO: 2 are deleted or substituted with a linker, and (b) optionally, 1-35 amino acid residues at C-terminus of the TBHBcAg protein are deleted; and (3) HBHBcAg carrier, which differs from a core antigen protein from horseshoe bat HBV (HBHBcAg protein)

in that (a) 1 to 6 amino acid residues corresponding to the amino acid residues at positions 78-83 of SEQ ID NO: 3 are deleted or substituted with a linker, and (b) optionally, 1-40 amino acid residues at C-terminus of the HBHBcAg protein are deleted.

2. A vector, comprising the nucleic acid molecule of claim 1.

3. A host cell, comprising the nucleic acid molecule of claim 1 or a vector comprising the nucleic acid molecule.

4. A method for presenting a target polypeptide, comprising:

(1) inserting a nucleotide sequence encoding the target polypeptide into the nucleic acid molecule of claim 1 to obtain a nucleic acid molecule encoding a recombinant protein, wherein the nucleotide sequence encoding the target polypeptide is inserted at a position of nucleotides encoding the deleted amino acid residues, inserted in the nucleotide sequence encoding the linker, or inserted at one or both termini of the nucleotide sequence encoding the linker; and (2) expressing the nucleic acid molecule encoding the recombinant protein to produce the recombinant protein.

5. A recombinant protein, comprising:

a polypeptide carrier; and a target polypeptide, wherein the polypeptide carrier is selected from the group consisting of:

(1) RBHBcAg carrier, which differs from a core antigen protein from roundleaf bat HBV (RBHBcAg protein) in that (a) 1 to 6 amino acid residues corresponding to the amino acid residues at positions 78-83 of SEQ ID NO: 1 are deleted or substituted with a linker, and (b) optionally, 1-40 amino acid residues at C-terminus of the RBHBcAg protein are deleted;

(2) TBHBcAg carrier, which differs from a core antigen protein from tent-making bat HBV (TBHBcAg protein) in that (a) 1 to 5 amino acid residues corresponding to the amino acid residues at positions 80-84 of SEQ ID NO: 2 are deleted or substituted with a linker, and (b) optionally, 1-35 amino acid residues at C-terminus of the TBHBcAg protein are deleted; and (3) HBHBcAg carrier, which differs from a core antigen protein from horseshoe bat HBV (HBHBcAg protein) in that (a) 1 to 6 amino acid residues corresponding to the amino acid residues at positions 78-83 of SEQ ID NO: 3 are deleted or substituted with a linker, and (b) optionally, 1-40 amino acid residues at C-terminus of the HBHBcAg protein are deleted, and wherein the target polypeptide is inserted at a position of the deleted amino acid residues, inserted in the linker, or inserted at one or both of the termini of the linker.

6. A virus-like particle, comprising the recombinant protein of claim 5.

7. A pharmaceutical composition, comprising:

the recombinant protein of claim 5 or a virus-like particle comprising the recombinant protein; and at least one pharmaceutically acceptable vehicle or excipient.

8. A polynucleotide, encoding the recombinant protein of claim 5.

9. A vector, comprising the polynucleotide of claim 8.

10. A host cell, comprising the polynucleotide of claim 8 or a vector comprising the polynucleotide.

11. A method for preparing the recombinant protein of claim 5, comprising:

culturing a host cell comprising a polynucleotide encoding the recombinant protein under a condition suitable for expressing the recombinant protein; and recovering the recombinant protein.

12. The nucleic acid molecule of claim 1, wherein at least one of (i) to (xi) is satisfied:

(i) the RBHBcAg protein has the amino acid sequence of SEQ ID NO: 1;

(ii) the RBHBcAg carrier differs from the RBHBcAg protein in that (a) amino acid residues corresponding to the amino acid residues at positions 78-82 of SEQ ID NO: 1 are deleted or substituted with a linker, and (b) optionally, 5-35 amino acid residues at C-terminus of the RBHBcAg protein are deleted;

(iii) the TBHBcAg protein has the amino acid sequence of SEQ ID NO: 2;

(iv) the TBHBcAg carrier differs from the TBHBcAg protein in that (a) amino acid residues corresponding to the amino acid residues at positions 80-83 of SEQ ID NO: 2 are deleted or substituted with a linker, and (b) optionally, 5-30 amino acid residues at C-terminus of the TBHBcAg protein are deleted;

(v) the HBHBcAg protein has the amino acid sequence of SEQ ID NO: 3;

(vi) the HBHBcAg carrier differs from the HBHBcAg protein in that (a) amino acid residues corresponding to the amino acid residues at positions 78-82 of SEQ ID NO: 3 are deleted or substituted with a linker, and (b) optionally, 5-35 amino acid residues at C-terminus of the HBHBcAg protein are deleted;

(vii) the linker is a flexible linker;

(viii) a restriction enzyme cleavage site is introduced at a position of nucleotides encoding the amino acid residues that are deleted;

(ix) a restriction enzyme cleavage site is introduced in the nucleotide sequence encoding the linker, and/or at either or both of the termini thereof;

(x) the nucleic acid molecule is used to insert a nucleotide sequence encoding a target polypeptide; and (xi) the nucleic acid molecule further comprises a nucleotide sequence encoding a target polypeptide, wherein the target polypeptide is heterologous relative to the polypeptide carrier, and the nucleotide sequence encoding the target polypeptide is inserted at a position of nucleotides encoding the deleted amino acid residues, inserted in the nucleotide sequence encoding the linker, or inserted at one or both termini of the nucleotide sequence encoding the linker.

13. The nucleic acid molecule of claim 1, wherein the polypeptide carrier has the amino acid sequence of SEQ ID NO: 4, 5, 6, 7, 8 or 9, or the nucleic acid molecule comprises the nucleotide sequence of SEQ ID NO: 12, 13, 14, 15, 16 or 17.

14. The method of claim 4, wherein the target polypeptide is an epitope peptide, and optionally, the epitope peptide satisfies at least one of (i) to (iii):

(i) the epitope peptide comprises an epitope of HBsAg from human HBV, or an epitope of HIV GP120 protein, or an epitope of human PD-L1;

(ii) the epitope peptide comprises amino acids corresponding to the amino acids at positions 113-135 of SEQ ID NO: 44 (HBsAg protein), the amino acids at positions 361-375 of an amino acid sequence of HIV GP120 protein, or the amino acids at positions 147-160 of an amino acid sequence of human PD-L1 protein; and (iii) the epitope peptide has the amino acid sequence of SEQ ID NO: 20, 21, 22, 60, 61, or 62.

15. The recombinant protein of claim 5, wherein at least one of (i) to (x) is satisfied:

(i) the RBHBcAg protein has the amino acid sequence of SEQ ID NO: 1;

(ii) the RBHBcAg carrier differs from the RBHBcAg protein in that (a) amino acid residues corresponding to the amino acid residues at positions 78-82 of SEQ ID NO: 1 are deleted or substituted with a linker, and (b) optionally, 5-35 amino acid residues at C-terminus of the RBHBcAg protein are deleted;

(iii) the TBHBcAg protein has the amino acid sequence of SEQ ID NO: 2;

(iv) the TBHBcAg carrier differs from the TBHBcAg protein in that (a) amino acid residues from corresponding to the amino acid residues at positions 80-83 of SEQ ID NO: 2 are deleted or substituted with a linker, and (b) optionally, 5-30 amino acid residues at C-terminus of the TBHBcAg protein are deleted;

(v) the HBHBcAg protein has the amino acid sequence of SEQ ID NO: 3;

(vi) the HBHBcAg carrier differs from the HBHBcAg protein in that (a) amino acid residues corresponding to the amino acid residues at positions 78-82 of SEQ ID NO: 3 are deleted or substituted with a linker, and (b) optionally, 5-35 amino acid residues at C-terminus of the HBHBcAg protein are deleted;

(vii) the linker is a flexible linker;

(viii) the polypeptide carrier has the amino acid sequence of SEQ ID NO: 4, 5, 6, 7, 8, or 9;

(ix) the target polypeptide is an epitope peptide, and optionally, the epitope peptide comprises an epitope of HBsAg from human HBV, an epitope of HIV GP120 protein, or an epitope of human PD-L1, or comprises amino acids at positions 113-135 of an amino acid sequence of HBsAg protein, amino acids at positions 361-375 of an amino acid sequence of HIV GP120 protein, or amino acids at positions 147-160 of an amino acid sequence of human PD-L1 protein, or comprises the amino acid sequence of SEQ ID NO: 20, 21, 22, 60, 61, or 62; and (x) the recombinant protein comprises or consists of the amino acid sequence selected from the group consisting of SEQ ID NOS: 23-40 and 69-74.

* * * * *

SEQUENCE LISTING

```
<160> NUMBER OF SEQ ID NOS: 74

<210> SEQ ID NO 1
<211> LENGTH: 189
<212> TYPE: PRT
<213> ORGANISM: roundleaf bat HBV

<400> SEQUENCE: 1

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Pro Leu
65                  70                  75                  80

Ile Gln Asp Ala Ile Val Gln Gln Val Gln Ala Ser Val Gly Leu Arg
                85                  90                  95

Met Arg Gln Leu Met Trp Phe His Leu Ser Cys Leu Thr Phe Gly Gln
            100                 105                 110

Pro Thr Val Ile Glu Phe Leu Val Ser Phe Gly Thr Trp Ile Arg Thr
        115                 120                 125
```

```
Pro Gln Ala Tyr Arg Pro Pro Asn Ala Pro Ile Leu Ser Thr Leu Pro
    130                 135                 140

Glu His Thr Ile Val Arg Arg Arg Gly Gly Ser Arg Ala Thr Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ala Ser Ser Asn Cys
            180                 185


<210> SEQ ID NO 2
<211> LENGTH: 188
<212> TYPE: PRT
<213> ORGANISM: tent-making bat HBV

<400> SEQUENCE: 2

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Leu Ser Pro Asp Ala Asp Ala Leu Leu Ala Gly Tyr Leu Arg Ser Lys
                85                  90                  95

Tyr Leu Lys His Ile Thr Lys Ala Ile Trp Tyr His Leu Ser Cys Leu
            100                 105                 110

Thr Phe Gly Lys Gln Thr Val His Glu Tyr Leu Val Ser Phe Gly Thr
        115                 120                 125

Trp Ile Arg Thr Pro Ala Ala Tyr Arg Pro Val Asn Ala Pro Ile Leu
    130                 135                 140

Thr Thr Leu Pro Glu Thr Ser Val Ile Arg Arg Arg Pro Ala Ser Arg
145                 150                 155                 160

Arg Ser Thr Pro Ser Pro Arg Arg Arg Arg Ser Gln Ser Pro Arg Arg
                165                 170                 175

Arg Arg Ser Pro Ser Pro Arg Pro Ala Ser Asn Cys
            180                 185


<210> SEQ ID NO 3
<211> LENGTH: 189
<212> TYPE: PRT
<213> ORGANISM: horseshoe bat HBV

<400> SEQUENCE: 3

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gln Pro
65                  70                  75                  80
```

```
Val Gln Asp Ala Ile Ile Gly Tyr Val Gln Thr Thr Val Gly Leu Arg
                85                  90                  95

Met Arg Gln Gln Ile Trp Phe His Leu Ser Cys Leu Thr Phe Gly Gln
            100                 105                 110

Gln Thr Val Ile Glu Phe Leu Val Ser Phe Gly Thr Trp Met Arg Thr
        115                 120                 125

Pro Ala Ala Tyr Arg Pro Pro Asn Ala Pro Ile Leu Ser Thr Leu Pro
    130                 135                 140

Glu His Thr Val Ile Arg Arg Arg Gly Asn Pro Arg Ala Pro Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ala Pro Ser Asn Cys
            180                 185


<210> SEQ ID NO 4
<211> LENGTH: 210
<212> TYPE: PRT
<213> ORGANISM: Artificial
<220> FEATURE:
<223> OTHER INFORMATION: RBHBcAg189 carrier

<400> SEQUENCE: 4

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Gln Asp Ala Ile Val Gln Gln Val Gln Ala
            100                 105                 110

Ser Val Gly Leu Arg Met Arg Gln Leu Met Trp Phe His Leu Ser Cys
        115                 120                 125

Leu Thr Phe Gly Gln Pro Thr Val Ile Glu Phe Leu Val Ser Phe Gly
    130                 135                 140

Thr Trp Ile Arg Thr Pro Gln Ala Tyr Arg Pro Pro Asn Ala Pro Ile
145                 150                 155                 160

Leu Ser Thr Leu Pro Glu His Thr Ile Val Arg Arg Arg Gly Gly Ser
                165                 170                 175

Arg Ala Thr Arg Ser Pro Arg Arg Arg Thr Pro Ser Pro Arg Arg Arg
            180                 185                 190

Arg Ser Gln Ser Pro Arg Arg Arg Arg Ser Gln Ser Pro Ala Ser Ser
        195                 200                 205

Asn Cys
    210


<210> SEQ ID NO 5
<211> LENGTH: 170
<212> TYPE: PRT
<213> ORGANISM: Artificial
<220> FEATURE:
```

<223> OTHER INFORMATION: RBHBcAg149 carrier

<400> SEQUENCE: 5

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Gln Asp Ala Ile Val Gln Gln Val Gln Ala
            100                 105                 110

Ser Val Gly Leu Arg Met Arg Gln Leu Met Trp Phe His Leu Ser Cys
        115                 120                 125

Leu Thr Phe Gly Gln Pro Thr Val Ile Glu Phe Leu Val Ser Phe Gly
    130                 135                 140

Thr Trp Ile Arg Thr Pro Gln Ala Tyr Arg Pro Pro Asn Ala Pro Ile
145                 150                 155                 160

Leu Ser Thr Leu Pro Glu His Thr Ile Val
                165                 170
```

<210> SEQ ID NO 6
<211> LENGTH: 209
<212> TYPE: PRT
<213> ORGANISM: Artificial
<220> FEATURE:
<223> OTHER INFORMATION: TBHBcAg188 carrier

<400> SEQUENCE: 6

```
Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Glu Phe Gly Gly
                85                  90                  95

Gly Gly Ser Gly Gly Gly Gly Ser Asp Ala Asp Ala Leu Leu Ala Gly
            100                 105                 110

Tyr Leu Arg Ser Lys Tyr Leu Lys His Ile Thr Lys Ala Ile Trp Tyr
        115                 120                 125

His Leu Ser Cys Leu Thr Phe Gly Lys Gln Thr Val His Glu Tyr Leu
    130                 135                 140

Val Ser Phe Gly Thr Trp Ile Arg Thr Pro Ala Ala Tyr Arg Pro Val
145                 150                 155                 160

Asn Ala Pro Ile Leu Thr Thr Leu Pro Glu Thr Ser Val Ile Arg Arg
                165                 170                 175
```

-continued

```
Arg Pro Ala Ser Arg Arg Ser Thr Pro Ser Pro Arg Arg Arg Arg Ser
            180                 185                 190

Gln Ser Pro Arg Arg Arg Arg Ser Pro Ser Pro Arg Pro Ala Ser Asn
        195                 200                 205

Cys


<210> SEQ ID NO 7
<211> LENGTH: 174
<212> TYPE: PRT
<213> ORGANISM: Artificial
<220> FEATURE:
<223> OTHER INFORMATION: TBHBcAg153 carrier

<400> SEQUENCE: 7

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Glu Phe Gly Gly
                85                  90                  95

Gly Gly Ser Gly Gly Gly Gly Ser Asp Ala Asp Ala Leu Leu Ala Gly
            100                 105                 110

Tyr Leu Arg Ser Lys Tyr Leu Lys His Ile Thr Lys Ala Ile Trp Tyr
        115                 120                 125

His Leu Ser Cys Leu Thr Phe Gly Lys Gln Thr Val His Glu Tyr Leu
    130                 135                 140

Val Ser Phe Gly Thr Trp Ile Arg Thr Pro Ala Ala Tyr Arg Pro Val
145                 150                 155                 160

Asn Ala Pro Ile Leu Thr Thr Leu Pro Glu Thr Ser Val Ile
                165                 170


<210> SEQ ID NO 8
<211> LENGTH: 210
<212> TYPE: PRT
<213> ORGANISM: Artificial
<220> FEATURE:
<223> OTHER INFORMATION: HBHBcAg189 carrier

<400> SEQUENCE: 8

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Glu Phe Gly Gly Gly Gly
                85                  90                  95
```

```
Ser Gly Gly Gly Gly Ser Gln Asp Ala Ile Ile Gly Tyr Val Gln Thr
            100                 105                 110

Thr Val Gly Leu Arg Met Arg Gln Gln Ile Trp Phe His Leu Ser Cys
        115                 120                 125

Leu Thr Phe Gly Gln Gln Thr Val Ile Glu Phe Leu Val Ser Phe Gly
    130                 135                 140

Thr Trp Met Arg Thr Pro Ala Ala Tyr Arg Pro Pro Asn Ala Pro Ile
145                 150                 155                 160

Leu Ser Thr Leu Pro Glu His Thr Val Ile Arg Arg Arg Gly Asn Pro
                165                 170                 175

Arg Ala Pro Arg Ser Pro Arg Arg Arg Thr Pro Ser Pro Arg Arg Arg
            180                 185                 190

Arg Ser Gln Ser Pro Arg Arg Arg Arg Ser Gln Ser Pro Ala Pro Ser
        195                 200                 205

Asn Cys
    210


<210> SEQ ID NO 9
<211> LENGTH: 170
<212> TYPE: PRT
<213> ORGANISM: Artificial
<220> FEATURE:
<223> OTHER INFORMATION: HBHBcAg149 carrier

<400> SEQUENCE: 9

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Gln Asp Ala Ile Ile Gly Tyr Val Gln Thr
            100                 105                 110

Thr Val Gly Leu Arg Met Arg Gln Gln Ile Trp Phe His Leu Ser Cys
        115                 120                 125

Leu Thr Phe Gly Gln Gln Thr Val Ile Glu Phe Leu Val Ser Phe Gly
    130                 135                 140

Thr Trp Met Arg Thr Pro Ala Ala Tyr Arg Pro Pro Asn Ala Pro Ile
145                 150                 155                 160

Leu Ser Thr Leu Pro Glu His Thr Val Ile
                165                 170


<210> SEQ ID NO 10
<211> LENGTH: 204
<212> TYPE: PRT
<213> ORGANISM: Artificial
<220> FEATURE:
<223> OTHER INFORMATION: HBcAg183 carrier

<400> SEQUENCE: 10

Met Asp Ile Asp Pro Tyr Lys Glu Phe Gly Ala Ser Val Glu Leu Leu
```

-continued

```
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Arg Glu Leu Val Val Ser Tyr Val Asn Val
            100                 105                 110

Asn Met Gly Leu Lys Ile Arg Gln Leu Leu Trp Phe His Ile Ser Cys
        115                 120                 125

Leu Thr Phe Gly Arg Glu Thr Val Leu Glu Tyr Leu Val Ser Phe Gly
    130                 135                 140

Val Trp Ile Arg Thr Pro Pro Ala Tyr Arg Pro Gln Asn Ala Pro Ile
145                 150                 155                 160

Leu Ser Thr Leu Pro Glu Thr Thr Val Val Arg Arg Arg Gly Arg Ser
                165                 170                 175

Pro Arg Arg Arg Thr Pro Ser Pro Arg Arg Arg Arg Ser Gln Ser Pro
            180                 185                 190

Arg Arg Arg Arg Ser Gln Ser Arg Glu Ser Gln Cys
        195                 200


<210> SEQ ID NO 11
<211> LENGTH: 170
<212> TYPE: PRT
<213> ORGANISM: Artificial
<220> FEATURE:
<223> OTHER INFORMATION: HBcAg149 carrier

<400> SEQUENCE: 11

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Arg Glu Leu Val Val Ser Tyr Val Asn Val
            100                 105                 110

Asn Met Gly Leu Lys Ile Arg Gln Leu Leu Trp Phe His Ile Ser Cys
        115                 120                 125

Leu Thr Phe Gly Arg Glu Thr Val Leu Glu Tyr Leu Val Ser Phe Gly
    130                 135                 140

Val Trp Ile Arg Thr Pro Pro Ala Tyr Arg Pro Gln Asn Ala Pro Ile
145                 150                 155                 160

Leu Ser Thr Leu Pro Glu Thr Thr Val Val
```

-continued 165 170

<210> SEQ ID NO 12
<211> LENGTH: 633
<212> TYPE: DNA
<213> ORGANISM: Artificial
<220> FEATURE:
<223> OTHER INFORMATION: nucleotide sequence encoding RBHBcAg189 carrier

<400> SEQUENCE: 12
atggacattg atccttataa agaatttgga gcttcatctc aactgatctc tttcttgcct 60
gaggactttt tcccaaacct tgcagaattg gtcgagacca ccacagctct ctatgaagaa 120
gaattagtag gtaaggagca ttgctcccct caccatactg ctttacgatc cttgctaaat 180
tgctggggag agactgttag attaataact tgggtcagga actctgtgga gggaggtgga 240
ggtggttctg gaggtggtgg tactggatcc gaattcggtg gtggaggttc aggaggaggt 300
ggttcccaag atgccattgt ccagcaagtt caggcctcgg tgggcctgcg catgagacag 360
ttaatgtggt tccatctctc atgcctaaca tttggacagc ccactgtcat agaatttctg 420
gtctcttttg gaacatggat cagaaccccg caagcttaca gaccccctaa tgcacccatt 480
ctctcgactc ttccggagca tacaatcgtt aggagaagag gaggttcacg cgctactagg 540
tccccccgaa ggcgcactcc ctctcctcgc cgacgcagat ctcaatcgcc gcgtcgccgc 600
agatctcagt ctccagcttc ctccaactgc taa 633

<210> SEQ ID NO 13
<211> LENGTH: 510
<212> TYPE: DNA
<213> ORGANISM: Artificial
<220> FEATURE:
<223> OTHER INFORMATION: nucleotide sequence encoding RBHBcAg149 carrier

<400> SEQUENCE: 13
atggacattg atccttataa agaatttgga gcttcatctc aactgatctc tttcttgcct 60
gaggactttt tcccaaacct tgcagaattg gtcgagacca ccacagctct ctatgaagaa 120
gaattagtag gtaaggagca ttgctcccct caccatactg ctttacgatc cttgctaaat 180
tgctggggag agactgttag attaataact tgggtcagga actctgtgga gggaggtgga 240
ggtggttctg gaggtggtgg tactggatcc gaattcggtg gtggaggttc aggaggaggt 300
ggttcccaag atgccattgt ccagcaagtt caggcctcgg tgggcctgcg catgagacag 360
ttaatgtggt tccatctctc atgcctaaca tttggacagc ccactgtcat agaatttctg 420
gtctcttttg gaacatggat cagaaccccg caagcttaca gaccccctaa tgcacccatt 480
ctctcgactc ttccggagca tacaatcgtt 510

<210> SEQ ID NO 14
<211> LENGTH: 630
<212> TYPE: DNA
<213> ORGANISM: Artificial
<220> FEATURE:
<223> OTHER INFORMATION: nucleotide sequence encoding TBHBcAg188 carrier

<400> SEQUENCE: 14
atggaaaacc ttgaaagact tgacatctat aaagaatttg gagtctctga tgtcttggtg 60
tctttcttac ctgatgattt ctttccaact ttacagcaac ttttggaatc agtgaatgcc 120
ctatatgagg atgaactcac tgggcctaat cactgttctc cccatcatac tgccttaagg 180
cacttgatta tgtgtggggt agaattaaga gattttattg attggatgca tgaacagggg 240
ggtggaggtg gttctggagg tggtggtact ggatccgaat tcggtggtgg aggttcagga 300
ggaggtggtt ccgatgcaga cgctcttttg gctggttacc ttcgatccaa atatcttaaa 360
catattacca aggctatttg gtatcattta agctgtttga cctttggtaa gcaaacagtg 420
catgaatacc tggtatcctt tggcacctgg atcagaaccc cagctgcata tagaccagtg 480
aatgcaccca ttctcaccac tcttccggaa acttcagtta tcagaagaag gcctgcctcc 540
agaagatcta ctccctctcc tcgcagacgc cgatctcaat caccgcgccg ccgccgctct 600
ccatctccaa gaccagcaag caattgctga 630

<210> SEQ ID NO 15
<211> LENGTH: 522
<212> TYPE: DNA
<213> ORGANISM: Artificial
<220> FEATURE:
<223> OTHER INFORMATION: nucleotide sequence encoding TBHBcAg153 carrier

<400> SEQUENCE: 15
atggaaaacc ttgaaagact tgacatctat aaagaatttg gagtctctga tgtcttggtg 60
tctttcttac ctgatgattt ctttccaact ttacagcaac ttttggaatc agtgaatgcc 120
ctatatgagg atgaactcac tggcctaat cactgttctc cccatcatac tgccttaagg 180
cacttgatta tgtgtggggt agaattaaga gattttattg attggatgca tgaacagggg 240
ggtggaggtg gttctggagg tggtggtact ggatccgaat tcggtggtgg aggttcagga 300
ggaggtggtt ccgatgcaga cgctcttttg gctggttacc ttcgatccaa atatcttaaa 360
catattacca aggctatttg gtatcattta agctgtttga cctttggtaa gcaaacagtg 420
catgaatacc tggtatcctt tggcacctgg atcagaaccc cagctgcata tagaccagtg 480
aatgcaccca ttctcaccac tcttccggaa acttcagtta tc 522

<210> SEQ ID NO 16
<211> LENGTH: 633
<212> TYPE: DNA
<213> ORGANISM: Artificial
<220> FEATURE:
<223> OTHER INFORMATION: nucleotide sequence encoding HBHBcAg189 carrier

<400> SEQUENCE: 16
atggacattg atccttataa agagttcggt gcttcatctc aacttgtctc ctttttgcct 60
gctgacttct ttcccgcctt gaacgacctg gtggaaactt cggtggcctt atatgaggaa 120
gaccttgtag gtaaggagca ttgctcccct catcatgcag ccttaagggc cctacttaat 180
tgctgggagg aaacagtcag actgattacc tgggtccgtg ccacagtaga gggaggtgga 240
ggtggttctg gaggtggtgg tactggatcc gaattcggtg gtggaggttc aggaggaggt 300
ggttcccagg atgccatcat cggttatgtc cagactacgg tgggcctacg catgagacaa 360
cagatctggt tccatctctc atgccttact tttgggcagc agactgtgat agagttcctg 420
gtctcatttg ggacatggat gagaactcca gccgcctata gaccccccaa tgcacccatt 480
ttatcaactc ttccagagca cacagtcatt aggagaagag gaaatccgcg tgctcctagg 540
tcccccagaa ggcgcactcc ctctcctcgc cgacgcagat ctcaatctcc gcgtcgccgg 600
agatctcaat ctccagctcc ctccaactgc taa 633

<210> SEQ ID NO 17
<211> LENGTH: 510
<212> TYPE: DNA

<213> ORGANISM: Artificial
<220> FEATURE:
<223> OTHER INFORMATION: nucleotide sequence encoding HBHBcAg149 carrier

<400> SEQUENCE: 17
atggacattg atccttataa agagttcggt gcttcatctc aacttgtctc ctttttgcct 60
gctgacttct ttcccgcctt gaacgacctg gtggaaactt cggtggcctt atatgaggaa 120
gaccttgtag gtaaggagca ttgctcccct catcatgcag ccttaagggc cctacttaat 180
tgctgggagg aaacagtcag actgattacc tgggtccgtg ccacagtaga gggaggtgga 240
ggtggttctg gaggtggtgg tactggatcc gaattcggtg gtggaggttc aggaggaggt 300
ggttcccagg atgccatcat cggttatgtc cagactacgg tgggcctacg catgagacaa 360
cagatctggt tccatctctc atgccttact tttgggcagc agactgtgat agagttcctg 420
gtctcatttg ggacatggat gagaactcca gccgcctata gaccccccaa tgcacccatt 480
ttatcaactc ttccagagca cacagtcatt 510

<210> SEQ ID NO 18
<211> LENGTH: 615
<212> TYPE: DNA
<213> ORGANISM: Artificial
<220> FEATURE:
<223> OTHER INFORMATION: nucleotide sequence encoding HBcAg183 carrier

<400> SEQUENCE: 18
atggacattg atccatataa agaatttgga gcttctgtgg agttactctc tttttttgcct 60 tccgacttct ttccttctat ccgagatctc ctcgacaccg cctctgctct gtatcgggag 120
gccttagagt ctccggaaca ttgttcacct caccatacgg cactcaggca agctattctg 180
tgttggggtg agttgatgaa tctagccacc tgggtgggaa gtaatttgga agatggtgga 240
ggtggttctg gaggtggtgg tactggatcc gaattcggtg gtggaggttc aggaggaggt 300
ggttccaggg aactagtagt cagctatgtc aacgttaata tgggcctaaa aatcagacaa 360
ctattgtggt ttcacatttc ctgtcttact tttgggagag aaactgttct tgaatatttg 420
gtgtcttttg gagtgtggat tcgcactcct cctgcatata gaccacaaaa tgcccctatc 480
ttatcaacac ttccggaaac tactgttgtt cgtcgccgag gccgtagccc gcgacgacgt 540
accccgagcc cgcgtcgacg tcgcagccag agcccgcgcc gtcgtcgcag ccagagccgt 600
gaaagccagt gctaa 615

<210> SEQ ID NO 19
<211> LENGTH: 510
<212> TYPE: DNA
<213> ORGANISM: Artificial
<220> FEATURE:
<223> OTHER INFORMATION: nucleotide sequence encoding HBcAg149 carrier

<400> SEQUENCE: 19
atggacattg atccatataa agaatttgga gcttctgtgg agttactctc tttttttgcct 60 tccgacttct ttccttctat ccgagatctc ctcgacaccg cctctgctct gtatcgggag 120
gccttagagt ctccggaaca ttgttcacct caccatacgg cactcaggca agctattctg 180
tgttggggtg agttgatgaa tctagccacc tgggtgggaa gtaatttgga agatggtgga 240
ggtggttctg gaggtggtgg tactggatcc gaattcggtg gtggaggttc aggaggaggt 300
ggttccaggg aactagtagt cagctatgtc aacgttaata tgggcctaaa aatcagacaa 360
ctattgtggt ttcacatttc ctgtcttact tttgggagag aaactgttct tgaatatttg 420

```
gtgtcttttg gagtgtggat tcgcactcct cctgcatata gaccacaaaa tgcccctatc    480

ttatcaacac ttccggaaac tactgttgtt                                     510


<210> SEQ ID NO 20
<211> LENGTH: 15
<212> TYPE: PRT
<213> ORGANISM: HIV

<400> SEQUENCE: 20

Phe Lys Gln Ser Ser Gly Gly Asp Pro Glu Ile Val Thr His Ser
1               5                   10                  15


<210> SEQ ID NO 21
<211> LENGTH: 14
<212> TYPE: PRT
<213> ORGANISM: Homo sapiens

<400> SEQUENCE: 21

Thr Ser Glu His Glu Leu Thr Cys Gln Ala Glu Gly Tyr Pro
1               5                   10


<210> SEQ ID NO 22
<211> LENGTH: 23
<212> TYPE: PRT
<213> ORGANISM: HBV

<400> SEQUENCE: 22

Ser Ser Thr Thr Ser Thr Gly Pro Cys Lys Thr Cys Thr Thr Pro Ala
1               5                   10                  15

Gln Gly Thr Ser Met Phe Pro
            20


<210> SEQ ID NO 23
<211> LENGTH: 225
<212> TYPE: PRT
<213> ORGANISM: Artificial
<220> FEATURE:
<223> OTHER INFORMATION: Recombinant protein RBHBcAg189-SEQ20

<400> SEQUENCE: 23

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Gly Ser
            100                 105                 110

Gly Gly Gly Gly Ser Gln Asp Ala Ile Val Gln Gln Val Gln Ala Ser
        115                 120                 125

Val Gly Leu Arg Met Arg Gln Leu Met Trp Phe His Leu Ser Cys Leu
    130                 135                 140

Thr Phe Gly Gln Pro Thr Val Ile Glu Phe Leu Val Ser Phe Gly Thr
```

-continued

```
145                 150                 155                 160

Trp Ile Arg Thr Pro Gln Ala Tyr Arg Pro Pro Asn Ala Pro Ile Leu
                165                 170                 175

Ser Thr Leu Pro Glu His Thr Ile Val Arg Arg Arg Gly Gly Ser Arg
            180                 185                 190

Ala Thr Arg Ser Pro Arg Arg Arg Thr Pro Ser Pro Arg Arg Arg Arg
        195                 200                 205

Ser Gln Ser Pro Arg Arg Arg Arg Ser Gln Ser Pro Ala Ser Ser Asn
    210                 215                 220

Cys
225


<210> SEQ ID NO 24
<211> LENGTH: 185
<212> TYPE: PRT
<213> ORGANISM: Artificial
<220> FEATURE:
<223> OTHER INFORMATION: Recombinant protein RBHBcAg149-SEQ20

<400> SEQUENCE: 24

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Gly Ser
            100                 105                 110

Gly Gly Gly Gly Ser Gln Asp Ala Ile Val Gln Gln Val Gln Ala Ser
        115                 120                 125

Val Gly Leu Arg Met Arg Gln Leu Met Trp Phe His Leu Ser Cys Leu
    130                 135                 140

Thr Phe Gly Gln Pro Thr Val Ile Glu Phe Leu Val Ser Phe Gly Thr
145                 150                 155                 160

Trp Ile Arg Thr Pro Gln Ala Tyr Arg Pro Pro Asn Ala Pro Ile Leu
                165                 170                 175

Ser Thr Leu Pro Glu His Thr Ile Val
            180                 185


<210> SEQ ID NO 25
<211> LENGTH: 224
<212> TYPE: PRT
<213> ORGANISM: Artificial
<220> FEATURE:
<223> OTHER INFORMATION: Recombinant protein TBHBcAg188-SEQ20

<400> SEQUENCE: 25

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30
```

-continued

```
Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Phe Lys Gln Ser
                85                  90                  95

Ser Gly Gly Asp Pro Glu Ile Val Thr His Ser Glu Phe Gly Gly Gly
            100                 105                 110

Gly Ser Gly Gly Gly Gly Ser Asp Ala Asp Ala Leu Leu Ala Gly Tyr
        115                 120                 125

Leu Arg Ser Lys Tyr Leu Lys His Ile Thr Lys Ala Ile Trp Tyr His
    130                 135                 140

Leu Ser Cys Leu Thr Phe Gly Lys Gln Thr Val His Glu Tyr Leu Val
145                 150                 155                 160

Ser Phe Gly Thr Trp Ile Arg Thr Pro Ala Ala Tyr Arg Pro Val Asn
                165                 170                 175

Ala Pro Ile Leu Thr Thr Leu Pro Glu Thr Ser Val Ile Arg Arg Arg
            180                 185                 190

Pro Ala Ser Arg Arg Ser Thr Pro Ser Pro Arg Arg Arg Arg Ser Gln
        195                 200                 205

Ser Pro Arg Arg Arg Arg Ser Pro Ser Pro Arg Pro Ala Ser Asn Cys
    210                 215                 220


<210> SEQ ID NO 26
<211> LENGTH: 189
<212> TYPE: PRT
<213> ORGANISM: Artificial
<220> FEATURE:
<223> OTHER INFORMATION: Recombinant protein TBHBcAg153-SEQ20

<400> SEQUENCE: 26

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Phe Lys Gln Ser
                85                  90                  95

Ser Gly Gly Asp Pro Glu Ile Val Thr His Ser Glu Phe Gly Gly Gly
            100                 105                 110

Gly Ser Gly Gly Gly Gly Ser Asp Ala Asp Ala Leu Leu Ala Gly Tyr
        115                 120                 125

Leu Arg Ser Lys Tyr Leu Lys His Ile Thr Lys Ala Ile Trp Tyr His
    130                 135                 140

Leu Ser Cys Leu Thr Phe Gly Lys Gln Thr Val His Glu Tyr Leu Val
145                 150                 155                 160

Ser Phe Gly Thr Trp Ile Arg Thr Pro Ala Ala Tyr Arg Pro Val Asn
                165                 170                 175
```

```
Ala Pro Ile Leu Thr Thr Leu Pro Glu Thr Ser Val Ile
            180                 185


<210> SEQ ID NO 27
<211> LENGTH: 225
<212> TYPE: PRT
<213> ORGANISM: Artificial
<220> FEATURE:
<223> OTHER INFORMATION: Recombinant protein HBHBcAg189-SEQ20

<400> SEQUENCE: 27

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Gly Ser
            100                 105                 110

Gly Gly Gly Gly Ser Gln Asp Ala Ile Ile Gly Tyr Val Gln Thr Thr
        115                 120                 125

Val Gly Leu Arg Met Arg Gln Gln Ile Trp Phe His Leu Ser Cys Leu
    130                 135                 140

Thr Phe Gly Gln Gln Thr Val Ile Glu Phe Leu Val Ser Phe Gly Thr
145                 150                 155                 160

Trp Met Arg Thr Pro Ala Ala Tyr Arg Pro Pro Asn Ala Pro Ile Leu
                165                 170                 175

Ser Thr Leu Pro Glu His Thr Val Ile Arg Arg Arg Gly Asn Pro Arg
            180                 185                 190

Ala Pro Arg Ser Pro Arg Arg Arg Thr Pro Ser Pro Arg Arg Arg Arg
        195                 200                 205

Ser Gln Ser Pro Arg Arg Arg Arg Ser Gln Ser Pro Ala Pro Ser Asn
    210                 215                 220

Cys
225


<210> SEQ ID NO 28
<211> LENGTH: 185
<212> TYPE: PRT
<213> ORGANISM: Artificial
<220> FEATURE:
<223> OTHER INFORMATION: Recombinant protein HBHBcAg149-SEQ20

<400> SEQUENCE: 28

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60
```

```
Thr Val Arg Leu Ile Thr Trp Val Arg Ala Thr Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Gly Ser
            100                 105                 110

Gly Gly Gly Gly Ser Gln Asp Ala Ile Ile Gly Tyr Val Gln Thr Thr
        115                 120                 125

Val Gly Leu Arg Met Arg Gln Gln Ile Trp Phe His Leu Ser Cys Leu
    130                 135                 140

Thr Phe Gly Gln Gln Thr Val Ile Glu Phe Leu Val Ser Phe Gly Thr
145                 150                 155                 160

Trp Met Arg Thr Pro Ala Ala Tyr Arg Pro Pro Asn Ala Pro Ile Leu
                165                 170                 175

Ser Thr Leu Pro Glu His Thr Val Ile
            180                 185
```

<210> SEQ ID NO 29
<211> LENGTH: 224
<212> TYPE: PRT
<213> ORGANISM: Artificial
<220> FEATURE:
<223> OTHER INFORMATION: Recombinant protein RBHBcAg189-SEQ21

<400> SEQUENCE: 29

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Thr Ser Glu His Glu Leu
                85                  90                  95

Thr Cys Gln Ala Glu Gly Tyr Pro Glu Phe Gly Gly Gly Gly Ser Gly
            100                 105                 110

Gly Gly Gly Ser Gln Asp Ala Ile Val Gln Gln Val Gln Ala Ser Val
        115                 120                 125

Gly Leu Arg Met Arg Gln Leu Met Trp Phe His Leu Ser Cys Leu Thr
    130                 135                 140

Phe Gly Gln Pro Thr Val Ile Glu Phe Leu Val Ser Phe Gly Thr Trp
145                 150                 155                 160

Ile Arg Thr Pro Gln Ala Tyr Arg Pro Pro Asn Ala Pro Ile Leu Ser
                165                 170                 175

Thr Leu Pro Glu His Thr Ile Val Arg Arg Arg Gly Gly Ser Arg Ala
            180                 185                 190

Thr Arg Ser Pro Arg Arg Arg Thr Pro Ser Pro Arg Arg Arg Arg Ser
        195                 200                 205

Gln Ser Pro Arg Arg Arg Arg Ser Gln Ser Pro Ala Ser Ser Asn Cys
    210                 215                 220
```

<210> SEQ ID NO 30

<211> LENGTH: 184
<212> TYPE: PRT
<213> ORGANISM: Artificial
<220> FEATURE:
<223> OTHER INFORMATION: Recombinant protein RBHBcAg149-SEQ21

<400> SEQUENCE: 30

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Thr Ser Glu His Glu Leu
                85                  90                  95

Thr Cys Gln Ala Glu Gly Tyr Pro Glu Phe Gly Gly Gly Gly Ser Gly
            100                 105                 110

Gly Gly Gly Ser Gln Asp Ala Ile Val Gln Gln Val Gln Ala Ser Val
        115                 120                 125

Gly Leu Arg Met Arg Gln Leu Met Trp Phe His Leu Ser Cys Leu Thr
    130                 135                 140

Phe Gly Gln Pro Thr Val Ile Glu Phe Leu Val Ser Phe Gly Thr Trp
145                 150                 155                 160

Ile Arg Thr Pro Gln Ala Tyr Arg Pro Pro Asn Ala Pro Ile Leu Ser
                165                 170                 175

Thr Leu Pro Glu His Thr Ile Val
            180
```

<210> SEQ ID NO 31
<211> LENGTH: 223
<212> TYPE: PRT
<213> ORGANISM: Artificial
<220> FEATURE:
<223> OTHER INFORMATION: Recombinant protein TBHBcAg188-SEQ21

<400> SEQUENCE: 31

```
Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Thr Ser Glu His
                85                  90                  95

Glu Leu Thr Cys Gln Ala Glu Gly Tyr Pro Glu Phe Gly Gly Gly Gly
            100                 105                 110

Ser Gly Gly Gly Gly Ser Asp Ala Asp Ala Leu Leu Ala Gly Tyr Leu
        115                 120                 125

Arg Ser Lys Tyr Leu Lys His Ile Thr Lys Ala Ile Trp Tyr His Leu
```

```
    130                 135                 140

Ser Cys Leu Thr Phe Gly Lys Gln Thr Val His Glu Tyr Leu Val Ser
145                 150                 155                 160

Phe Gly Thr Trp Ile Arg Thr Pro Ala Ala Tyr Arg Pro Val Asn Ala
                165                 170                 175

Pro Ile Leu Thr Thr Leu Pro Glu Thr Ser Val Ile Arg Arg Arg Pro
            180                 185                 190

Ala Ser Arg Arg Ser Thr Pro Ser Pro Arg Arg Arg Arg Ser Gln Ser
        195                 200                 205

Pro Arg Arg Arg Arg Ser Pro Ser Pro Arg Pro Ala Ser Asn Cys
    210                 215                 220


<210> SEQ ID NO 32
<211> LENGTH: 188
<212> TYPE: PRT
<213> ORGANISM: Artificial
<220> FEATURE:
<223> OTHER INFORMATION: Recombinant protein TBHBcAg153-SEQ21

<400> SEQUENCE: 32

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Thr Ser Glu His
                85                  90                  95

Glu Leu Thr Cys Gln Ala Glu Gly Tyr Pro Glu Phe Gly Gly Gly Gly
            100                 105                 110

Ser Gly Gly Gly Gly Ser Asp Ala Asp Ala Leu Leu Ala Gly Tyr Leu
        115                 120                 125

Arg Ser Lys Tyr Leu Lys His Ile Thr Lys Ala Ile Trp Tyr His Leu
    130                 135                 140

Ser Cys Leu Thr Phe Gly Lys Gln Thr Val His Glu Tyr Leu Val Ser
145                 150                 155                 160

Phe Gly Thr Trp Ile Arg Thr Pro Ala Ala Tyr Arg Pro Val Asn Ala
                165                 170                 175

Pro Ile Leu Thr Thr Leu Pro Glu Thr Ser Val Ile
            180                 185


<210> SEQ ID NO 33
<211> LENGTH: 224
<212> TYPE: PRT
<213> ORGANISM: Artificial
<220> FEATURE:
<223> OTHER INFORMATION: Recombinant protein HBHBcAg189-SEQ21

<400> SEQUENCE: 33

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30
```

```
Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Thr Ser Glu His Glu Leu
                85                  90                  95

Thr Cys Gln Ala Glu Gly Tyr Pro Glu Phe Gly Gly Gly Gly Ser Gly
            100                 105                 110

Gly Gly Gly Ser Gln Asp Ala Ile Ile Gly Tyr Val Gln Thr Thr Val
        115                 120                 125

Gly Leu Arg Met Arg Gln Gln Ile Trp Phe His Leu Ser Cys Leu Thr
    130                 135                 140

Phe Gly Gln Gln Thr Val Ile Glu Phe Leu Val Ser Phe Gly Thr Trp
145                 150                 155                 160

Met Arg Thr Pro Ala Ala Tyr Arg Pro Pro Asn Ala Pro Ile Leu Ser
                165                 170                 175

Thr Leu Pro Glu His Thr Val Ile Arg Arg Arg Gly Asn Pro Arg Ala
            180                 185                 190

Pro Arg Ser Pro Arg Arg Arg Thr Pro Ser Pro Arg Arg Arg Arg Ser
        195                 200                 205

Gln Ser Pro Arg Arg Arg Arg Ser Gln Ser Pro Ala Pro Ser Asn Cys
    210                 215                 220


<210> SEQ ID NO 34
<211> LENGTH: 184
<212> TYPE: PRT
<213> ORGANISM: Artificial
<220> FEATURE:
<223> OTHER INFORMATION: Recombinant protein HBHBcAg149-SEQ21

<400> SEQUENCE: 34

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Thr Ser Glu His Glu Leu
                85                  90                  95

Thr Cys Gln Ala Glu Gly Tyr Pro Glu Phe Gly Gly Gly Gly Ser Gly
            100                 105                 110

Gly Gly Gly Ser Gln Asp Ala Ile Ile Gly Tyr Val Gln Thr Thr Val
        115                 120                 125

Gly Leu Arg Met Arg Gln Gln Ile Trp Phe His Leu Ser Cys Leu Thr
    130                 135                 140

Phe Gly Gln Gln Thr Val Ile Glu Phe Leu Val Ser Phe Gly Thr Trp
145                 150                 155                 160

Met Arg Thr Pro Ala Ala Tyr Arg Pro Pro Asn Ala Pro Ile Leu Ser
                165                 170                 175
```

Thr Leu Pro Glu His Thr Val Ile
180

<210> SEQ ID NO 35
<211> LENGTH: 233
<212> TYPE: PRT
<213> ORGANISM: Artificial
<220> FEATURE:
<223> OTHER INFORMATION: Recombinant protein RBHBcAg189-SEQ22

<400> SEQUENCE: 35

Met Asp Ile Asp Pro Tyr Lys Glu Phe Gly Ala Ser Ser Gln Leu Ile
1 5 10 15

Ser Phe Leu Pro Glu Asp Phe Phe Pro Asn Leu Ala Glu Leu Val Glu
20 25 30

Thr Thr Thr Ala Leu Tyr Glu Glu Glu Leu Val Gly Lys Glu His Cys
35 40 45

Ser Pro His His Thr Ala Leu Arg Ser Leu Leu Asn Cys Trp Gly Glu
50 55 60

Thr Val Arg Leu Ile Thr Trp Val Arg Asn Ser Val Glu Gly Gly Gly
65 70 75 80

Gly Gly Ser Gly Gly Gly Gly Thr Gly Ser Ser Ser Thr Thr Ser Thr
85 90 95

Gly Pro Cys Lys Thr Cys Thr Thr Pro Ala Gln Gly Thr Ser Met Phe
100 105 110

Pro Glu Phe Gly Gly Gly Gly Ser Gly Gly Gly Gly Ser Gln Asp Ala
115 120 125

Ile Val Gln Gln Val Gln Ala Ser Val Gly Leu Arg Met Arg Gln Leu
130 135 140

Met Trp Phe His Leu Ser Cys Leu Thr Phe Gly Gln Pro Thr Val Ile
145 150 155 160

Glu Phe Leu Val Ser Phe Gly Thr Trp Ile Arg Thr Pro Gln Ala Tyr
165 170 175

Arg Pro Pro Asn Ala Pro Ile Leu Ser Thr Leu Pro Glu His Thr Ile
180 185 190

Val Arg Arg Arg Gly Gly Ser Arg Ala Thr Arg Ser Pro Arg Arg Arg
195 200 205

Thr Pro Ser Pro Arg Arg Arg Arg Ser Gln Ser Pro Arg Arg Arg Arg
210 215 220

Ser Gln Ser Pro Ala Ser Ser Asn Cys
225 230

<210> SEQ ID NO 36
<211> LENGTH: 193
<212> TYPE: PRT
<213> ORGANISM: Artificial
<220> FEATURE:
<223> OTHER INFORMATION: Recombinant protein RBHBcAg149-SEQ22

<400> SEQUENCE: 36

Met Asp Ile Asp Pro Tyr Lys Glu Phe Gly Ala Ser Ser Gln Leu Ile
1 5 10 15

Ser Phe Leu Pro Glu Asp Phe Phe Pro Asn Leu Ala Glu Leu Val Glu
20 25 30

Thr Thr Thr Ala Leu Tyr Glu Glu Glu Leu Val Gly Lys Glu His Cys
35 40 45

Ser Pro His His Thr Ala Leu Arg Ser Leu Leu Asn Cys Trp Gly Glu
50 55 60

```
Thr Val Arg Leu Ile Thr Trp Val Arg Asn Ser Val Glu Gly Gly Gly
65                  70                  75                  80

Gly Gly Ser Gly Gly Gly Gly Thr Gly Ser Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Gln Asp Ala
        115                 120                 125

Ile Val Gln Gln Val Gln Ala Ser Val Gly Leu Arg Met Arg Gln Leu
    130                 135                 140

Met Trp Phe His Leu Ser Cys Leu Thr Phe Gly Gln Pro Thr Val Ile
145                 150                 155                 160

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190

Val


<210> SEQ ID NO 37
<211> LENGTH: 232
<212> TYPE: PRT
<213> ORGANISM: Artificial
<220> FEATURE:
<223> OTHER INFORMATION: Recombinant protein TBHBcAg188-SEQ22

<400> SEQUENCE: 37

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Ser Ser Thr Thr
                85                  90                  95

Ser Thr Gly Pro Cys Lys Thr Cys Thr Thr Pro Ala Gln Gly Thr Ser
            100                 105                 110

Met Phe Pro Glu Phe Gly Gly Gly Gly Ser Gly Gly Gly Gly Ser Asp
        115                 120                 125

Ala Asp Ala Leu Leu Ala Gly Tyr Leu Arg Ser Lys Tyr Leu Lys His
    130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile Arg Arg Arg Pro Ala Ser Arg Arg Ser Thr Pro
        195                 200                 205

Ser Pro Arg Arg Arg Arg Ser Gln Ser Pro Arg Arg Arg Arg Ser Pro
    210                 215                 220
```

Ser Pro Arg Pro Ala Ser Asn Cys
225 230

<210> SEQ ID NO 38
<211> LENGTH: 197
<212> TYPE: PRT
<213> ORGANISM: Artificial
<220> FEATURE:
<223> OTHER INFORMATION: Recombinant protein TBHBcAg153-SEQ22

<400> SEQUENCE: 38

Met Glu Asn Leu Glu Arg Leu Asp Ile Tyr Lys Glu Phe Gly Val Ser
1 5 10 15

Asp Val Leu Val Ser Phe Leu Pro Asp Asp Phe Phe Pro Thr Leu Gln
20 25 30

Gln Leu Leu Glu Ser Val Asn Ala Leu Tyr Glu Asp Glu Leu Thr Gly
35 40 45

Pro Asn His Cys Ser Pro His His Thr Ala Leu Arg His Leu Ile Met
50 55 60

Cys Gly Val Glu Leu Arg Asp Phe Ile Asp Trp Met His Glu Gln Gly
65 70 75 80

Gly Gly Gly Gly Ser Gly Gly Gly Gly Thr Gly Ser Ser Ser Thr Thr
85 90 95

Ser Thr Gly Pro Cys Lys Thr Cys Thr Thr Pro Ala Gln Gly Thr Ser
100 105 110

Met Phe Pro Glu Phe Gly Gly Gly Gly Ser Gly Gly Gly Gly Ser Asp
115 120 125

Ala Asp Ala Leu Leu Ala Gly Tyr Leu Arg Ser Lys Tyr Leu Lys His
130 135 140

Ile Thr Lys Ala Ile Trp Tyr His Leu Ser Cys Leu Thr Phe Gly Lys
145 150 155 160

Gln Thr Val His Glu Tyr Leu Val Ser Phe Gly Thr Trp Ile Arg Thr
165 170 175

Pro Ala Ala Tyr Arg Pro Val Asn Ala Pro Ile Leu Thr Thr Leu Pro
180 185 190

Glu Thr Ser Val Ile
195

<210> SEQ ID NO 39
<211> LENGTH: 233
<212> TYPE: PRT
<213> ORGANISM: Artificial
<220> FEATURE:
<223> OTHER INFORMATION: Recombinant protein HBHBcAg189-SEQ22

<400> SEQUENCE: 39

Met Asp Ile Asp Pro Tyr Lys Glu Phe Gly Ala Ser Ser Gln Leu Val
1 5 10 15

Ser Phe Leu Pro Ala Asp Phe Phe Pro Ala Leu Asn Asp Leu Val Glu
20 25 30

Thr Ser Val Ala Leu Tyr Glu Glu Asp Leu Val Gly Lys Glu His Cys
35 40 45

Ser Pro His His Ala Ala Leu Arg Ala Leu Leu Asn Cys Trp Glu Glu
50 55 60

Thr Val Arg Leu Ile Thr Trp Val Arg Ala Thr Val Glu Gly Gly Gly
65 70 75 80

Gly Gly Ser Gly Gly Gly Gly Thr Gly Ser Ser Ser Thr Thr Ser Thr
85 90 95

```
Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Gln Asp Ala
        115                 120                 125

Ile Ile Gly Tyr Val Gln Thr Thr Val Gly Leu Arg Met Arg Gln Gln
    130                 135                 140

Ile Trp Phe His Leu Ser Cys Leu Thr Phe Gly Gln Gln Thr Val Ile
145                 150                 155                 160

Glu Phe Leu Val Ser Phe Gly Thr Trp Met Arg Thr Pro Ala Ala Tyr
                165                 170                 175

Arg Pro Pro Asn Ala Pro Ile Leu Ser Thr Leu Pro Glu His Thr Val
            180                 185                 190

Ile Arg Arg Arg Gly Asn Pro Arg Ala Pro Arg Ser Pro Arg Arg Arg
        195                 200                 205

Thr Pro Ser Pro Arg Arg Arg Arg Ser Gln Ser Pro Arg Arg Arg Arg
    210                 215                 220

Ser Gln Ser Pro Ala Pro Ser Asn Cys
225                 230


<210> SEQ ID NO 40
<211> LENGTH: 193
<212> TYPE: PRT
<213> ORGANISM: Artificial
<220> FEATURE:
<223> OTHER INFORMATION: Recombinant protein HBHBcAg149-SEQ22

<400> SEQUENCE: 40

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Gln Asp Ala
        115                 120                 125

Ile Ile Gly Tyr Val Gln Thr Thr Val Gly Leu Arg Met Arg Gln Gln
    130                 135                 140

Ile Trp Phe His Leu Ser Cys Leu Thr Phe Gly Gln Gln Thr Val Ile
145                 150                 155                 160

Glu Phe Leu Val Ser Phe Gly Thr Trp Met Arg Thr Pro Ala Ala Tyr
                165                 170                 175

Arg Pro Pro Asn Ala Pro Ile Leu Ser Thr Leu Pro Glu His Thr Val
            180                 185                 190

Ile


<210> SEQ ID NO 41
<211> LENGTH: 227
```

```
<212> TYPE: PRT
<213> ORGANISM: Artificial
<220> FEATURE:
<223> OTHER INFORMATION: Recombinant protein HBcAg183-SEQ22

<400> SEQUENCE: 41

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Arg Glu Leu
        115                 120                 125

Val Val Ser Tyr Val Asn Val Asn Met Gly Leu Lys Ile Arg Gln Leu
    130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Pro Ala Tyr
                165                 170                 175

Arg Pro Gln Asn Ala Pro Ile Leu Ser Thr Leu Pro Glu Thr Thr Val
            180                 185                 190

Val Arg Arg Arg Gly Arg Ser Pro Arg Arg Arg Thr Pro Ser Pro Arg
        195                 200                 205

Arg Arg Arg Ser Gln Ser Pro Arg Arg Arg Arg Ser Gln Ser Arg Glu
    210                 215                 220

Ser Gln Cys
225


<210> SEQ ID NO 42
<211> LENGTH: 193
<212> TYPE: PRT
<213> ORGANISM: Artificial
<220> FEATURE:
<223> OTHER INFORMATION: Recombinant protein HBcAg149-SEQ22

<400> SEQUENCE: 42

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Ser Thr Thr Ser Thr
                85                  90                  95
```

```
Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Arg Glu Leu
        115                 120                 125

Val Val Ser Tyr Val Asn Val Asn Met Gly Leu Lys Ile Arg Gln Leu
    130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Pro Ala Tyr
                165                 170                 175

Arg Pro Gln Asn Ala Pro Ile Leu Ser Thr Leu Pro Glu Thr Thr Val
            180                 185                 190

Val


<210> SEQ ID NO 43
<211> LENGTH: 25
<212> TYPE: PRT
<213> ORGANISM: Artificial
<220> FEATURE:
<223> OTHER INFORMATION: linker

<400> SEQUENCE: 43

Gly Gly Gly Gly Gly Ser Gly Gly Gly Gly Thr Gly Ser Glu Phe Gly
1               5                   10                  15

Gly Gly Gly Ser Gly Gly Gly Gly Ser
            20                  25


<210> SEQ ID NO 44
<211> LENGTH: 226
<212> TYPE: PRT
<213> ORGANISM: HBV

<400> SEQUENCE: 44

Met Glu Asn Ile Ala Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Gln Ile Ser Ser His Ser Pro Thr Cys
    50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Thr Cys Thr Thr Pro Ala
        115                 120                 125

Gln Gly Thr Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
```

-continued

```
        180                 185                 190

Ser Val Ile Trp Met Met Trp Phe Trp Gly Pro Ser Leu Tyr Asn Ile
        195                 200                 205

Leu Ser Pro Phe Met Pro Leu Leu Pro Ile Phe Phe Cys Leu Trp Val
    210                 215                 220

Tyr Ile
225


<210> SEQ ID NO 45
<211> LENGTH: 47
<212> TYPE: DNA
<213> ORGANISM: Artificial
<220> FEATURE:
<223> OTHER INFORMATION: primer

<400> SEQUENCE: 45

actttaagaa ggagatatac atatgatgga cattgatcct tataaag                  47


<210> SEQ ID NO 46
<211> LENGTH: 56
<212> TYPE: DNA
<213> ORGANISM: Artificial
<220> FEATURE:
<223> OTHER INFORMATION: primer

<400> SEQUENCE: 46

gtggtgctcg aggcggccgc aagcttttaa acgattgtat gctccggaag agtcga        56


<210> SEQ ID NO 47
<211> LENGTH: 67
<212> TYPE: DNA
<213> ORGANISM: Artificial
<220> FEATURE:
<223> OTHER INFORMATION: primer

<400> SEQUENCE: 47

gtggtgctcg aggcggccgc aagcttttag cagttggagg aagctggaga ctgagatctg     60

cggcgac                                                               67


<210> SEQ ID NO 48
<211> LENGTH: 47
<212> TYPE: DNA
<213> ORGANISM: Artificial
<220> FEATURE:
<223> OTHER INFORMATION: primer

<400> SEQUENCE: 48

actttaagaa ggagatatac atatgatgga aaaccttgaa agacttg                  47


<210> SEQ ID NO 49
<211> LENGTH: 54
<212> TYPE: DNA
<213> ORGANISM: Artificial
<220> FEATURE:
<223> OTHER INFORMATION: primer

<400> SEQUENCE: 49

gtggtgctcg aggcggccgc aagcttttag ataactgaag tttccggaag agtg          54


<210> SEQ ID NO 50
<211> LENGTH: 49
<212> TYPE: DNA
<213> ORGANISM: Artificial
<220> FEATURE:
```

<223> OTHER INFORMATION: primer

<400> SEQUENCE: 50
gtggtgctcg aggcggccgc aagcttttag caattgcttg ctggtcttg 49

<210> SEQ ID NO 51
<211> LENGTH: 47
<212> TYPE: DNA
<213> ORGANISM: Artificial
<220> FEATURE:
<223> OTHER INFORMATION: primer

<400> SEQUENCE: 51
actttaagaa ggagatatac atatgatgga cattgatcct tataaag 47

<210> SEQ ID NO 52
<211> LENGTH: 56
<212> TYPE: DNA
<213> ORGANISM: Artificial
<220> FEATURE:
<223> OTHER INFORMATION: primer

<400> SEQUENCE: 52
gtggtgctcg aggcggccgc aagcttttaa atgactgtgt gctctggaag agttga 56

<210> SEQ ID NO 53
<211> LENGTH: 67
<212> TYPE: DNA
<213> ORGANISM: Artificial
<220> FEATURE:
<223> OTHER INFORMATION: primer

<400> SEQUENCE: 53
gtggtgctcg aggcggccgc aagcttttag cagttggagg gagctggaga ttgagatctc 60
cggcgac 67

<210> SEQ ID NO 54
<211> LENGTH: 48
<212> TYPE: DNA
<213> ORGANISM: Artificial
<220> FEATURE:
<223> OTHER INFORMATION: primer

<400> SEQUENCE: 54
gatccacctc tgaacatgaa ctgacatgtc aggctgaggg ctaccccg 48

<210> SEQ ID NO 55
<211> LENGTH: 48
<212> TYPE: DNA
<213> ORGANISM: Artificial
<220> FEATURE:
<223> OTHER INFORMATION: primer

<400> SEQUENCE: 55
aattcggggt agccctcagc ctgacatgtc agttcatgtt cagaggtg 48

<210> SEQ ID NO 56
<211> LENGTH: 51
<212> TYPE: DNA
<213> ORGANISM: Artificial
<220> FEATURE:
<223> OTHER INFORMATION: primer

<400> SEQUENCE: 56
gatccttcaa acagtcttct ggtggtgacc cggaaatcgt tacccactct g 51

<210> SEQ ID NO 57
<211> LENGTH: 51
<212> TYPE: DNA
<213> ORGANISM: Artificial
<220> FEATURE:
<223> OTHER INFORMATION: primer

<400> SEQUENCE: 57
aattcagagt gggtaacgat ttccgggtca ccaccagaag actgtttgaa g 51

<210> SEQ ID NO 58
<211> LENGTH: 75
<212> TYPE: DNA
<213> ORGANISM: Artificial
<220> FEATURE:
<223> OTHER INFORMATION: primer

<400> SEQUENCE: 58
gatcctcatc aacaaccagc accggaccat gcaaaacctg cacaactcct gctcaaggaa 60
cctctatgtt tcccg 75

<210> SEQ ID NO 59
<211> LENGTH: 75
<212> TYPE: DNA
<213> ORGANISM: Artificial
<220> FEATURE:
<223> OTHER INFORMATION: primer

<400> SEQUENCE: 59
aattcgggaa acatagaggt tccttgagca ggagttgtgc aggttttgca tggtccggtg 60
ctggttgttg atgag 75

<210> SEQ ID NO 60
<211> LENGTH: 23
<212> TYPE: PRT
<213> ORGANISM: HBV

<400> SEQUENCE: 60

Ser Thr Thr Thr Ser Thr Gly Pro Cys Lys Thr Cys Thr Thr Pro Ala
1 5 10 15

Gln Gly Asn Ser Met Phe Pro
20

<210> SEQ ID NO 61
<211> LENGTH: 23
<212> TYPE: PRT
<213> ORGANISM: HBV

<400> SEQUENCE: 61

Thr Ser Thr Thr Ser Thr Gly Pro Cys Lys Thr Cys Thr Ile Pro Ala
1 5 10 15

Gln Gly Thr Ser Met Phe Pro
20

<210> SEQ ID NO 62
<211> LENGTH: 23
<212> TYPE: PRT
<213> ORGANISM: HBV

<400> SEQUENCE: 62

Ser Ser Thr Thr Ser Thr Gly Pro Cys Arg Thr Cys Thr Thr Pro Ala
1 5 10 15

Gln Gly Thr Ser Met Tyr Pro
20

<210> SEQ ID NO 63
<211> LENGTH: 75
<212> TYPE: DNA
<213> ORGANISM: Artificial
<220> FEATURE:
<223> OTHER INFORMATION: primer

<400> SEQUENCE: 63
gatcctctac caccacctct accggtccgt gcaaaacctg caccaccccg gctcagggta 60
actctatgtt cccgg 75

<210> SEQ ID NO 64
<211> LENGTH: 75
<212> TYPE: DNA
<213> ORGANISM: Artificial
<220> FEATURE:
<223> OTHER INFORMATION: primer

<400> SEQUENCE: 64
aattccggga acatagagtt accctgagcc ggggtggtgc aggttttgca cggaccggta 60
gaggtggtgg tagag 75

<210> SEQ ID NO 65
<211> LENGTH: 75
<212> TYPE: DNA
<213> ORGANISM: Artificial
<220> FEATURE:
<223> OTHER INFORMATION: primer

<400> SEQUENCE: 65
gatccacctc taccacctct accggtccgt gcaaaacctg caccatcccg gctcagggta 60
cctctatgtt cccgg 75

<210> SEQ ID NO 66
<211> LENGTH: 75
<212> TYPE: DNA
<213> ORGANISM: Artificial
<220> FEATURE:
<223> OTHER INFORMATION: primer

<400> SEQUENCE: 66
aattccggga acatagaggt accctgagcc gggatggtgc aggttttgca cggaccggta 60
gaggtggtag aggtg 75

<210> SEQ ID NO 67
<211> LENGTH: 75
<212> TYPE: DNA
<213> ORGANISM: Artificial
<220> FEATURE:
<223> OTHER INFORMATION: primer

<400> SEQUENCE: 67
gatcctcttc taccacctct accggtccgt gccgtacctg caccaccccg gctcagggta 60
cctctatgta cccgg 75

<210> SEQ ID NO 68
<211> LENGTH: 75
<212> TYPE: DNA
<213> ORGANISM: Artificial

<220> FEATURE:
<223> OTHER INFORMATION: primer

<400> SEQUENCE: 68
aattccgggt acatagaggt accctgagcc ggggtggtgc aggtacggca cggaccggta 60
gaggtggtag aagag 75

<210> SEQ ID NO 69
<211> LENGTH: 193
<212> TYPE: PRT
<213> ORGANISM: Artificial
<220> FEATURE:
<223> OTHER INFORMATION: Recombinant protein RBHBcAg149-SEQ60

<400> SEQUENCE: 69

Met Asp Ile Asp Pro Tyr Lys Glu Phe Gly Ala Ser Ser Gln Leu Ile
1 5 10 15

Ser Phe Leu Pro Glu Asp Phe Phe Pro Asn Leu Ala Glu Leu Val Glu
20 25 30

Thr Thr Thr Ala Leu Tyr Glu Glu Glu Leu Val Gly Lys Glu His Cys
35 40 45

Ser Pro His His Thr Ala Leu Arg Ser Leu Leu Asn Cys Trp Gly Glu
50 55 60

Thr Val Arg Leu Ile Thr Trp Val Arg Asn Ser Val Glu Gly Gly Gly
65 70 75 80

Gly Gly Ser Gly Gly Gly Gly Thr Gly Ser Ser Thr Thr Thr Ser Thr
85 90 95

Gly Pro Cys Lys Thr Cys Thr Thr Pro Ala Gln Gly Asn Ser Met Phe
100 105 110

Pro Glu Phe Gly Gly Gly Gly Ser Gly Gly Gly Gly Ser Gln Asp Ala
115 120 125

Ile Val Gln Gln Val Gln Ala Ser Val Gly Leu Arg Met Arg Gln Leu
130 135 140

Met Trp Phe His Leu Ser Cys Leu Thr Phe Gly Gln Pro Thr Val Ile
145 150 155 160

Glu Phe Leu Val Ser Phe Gly Thr Trp Ile Arg Thr Pro Gln Ala Tyr
165 170 175

Arg Pro Pro Asn Ala Pro Ile Leu Ser Thr Leu Pro Glu His Thr Ile
180 185 190

Val

<210> SEQ ID NO 70
<211> LENGTH: 193
<212> TYPE: PRT
<213> ORGANISM: Artificial
<220> FEATURE:
<223> OTHER INFORMATION: Recombinant protein RBHBcAg149-SEQ61

<400> SEQUENCE: 70

Met Asp Ile Asp Pro Tyr Lys Glu Phe Gly Ala Ser Ser Gln Leu Ile
1 5 10 15

Ser Phe Leu Pro Glu Asp Phe Phe Pro Asn Leu Ala Glu Leu Val Glu
20 25 30

Thr Thr Thr Ala Leu Tyr Glu Glu Glu Leu Val Gly Lys Glu His Cys
35 40 45

Ser Pro His His Thr Ala Leu Arg Ser Leu Leu Asn Cys Trp Gly Glu
50 55 60

Thr Val Arg Leu Ile Thr Trp Val Arg Asn Ser Val Glu Gly Gly Gly
65 70 75 80

Gly Gly Ser Gly Gly Gly Gly Thr Gly Ser Thr Ser Thr Thr Ser Thr
85 90 95

Gly Pro Cys Lys Thr Cys Thr Ile Pro Ala Gln Gly Thr Ser Met Phe
100 105 110

Pro Glu Phe Gly Gly Gly Gly Ser Gly Gly Gly Gly Ser Gln Asp Ala
115 120 125

Ile Val Gln Gln Val Gln Ala Ser Val Gly Leu Arg Met Arg Gln Leu
130 135 140

Met Trp Phe His Leu Ser Cys Leu Thr Phe Gly Gln Pro Thr Val Ile
145 150 155 160

Glu Phe Leu Val Ser Phe Gly Thr Trp Ile Arg Thr Pro Gln Ala Tyr
165 170 175

Arg Pro Pro Asn Ala Pro Ile Leu Ser Thr Leu Pro Glu His Thr Ile
180 185 190

Val

<210> SEQ ID NO 71
<211> LENGTH: 193
<212> TYPE: PRT
<213> ORGANISM: Artificial
<220> FEATURE:
<223> OTHER INFORMATION: Recombinant protein RBHBcAg149-SEQ62

<400> SEQUENCE: 71

Met Asp Ile Asp Pro Tyr Lys Glu Phe Gly Ala Ser Ser Gln Leu Ile
1 5 10 15

Ser Phe Leu Pro Glu Asp Phe Phe Pro Asn Leu Ala Glu Leu Val Glu
20 25 30

Thr Thr Thr Ala Leu Tyr Glu Glu Glu Leu Val Gly Lys Glu His Cys
35 40 45

Ser Pro His His Thr Ala Leu Arg Ser Leu Leu Asn Cys Trp Gly Glu
50 55 60

Thr Val Arg Leu Ile Thr Trp Val Arg Asn Ser Val Glu Gly Gly Gly
65 70 75 80

Gly Gly Ser Gly Gly Gly Gly Thr Gly Ser Ser Ser Thr Thr Ser Thr
85 90 95

Gly Pro Cys Arg Thr Cys Thr Thr Pro Ala Gln Gly Thr Ser Met Tyr
100 105 110

Pro Glu Phe Gly Gly Gly Gly Ser Gly Gly Gly Gly Ser Gln Asp Ala
115 120 125

Ile Val Gln Gln Val Gln Ala Ser Val Gly Leu Arg Met Arg Gln Leu
130 135 140

Met Trp Phe His Leu Ser Cys Leu Thr Phe Gly Gln Pro Thr Val Ile
145 150 155 160

Glu Phe Leu Val Ser Phe Gly Thr Trp Ile Arg Thr Pro Gln Ala Tyr
165 170 175

Arg Pro Pro Asn Ala Pro Ile Leu Ser Thr Leu Pro Glu His Thr Ile
180 185 190

Val

<210> SEQ ID NO 72
<211> LENGTH: 197
<212> TYPE: PRT
<213> ORGANISM: Artificial

<220> FEATURE:
<223> OTHER INFORMATION: Recombinant protein TBHBcAg153-SEQ60

<400> SEQUENCE: 72

Met Glu Asn Leu Glu Arg Leu Asp Ile Tyr Lys Glu Phe Gly Val Ser
1 5 10 15

Asp Val Leu Val Ser Phe Leu Pro Asp Asp Phe Phe Pro Thr Leu Gln
20 25 30

Gln Leu Leu Glu Ser Val Asn Ala Leu Tyr Glu Asp Glu Leu Thr Gly
35 40 45

Pro Asn His Cys Ser Pro His His Thr Ala Leu Arg His Leu Ile Met
50 55 60

Cys Gly Val Glu Leu Arg Asp Phe Ile Asp Trp Met His Glu Gln Gly
65 70 75 80

Gly Gly Gly Gly Ser Gly Gly Gly Gly Thr Gly Ser Ser Thr Thr Thr
85 90 95

Ser Thr Gly Pro Cys Lys Thr Cys Thr Thr Pro Ala Gln Gly Asn Ser
100 105 110

Met Phe Pro Glu Phe Gly Gly Gly Gly Ser Gly Gly Gly Gly Ser Asp
115 120 125

Ala Asp Ala Leu Leu Ala Gly Tyr Leu Arg Ser Lys Tyr Leu Lys His
130 135 140

Ile Thr Lys Ala Ile Trp Tyr His Leu Ser Cys Leu Thr Phe Gly Lys
145 150 155 160

Gln Thr Val His Glu Tyr Leu Val Ser Phe Gly Thr Trp Ile Arg Thr
165 170 175

Pro Ala Ala Tyr Arg Pro Val Asn Ala Pro Ile Leu Thr Thr Leu Pro
180 185 190

Glu Thr Ser Val Ile
195

<210> SEQ ID NO 73
<211> LENGTH: 197
<212> TYPE: PRT
<213> ORGANISM: Artificial
<220> FEATURE:
<223> OTHER INFORMATION: Recombinant protein TBHBcAg153-SEQ61

<400> SEQUENCE: 73

Met Glu Asn Leu Glu Arg Leu Asp Ile Tyr Lys Glu Phe Gly Val Ser
1 5 10 15

Asp Val Leu Val Ser Phe Leu Pro Asp Asp Phe Phe Pro Thr Leu Gln
20 25 30

Gln Leu Leu Glu Ser Val Asn Ala Leu Tyr Glu Asp Glu Leu Thr Gly
35 40 45

Pro Asn His Cys Ser Pro His His Thr Ala Leu Arg His Leu Ile Met
50 55 60

Cys Gly Val Glu Leu Arg Asp Phe Ile Asp Trp Met His Glu Gln Gly
65 70 75 80

Gly Gly Gly Gly Ser Gly Gly Gly Gly Thr Gly Ser Thr Ser Thr Thr
85 90 95

Ser Thr Gly Pro Cys Lys Thr Cys Thr Ile Pro Ala Gln Gly Thr Ser
100 105 110

Met Phe Pro Glu Phe Gly Gly Gly Gly Ser Gly Gly Gly Gly Ser Asp
115 120 125

Ala Asp Ala Leu Leu Ala Gly Tyr Leu Arg Ser Lys Tyr Leu Lys His

-continued

```
    130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
        195


<210> SEQ ID NO 74
<211> LENGTH: 197
<212> TYPE: PRT
<213> ORGANISM: Artificial
<220> FEATURE:
<223> OTHER INFORMATION: Recombinant protein TBHBcAg153-SEQ62

<400> SEQUENCE: 74

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Ser Ser Thr Thr
                85                  90                  95

Ser Thr Gly Pro Cys Arg Thr Cys Thr Thr Pro Ala Gln Gly Thr Ser
            100                 105                 110

Met Tyr Pro Glu Phe Gly Gly Gly Gly Ser Gly Gly Gly Gly Ser Asp
        115                 120                 125

Ala Asp Ala Leu Leu Ala Gly Tyr Leu Arg Ser Lys Tyr Leu Lys His
    130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
        195
```